United States Patent
Aebi et al.

(10) Patent No.: US 6,541,638 B2
(45) Date of Patent: Apr. 1, 2003

(54) PYRROLIDINE DERIVATIVES

(75) Inventors: Johannes Aebi, Basel (CH); Denise Blum, Basel (CH); Daniel Bur, Therwil (CH); Alexander Chucholowski, San Diego, CA (US); Henrietta Dehmlow, Grenzach-Wyhlen (DE); Eric Argirios Kitas, Arlesheim (CH); Bernd Michael Loeffler, Oberrimsingen (DE); Ulrike Obst, Grenzach-Wyhlen (DE); Sabine Wallbaum, Ostfildern (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/907,135

(22) Filed: Jul. 17, 2001

(65) Prior Publication Data
US 2002/0049243 A1 Apr. 25, 2002

(30) Foreign Application Priority Data

Jul. 19, 2000 (EP) ............................................ 00114947

(51) Int. Cl.$^7$ ...................... A61K 31/454; A61K 31/40; A61K 31/4025; C07D 401/06; C07D 403/06
(52) U.S. Cl. .................... 546/208; 546/278.4; 548/252; 548/518; 548/519; 548/531; 548/541; 548/542; 548/543; 514/326; 514/381; 514/343; 514/422; 514/423; 514/424
(58) Field of Search ........................ 546/208; 548/518, 548/519, 531, 542, 543; 514/326, 422, 423, 424

(56) References Cited

U.S. PATENT DOCUMENTS 4,933,333 A * 6/1990 Sunagawa ................... 514/192

FOREIGN PATENT DOCUMENTS

| EP | 0126587 | 11/1984 |
|---|---|---|
| EP | 0472062 | 2/1992 |
| EP | 0551993 | 7/1993 |
| EP | 1078927 | 2/2001 |
| WO | WO 98/08814 | 3/1998 |
| WO | WO 98/08815 | 3/1998 |
| WO | WO 99/02492 | 1/1999 |
| WO | WO 99/57121 | 11/1999 |

OTHER PUBLICATIONS

Brands KMJ et al. Tetrahedron Lett. (1996), 37(17), 2919–22.*

Greene TW & Wuts PGM. Protective Groups in Organic Synthesis, (1991). pp. 309–310, 313.*

Brands K M J, et al., *Tetrahedron Letters*, Elsevier Science Publishers, Amsterdam, NL, 37, No. 17, pp. 2919–2922 (1996).

Arwel Lewis, et al, *Journal of the Chemical Society*, Perkin Transactions 1, Chemical Society, Letchworth, GB, pp. 3777–3793 (1998).

* cited by examiner

*Primary Examiner*—Evelyn Mei Huang
(74) *Attorney, Agent, or Firm*—George W. Johnston; Patricia S. Rocha-Tramaloni; Bernard Lau

(57) ABSTRACT

The present invention relates to pyrrolidine derivatives and dimeric forms and/or pharmaceutically acceptable esters, and/or salts thereof. The compounds are useful as inhibitors of metalloproteases, e.g. zinc proteases, particularly zinc hydrolases, and which are effective in treating disease states are associated with vasoconstriction of increasing occurrences.

15 Claims, No Drawings

PYRROLIDINE DERIVATIVES

FIELD OF THE INVENTION

The present invention is directed to compounds which are useful as inhibitors of metalloproteases, e.g. zinc proteases, particularly zinc hydrolases, and which are effective in the prophylaxis and treatment of disease states which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. In addition the compounds are useful as cytostatic and cerebroprotective agents for inhibition of graft rejection, for organ protection and for treatment of ophthalmological diseases.

BACKGROUND

Endothelins are peptides, that exist in three isoforms ET-1, ET-2, and ET-3, each encoded by a distinct gene. They have been originally discovered in the conditioned medium of porcine endothelial cells in 1988 by Yanagisawa (Yanagisawa M; Kurihara H; Kimura S; Tomobe Y; Kobayashi M; Mitsui Y; Yazaki Y; Goto K; Masaki T: A novel potent vasoconstrictor peptide produced by vascular endothelial cells [see comments]. NATURE (1988 Mar 31), 332(6163), 411–5.). The active ETs are peptides of 21 amino acids with two intramolecular disulfide bridges. They are produced from preproproteins of 203 to 212 amino acids which are processed by furin like endopeptidases to the biologically inactive big-endothelin (big-ET). The big-ETs are specifically processed to mature ETs by a hydrolytic cleavage between amino acids 21 and 22 that are $Trp^{21}$-$Val^{22}$ (big-ET-1, big ET-2) and $Trp^{21}$-$Ile^{22}$ in big-ET-3 respectively. Already in 1988 a specific metalloprotease was postulated to be responsible for this specific cleavage. In 1994 ECE-1 (endothelin converting enzyme-1) was purified and cloned from bovine adrenal (Xu D, Emoto N, Giaid A, Slaughter C, Kaw S, de Witt D, Yanagisawa M: ECE-1: a membrane-bound metalloprotease that catalyzes the proteolytic activation of big endothelin-1. Cell (1994) 78: 473–485.).

ECE-1 is a membrane bound type II zinc-endopeptidase with a neutral pH optimum and a zinc binding motif HExxHx(>20)E. It belongs to subfamily M13 and has a large 681 amino acid ectodomain that comprises the active site. Other members of the M13 family are NEP24.11 (neutral endopeptidase), PEX, a phosphate regulating neutral endopeptidase, and Kell blood group protein that has recently been described as a big-ET-3 processing enzyme. Members of the M13 family of human origin are characterized by a high molecular weight (>80 kDa) a number of conserved disulfide bridges and a complex glycosylation pattern. The structure of NEP has recently been solved. (Oefner et al, J. Mol. Biol. 2000, 296, 341–349). The catalytic domain of ECE and related human M13 proteinases are significantly larger (>650 amino acids) than members of matrix metalloproteases (MMPs). Unlike the family of the MMPs which belong to the metzincins and display a typical HExxHxxGxxH pattern members of the M13 family are gluzincins comprising a HExx(>20)E pattern. These two families are clearly different in size of catalytic domains, structure and zinc coordinating pattern of ligands. Active sites of the two families show clear differences which has clear impact on type of inhibitors and the potential selectivity.

BRIEF SUMMARY OF THE INVENTION

The invention is directed to a compound of formula I

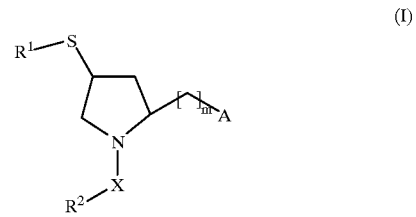

(I)

wherein $R^1$ is hydrogen, alkylcarbonyl, or arylcarbonyl;

$R^2$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or hetercycylalkyl;

A is —C(O)—$R^3$, —CH(OH)—$R^4$, or —C(O)—$NR^5R^6$, wherein $R^3$ and $R^4$ are independently alkyl, aryl, arylalkinyl, arylalkyl, or arylalkenyl;

$R^5$ is hydrogen, alkyl, cycloalkyl, cycloalkylalkyl, carboxyalkyl, or arylalkyl;

$R^6$ is alkyl, alkylcarbonylalkyl, cyanoalkyl, hydroxyalkyl, hydroxyalkyl-(hydroxyalkyl), alkoxycarbonylalkyl, arylalkyl, arylcarbonylalkyl, arylaminocarbonylalkyl, aryl(alkyl)aminocarbonylalkyl, aminocarbonylalkyl, aryl, arylalkyl, heteroaryl, heteroarylalkyl, heterocyclyl, cycloalkyl, cycloalkylalkyl, or carboxyalkyl, or $R^6$ is formula IIa, IIb, or IIc;

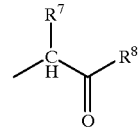

(IIa)

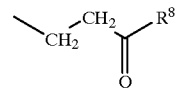

(IIb)

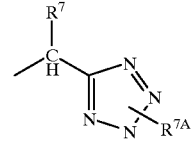

(IIc)

or

—$NR^5R^6$ in —C(O)—$NR^5R^6$ for A represents a 5 or 6 membered saturated ring, unsubstituted or substituted with carboxy, alkyloxycarbonyl, hydroxy, alkoxycarbonylalkoxy, phenylalkyl, or phenylalkoxycarbonyl;

$R^7$ is hydrogen, alkyl, alkenyl, alkylthioalkyl, aryl, heteroaryl, carboxyalkyl, carboxy, alkoxycarbonylalkyl, arylalkyl, or heteroarylalky; or a compound of formula III

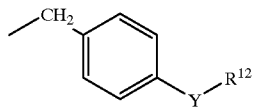

(III)

R$^{7A}$ is hydrogen or alkyl;
R$^8$ is —OR$^9$ or —NR$^{10}$R$^{11}$, wherein
R$^9$ is hydrogen, alkyl, arylalkyl; R$^{10}$ is hydrogen or alkyl; and R$^{11}$ is alkyl, aryl, heteroaryl, arylalkyl, or the group —NR$^{10}$OR$^{11}$ represents a 5 or 6 membered ring unsubstituted or substituted with carboxy, alkyloxycarbonyl, hydroxy, alkoxycarbonylalkoxy, phenylalkyl, or phenylalkoxycarbonyl;
R$^{12}$ is alkyl, aryl, or arylalkyl;
Y is —O—, —O—S(O$_2$)—, —O—C(O)— or —O—C(O)—NH—;
m is 0, 1, or 2;
X is —SO$_2$, —CO—, —C(O)O—, —SO$_2$NH—, or —C(O)NR$^{13}$— wherein R$^{13}$ is hydrogen, alkyl, aryl, or carboxyalkyl;
or a dimeric form, or a pharmaceutically acceptable ester, or a pharmaceutically acceptable salt thereof.

DETAILED DESCRIPTION OF THE INVENTION

The term "alkyl", alone or in combination, means a straight-chain or branched-chain alkyl group containing a maximum of 7, preferably a maximum of 4, carbon atoms, e.g., methyl, ethyl, n-propyl, 2-methylpropyl (iso-butyl), 1-methylethyl (iso-propyl), n-butyl, and 1,1-dimethylethyl (t-butyl).

The term "carboxy" refers to the group —C(O)OH.

The term "carbonyl" refers to the group —C(O)—.

The term "halogen" refers to the group fluoro, bromo, chloro and iodo.

The term "alkenyl" refers to a hydrocarbon chain as defined for alkyl having at least one olefinic double bond (including for example, vinyl, allyl and butenyl).

The term "alkinyl" refers to a hydrocarbon chain as defined for alkyl having at least one olefinic triple bond (including for example propinyl, butin-(1)-yl, etc.).

The term "alkoxy", alone or in combination, means an alkyl ether group in which the term 'alkyl' has the significance given earlier, such as methoxy, ethoxy, n-propoxy, isopropoxy, n-butoxy, isobutoxy, sec.butoxy, tert.butoxy and the like.

The term "alkoxycarbonyl" refers to a group of the formula —C(O)R$_c$ wherein R$_c$ is alkoxy as defined above.

The term "hydroxy" refers to the group —OH, the term "cyano" to the group —CN.

The term "hydroxyalkyl" means an alkyl group as defined earlier which is substituted by a hydroxy group.

The term "thioalkyl" and "cyanoalkyl" refer to an alkyl group as defined earlier which is substituted by a —SH group or an —CN group, respectively.

The term "halogenalkyl" refers to an alkyl group as defined earlier which is substituted by one to three halogen atoms, preferably fluoro, e.g. trifluoromethyl, 2,2,2-trifluoroethyl, etc.

The term "alkylthioalkyl" is a group of the formula alkyl-S-alkyl.

"Carboxyalkyl" means a lower-alkyl as defined above which is substituted by a HOOC-group.

The term "alkylcarbonyl", alone or in combination, means an acyl group derived from an alkanecarboxylic acid, i.e. alkyl—C(O)—, such as acetyl, propionyl, butyryl, valeryl, 4-methylvaleryl etc.

The term "cycloalkyl" signifies a saturated, cyclic hydrocarbon group with 3–8, preferably 3–6 carbon atoms, i.e. cyclopropyl, cyclobutyl, cyclopentyl and cyclohexyl and the like.

The term "amino" refers to the group —NH$_2$.

The term "aryl" for R$^2$—alone or in combination—, refers to an aromatic carbocyclic radical, i.e. a 6 or 10 membered aromatic or partially aromatic ring, e.g. phenyl, naphthyl, tetrahydronaphthyl, fluorenyl or biphenyl, preferably phenyl or naphthyl, and most preferably naphthyl. The aryl moiety, especially phenyl, is unsubstituted or substituted with one or more groups independently selected from halogen, preferably fluoro, alkyl, alkoxy, mono- or dialkylamino, carboxy, alkoxy, and alkylcarbonylamino.

The term "heteroaryl" for R$^2$—alone or in combination—refers to an aromatic mono—or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, pyridinyl, pyrrolyl, imidazolyl, tetrazolyl, preferably thiophenyl. Optionally, the heteroaryl group can be mono-, di- or tri-substituted, independently, with alkyl, alkylcarbonyl, halogen, preferably fluoro, alkoxycarbonyl, hydroxy, amino, alkylamino, dialkylamino, carboxy, alkoxycarbonylalkyl, preferably alkyl. The preferred heteroaryl group is thiophenyl.

The term "aryl" for R$^1$ and R$^3$ to R$^{12}$—alone or in combination—refers to an aromatic carbocyclic radical, i.e. a 6 or 10 membered aromatic or partially aromatic ring, e.g. phenyl, naphthyl or tetrahydronaphthyl, preferably phenyl. The aryl moiety is optionally substituted with one or more groups independently selected from halogen, preferably fluoro, alkoxycarbonyl, e.g. methylcarbonyl, alkyloxycarbonylalkoxy, carboxy, carboxyalkoxy, cyano, alkyl, alkoxy, phenyl, phenoxy, phenylalkyl, phenylalkoxy, trifluormethyl, trifluormethoxy, hydroxy, alkylamido, e.g. acetamido, nitro, alkylsulfonyl, e.g. methylsulfonyl. The preferred substituents are fluoro, carboxy, alkyloxycarbonyl, hydroxy, hydroxyalkyl, alkoxycarbonylalkoxy, carboxyalkyl, and carboxyalkoxy.

The term "aryloxy" refers to an aryl group as defined above attached to a parent structure via an oxy radical, i.e., aryl—O—.

The term "heteroaryl" for R$^3$ and R$^4$ to R$^{10}$—alone or in combination—refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, pyridinyl, pyrrolyl, imidazolyl, tetrazolyl, indolyl, benzoimidazolyl, oxadiazolyl, preferably pyridinyl, isoxazolyl, benzodioxolyl and thiazolyl, preferably indolyl, tetrazolyl, benzoimidazolyl, oxadiazolyl, and benzodioxolyl. Optionally, the heteroaryl group can be mono-, di- or tri-substituted, independently, with halogen, alkyl, alkylcarbonyl, alkoxycarbonyl, hydroxy, amino, alkylamino, dialkylamino, carboxy, alkoxycarbonylalkyl, preferably alkyl or halogen, preferably fluoro.

The term "heterocyclyl" —alone or in combination—refers to a non-aromatic mono- or bicyclic radical having 5 to 10, preferably 5 to 6 ring atoms, containing one to three heteroatoms, preferably one heteroatom, e.g. independently selected from nitrogen, oxygen or sulfur. Optionally the heterocyclic ring can be substituted by a group independently selected from halogen, alkyl, alkoxy, oxocarboxy, alkoxycarbonyl, etc. and/or on a secondary nitrogen atom (i.e. —NH—) by alkyl, arylalkoxycarbonyl, alkylcarbonyl or on a tertiary nitrogen atom (i.e. =N—) by oxido. Examples for heterocyclic groups are morpholinyl, pyrrolidinyl, piperidyl, etc.

The term "dimeric form" means a compound wherein the two $R^1$ groups of two identical compounds of formula I have been replaced by a common single bond or wherein $R^1$ is glutathione-S— or cysteine-S— or ester and/or alkylcarbonyl or arylcarbonyl derivatives thereof, e.g. acetylcysteine-S— or benzoylcysteine-S—, preferably glutathione-S—, cysteine-S—, acetylcysteine-S— or benzoylcysteine-S—.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) are useful in inhibiting mammalian metalloprotease activity, particularly zinc hydrolase activity. More specifically, the compounds of formula (I) are useful as medicaments for the treatment and prophylaxis of disorders which are associated with diseases caused by endothelin-converting enzyme (ECE) activity. Inhibiting of this enzyme would be useful for treating myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma. In addition the compounds are useful as cytostatic and cerebroprotective agents, for inhibition of graft rejection, for organ protection and for treatment of ophthalmological diseases.

In more detail, the present invention relates to compounds of formula (I)

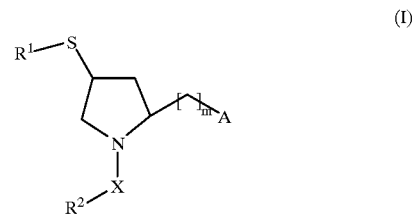

wherein
$R^1$ is hydrogen, alkylcarbonyl, or arylcarbonyl;
$R^2$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl(alkoxycarbonyl)alkyl, heteroaryl, heteroarylalkyl, heterocyclyl or hetercycylalkyl;
A is —C(O)—$R^3$, —CH(OH)—$R^4$, or —C(O)—$NR^5R^6$, wherein
$R^3$ and $R^4$ are independently alkyl, aryl, arylalkinyl, arylalkyl, or arylalkenyl;
$R^5$ is hydrogen, alkyl, cycloalkyl, cycloalkylalkyl, carboxyalkyl, or arylalkyl;
$R^6$ is alkyl, alkylcarbonylalkyl, cyanoalkyl, hydroxyalkyl, hydroxyalkyl-(hydroxyalkyl), alkoxycarbonylalkyl, arylalkyl, arylcarbonylalkyl, arylaminocarbonylalkyl, aryl(alkyl)aminocarbonylalkyl, aminocarbonylalkyl, aryl, arylalkyl, heteroaryl, heteroarylalkyl, heterocyclyl, cycloalkyl, cycloalkylalkyl, or carboxyalkyl, or $R^6$ is formula IIa, IIb, or IIc;

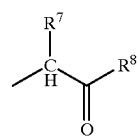

(IIa)

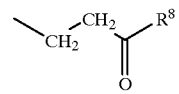

(IIb)

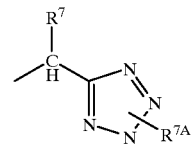

(IIc)

or
—$NR^5R^6$ in —C(O)—$NR^5R^6$ for A represents a 5 or 6 membered saturated ring, unsubstituted or substituted with carboxy, alkyloxycarbonyl, hydroxy, alkoxycarbonylalkoxy, phenylalkyl, or phenylalkoxycarbonyl;
$R^7$ is hydrogen, alkyl, alkenyl, alkylthioalkyl, aryl, heteroaryl, carboxyalkyl, carboxy, alkoxycarbonylalkyl, arylalkyl, or heteroarylalkyl; or a compound of formula III

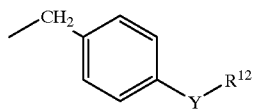
(III)

$R^{7A}$ is hydrogen or alkyl
$R^8$ is —$OR^9$ or —$NR^{10}R^{11}$, wherein
$R^9$ is hydrogen, alkyl, arylalkyl; $R^{10}$ is hydrogen or alkyl; and $R^{11}$ is alkyl, aryl, heteroaryl, arylalkyl, or the group —$NR^{10}R^{11}$ represents a 5 or 6 membered ring unsubstituted or substituted with carboxy, alkyloxycarbonyl, hydroxy, alkoxycarbonylalkoxy, phenylalkyl, or phenylalkoxycarbonyl;
$R^{12}$ is alkyl, aryl, or arylalkyl;
Y is —O—, —O—S($O_2$)—, —O—C(O)— or —O—C(O)—NH—;
m is 0, 1, or 2;
X is —$SO_2$—, —CO—, —C(O)O—, —$SO_2$NH—, or —C(O)$NR^{13}$— wherein $R^{13}$ is hydrogen, alkyl, aryl, or carboxyalkyl;
and
dimeric forms, and/or pharmaceutically acceptable esters, and/or pharmaceutically acceptable salts thereof, preferably pharmaceutically acceptable esters, and/or pharmaceutically acceptable salts thereof, and most preferably pharmaceutically acceptable salts thereof Particularly, the present invention refers to the compounds of formula (I) wherein $R^1$ is hydrogen or alkylcarbonyl, preferably $R^1$ is hydrogen or acetyl, and more preferably $R^1$ is hydrogen.

Further, the present invention refers to the above compounds wherein $R^2$ is alkyl, alkylcycloalkyl, alkylcycloalkylalkyl, cycloalkyl, halogenalkyl, carboxyalkyl, aryl, arylalkyl, arylalkyl(alkoxycarbonyl)alkyl, arylcarbonylalkyl, aryloxyalkyl, arylalkenyl, or aryl(alkoxycarbonyl)alkyl, preferably wherein $R^2$ is alkyl, aryl or arylalkyl, more preferably wherein $R^2$ is alkyl, phenyl or naphthyl, and most preferabyl wherein $R^2$ is naphthyl.

A further preferred embodiment of the present invention are the above compounds wherein $R^3$ and $R^4$ are independently alkyl, phenyl, phenylalkinyl, phenylalkyl, or phenylalkenyl, preferably $R^3$ is alkyl, phenyl, phenylalkinyl, or $R^4$ is phenylalkinyl, phenylalkyl, or phenylalkenyl.

Another preferred embodiment of the present invention refers to the above compounds of formula (I) wherein A is —C(O)—$NR^5R^6$.

In another preferred embodiment the invention refers to the above compounds wherein X preferably is —$SO_2$— or —C(O)(O)—.

In a preferred embodiment of the present invention m is 0 or 1, preferably m is 0.

In a further preferred embodiment of the present invention the compound of formula (I) may be characterized in that $R^5$ is alkyl, cycloalkyl, cycloalkylalkyl, carboxyalkyl, or arylalkyl, preferably that $R^5$ is alkyl, arylalkyl, or cycloalkyl.

Particularly, the invention refers to the above compounds, wherein —$NR^5R^6$ in —C(O)—$NR^5R^6$ for A represents a 5 or 6 membered ring, e.g. a piperidinyl or pyrrolidinyl ring, preferably piperidinyl, unsubstituted or substituted with carboxy, alkyloxycarbonyl, hydroxy, alkoxycarbonylalkoxy, phenylalkyl, or phenylalkoxycarbonyl, preferably alkoxycarbonyl or carboxy. Preferably —$NR^5R^6$ is piperidinyl or pyrrolidinyl, optionally substituted with alkoxycarbonyl or carboxy, more preferably —$NR^5R^6$ is piperidinyl.

In a preferred embodiment $R^6$ is alkyl, alkylcarbonylalkyl, cyanoalkyl, hydroxyalkyl, hydroxyalkyl-(hydroxyalkyl), alkoxycarbonylalkyl, arylalkyl, arylcarbonylalkyl, arylaminocarbonylalkyl, aryl(alkyl)aminocarbonylalkyl, aminocarbonylalkyl, aryl, arylalkyl, heteroaryl, heteroarylalkyl, heterocyclyl, cycloalkyl, cycloalkylalkyl, carboxyalkyl, or —$NR^5R^6$ in the group —C(O)—$NR^5R^6$ represents a 5 or 6 membered ring as defined above, unsubstituted or substituted with carboxy, alkyloxycarbonyl, hydroxy, alkoxycarbonylalkoxy, phenylalkyl, or phenylalkoxycarbonyl, or $R^6$ is a group of the formula

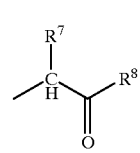
(IIa)

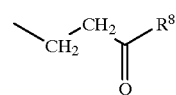
(IIb)

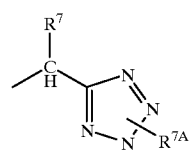
(IIc)

wherein $R^7$, $R^{7a}$, $R^8$ and $R^{12}$ are as defined above. Preferably, $R^7$ is hydrogen, alkyl, alkenyl, alkylthioalkyl, aryl, arylalkyl, heteroaryl, heteroarylalkyl, carboxyalkyl, carboxy, alkoxycarbonylalkyl; $R^{7A}$ is hydrogen or alkyl, and $R^8$ is $OR^9$ or —$NR^{10}R^{11}$, wherein $R^9$ is hydrogen, alkyl, arylalkyl; $R^{10}$ is hydrogen or alkyl; and $R^{11}$ is aryl, heteroaryl, arylalkyl, or the group —$NR^{10}R^{11}$ forms a 5 or 6 membered saturated ring as described above for —$NR^5R^6$; Y is preferably —O—; —O—S($O_2$)—, —O—C(O)— or —O—C(O)—NH—, more preferably —O—S($O_2$)—, —O—C(O)— or —O—C(O)—NH—, and $R^{12}$ is alkyl, aryl or arylalkyl.

In a preferred embodiment the invention comprises the above compounds, wherein $R^6$ is alkyl, alkylcarbonylalkyl, cyanoalkyl, hydroxyalkyl, hydroxyalkyl-(hydroxyalkyl), alkoxycarbonylalkyl, arylalkyl, arylcarbonylalkyl, arylaminocarbonylalkyl, aryl(alkyl)aminocarbonylalkyl, aminocarbonylalkyl, aryl, arylalkyl, heteroaryl, heteroarylalkyl, cycloalkyl, cycloalkylalkyl, carboxyalkyl, or heterocyclyl, preferably wherein $R^6$ is alkyl, alkylcarbonylalkyl, arylalkyl, arylcarbonylalkyl, heteroarylalkyl, carboxyalkyl, and more preferably wherein $R^6$ is alkyl, alkylcarbonylalkyl, benzyl, tetrazolylethyl, phenylcarbonylmethyl, or oxadiazolylmethyl.

The invention comprises also compounds, wherein $R^6$ is a group of formula (IIa) or (IIb)

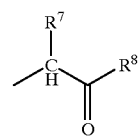
(IIa)

-continued

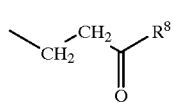
(IIb)

wherein R⁷ is hydrogen, alkyl, alkenyl, alkylthioalkyl, aryl, heteroaryl, carboxyalkyl, carboxy, alkoxycarbonylalkyl, arylalkyl or heteroarylalkyl; or R⁷ is a group of the formula III

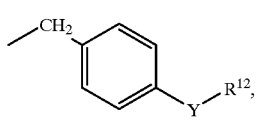
(III)

wherein Y is —O—, —O—S(O₂)—, —O—C(O)— or —O—C(O)—NH— and R¹² is aryl, preferably phenyl and R⁸ is OR⁹ or —NR¹⁰R¹¹, wherein R⁹ is hydrogen, alkyl, arylalkyl; R¹⁰ is hydrogen or alkyl; and R¹¹ is aryl, heteroaryl, arylalkyl.

In addition, the invention refers to the above compounds, wherein R⁶ is a group of the formula

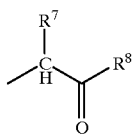
(IIa)

wherein R⁷ and R⁸ are as defined above.

Preferably, R⁷ is hydrogen in the above compounds and R⁸ is —NR¹⁰OR¹¹ and R¹⁰ and R¹¹ are as defined above. In these compounds R¹⁰ preferably is hydrogen or methyl and R¹¹ preferably is aryl, more preferably R¹¹ is phenyl, unsubstituted or substituted with alkoxycarbonyl, carboxy, or hydroxyalkyl.

Other preferred embodiments of the present invention refer to compounds wherein A is —C(O)—R³ or —CH(OH)—R⁴. R³ and R⁴ are as defined above.

In a most preferred embodiment the present invention comprises compounds of the formula

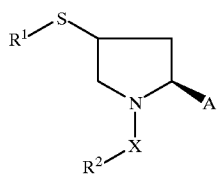
(IV)

wherein R¹, R², A and X are as defined above.

Preferred embodiments of the present invention are the compounds exemplified in the examples. Especially, the invention comprises the following compounds
a) (2S,4S)-1-[4-Mercapto-1-(naphthalene-2-sulfonyl)-pyrrolidine-2-carbonyl]-piperidine-4-carboxylic acid ethyl ester;
b) (2S,4S)-1-[4-Mercapto-1-(naphthalene-2-sulfonyl)-pyrrolidine-2-carbonyl]-piperidine-4-carboxylic acid;
c) (2S,4R)-4-Mercapto-1-(naphthalene-2-sulfonyl)-pyrrolidine-2-carboxylic acid benzyl-methyl-amide;
d) (2S,4R)-2-[2-[[4-Mercapto-1-(naphthalene-2-sulfonyl)-pyrrolidine-2-carbonyl]-methyl-amino]-acetylamino]-benzoic acid methyl ester;
e) (2S,4R)-2-[2-[[4-Mercapto-1-(naphthalene-2-sulfonyl)-pyrrolidine-2-carbonyl]-methyl-amino]-acetylamino]-benzoic acid;
f) (2S,4R)-4-[[[[4-Mercapto-1-(naphthalene-2-sulfonyl)-pyrrolidine-2-carbonyl]-methyl-amino]-acetyl]-methyl-amino]-benzoic acid;
g) (2S,4R)-4-[[[[4-Mercapto-1-(naphthalene-2-sulfonyl)-pyrrolidine-2-carbonyl]-methyl-amino]-acetyl]-methyl-amino]-benzoic acid methyl ester;
h) (2S,4R)-4-Mercapto-1-(naphthalene-2-sulfonyl)-pyrrolidine-2-carboxylic acid [[(4-hydroxymethyl-phenyl)-methyl-carbamoyl]-methyl]-methyl-amide;
i) (2S,4R)-3-{Benzyl-[4-mercapto-1-(naphthalene-2-sulfonyl)-pyrrolidine-2-carbonyl]-amino}-propionic acid;
j) (2S,4R)-4-Mercapto-1-(naphthalene-2-sulfonyl)-pyrrolidine-2-carboxylic acid cyclopropyl-[2-(1H-tetrazol-5-yl)-ethyl]-amide;
k) (2S,4R)-1-[4-Mercapto-1-(naphthalene-2-sulfonyl)-pyrrolidin-2-yl]-3-methyl-butan-1-one;
l) (2S,4R)-[[4-Mercapto-1-(naphthalene-2-sulfonyl)-pyrrolidine-2-carbonyl]-(3-methyl-butyl)-amino]-acetic acid;
m) (2S,4R)-2-(Benzyl-methyl-carbamoyl)-4-mercapto-pyrrolidine-1-carboxylic acid isopropyl ester;
n) (2S,4R)-2-(Benzyl-methyl-carbamoyl)-4-mercapto-pyrrolidine-1-carboxylic acid pentyl ester;
o) (2S,4R)-4-Mercapto-1-(naphthalene-2-sulfonyl)-pyrrolidine-2-carboxylic acid benzyl-[2-(1H-tetrazol-5-yl)-ethyl]-amide;
p) (2S,4R)-4-Mercapto-1-(naphthalene-2-sulfonyl)-pyrrolidine-2-carboxylic acid hexyl-methyl-amide;
q) (2S,4R)-4-Mercapto-1-(naphthalene-2-sulfonyl)-pyrrolidine-2-carboxylic acid methyl-(2-oxo-2-phenyl-ethyl)-amide;
r) (2S,4R)-4-Mercapto-1-(naphthalene-2-sulfonyl)-pyrrolidine-2-carboxylic acid methyl-(4-methyl-2-oxo-pentyl)-amide;
s) (2S,4R)-4-Mercapto-1-(naphthalene-2-sulfonyl)-pyrrolidine-2-carboxylic acid (3-methyl-butyl)-[1,2,4]oxadiazol-3-ylmethyl-amide;
t) (2S,4R)-2-((S) or (R)-1-Hydroxy-3-phenyl-prop-2-ynyl)-4-mercapto-pyrrolidine-1-carboxylic acid butyl ester;
u) (2S,4R)-4-Mercapto-2-(3-phenyl-propionyl)-pyrrolidine-1-carboxylic acid butyl ester;
v) (2S,4S)-1-[4-acetylsufanyl-1-(naphthalene-2-sulfonyl)-pyrrolidine-2-carbonyl]-piperidine-4-carboxylic acid ethyl ester;
w) (2S,4R)-4-[[[[4-Acetylsulfanyl-1-(naphthalene-2-sulfonyl)-pyrrolidine-2-carbonyl]-amino]-acetyl]-methyl-amino]-benzoic acid methyl ester.

These compounds show IC₅₀ values in the radioimmunoassay (E on ECE-inhibition, see below) of about 5 nM to 1000 nM.

A process for the preparation of a compound as defined above comprising the reaction of a compound of formula 1 (Scheme 3)

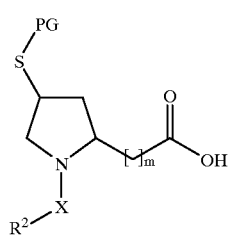

1 wherein $R^2$, X and m are as defined above and PG is a sulfur protecting group, e.g. S-trityl, S-para-methoxybenzyl or S-acetyl, with the amine $HNR^5R^6$, wherein $R^5$ and $R^6$ are as defined above to give a compound of the formula 2 (Scheme 3).

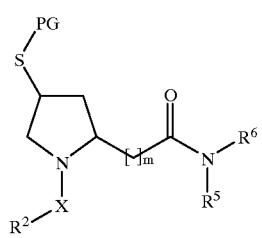

2

The invention also refers to pharmaceutical compositions comprising a compound as defined above and a pharmaceutically acceptable excipient.

A further embodiment of the present invention refers to the use of compounds as defined above as active ingredients in the manufacture of medicaments comprising a compound as defined above for the prophylaxis and treatment of disorders which are caused by endothelin-converting enzyme (ECE) activity especially myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, graft rejection, diseases associated with cytostatic, ophthalmological, and cerebroprotective indications, and organ protection.

Further the invention refers to the use of compounds as described above for the treatment or prophylaxis of diseases which are associated with myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection.

In addition the invention comprises compounds as described above for use as therapeutic active substances, in particular in context with diseases which are associated with zinc hydrolase activity such as myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection.

The invention also comprises a method for the therapeutic and/or prophylactic treatment of myocardial ischaemia, congestive heart failure, arrhythmia, hypertension, pulmonary hypertension, asthma, cerebral vasospasm, subarachnoid haemorrhage, pre-eclampsia, kidney diseases, atherosclerosis, Buerger's disease, Takayasu's arthritis, diabetic complications, lung cancer, prostatic cancer, gastrointestinal disorders, endotoxic shock and septicaemia, and for wound healing and control of menstruation, glaucoma, diseases associated with cytostatic, ophthalmological, and cerebroprotective indications, and organ protection, which method comprises administering a compound as defined above to a human being or animal.

The invention also relates to the use of compounds as defined above for the inhibition of zinc hydrolase activity.

The invention also refers to the above compounds whenever manufactured by a process as described below.

Compounds of formula (I) can be prepared by methods known in the art or as described below. Unless indicated otherwise, the substituents $R^1$, $R^2$, $R^3$, $R^4$, $R^5$, $R^6$, $R^7$, $R^{7a}$ $R^8$, $R^9$, $R^{10}$, $R^{11}$, $R^{12}$, A, m, X and Y are as described above. All starting materials are known or can be prepared by known methods.

The synthesis of the intermediates (acids) for the preparation of compounds of the formula (I) are depicted in Scheme 1. The starting material is commercial available or is synthesized from hydroxyproline by methods known in the art and described for example in "The Practice of Peptide Synthesis", M. Bodanszky and A. Bodanszky, Springer Verlag, Berlin, 1984.

Step a of Scheme 1 describes the persilylation of hydroxy- and amino groups, e.g. by reaction of compound 1 with hexamethyldisilazan at 140° C. followed by reaction with $R^2SO_2Cl$ in THF or conversion to all other $R^2X$ described later or di-t-butyldicarbonate, $NaHCO_3$ in dioxane, $H_2O$ (BOC protection).

For inversion of the configuration (via mesylate) the resulting alcohol 2 is treated with $MeSO_3H$, $Ph_3P$, DIAD or DEAD in toluene (room temperature to 80° C.) or (via bromide) with LiBr, DEAD, $Ph_3P$ in THF (4° C. to room temperature) or (via chloride) with $Ph_3P$, $CCl_4$ in $CH_2Cl_2$ (3° C. to room temperature). In the case of retention of the configuration (via mesylate or tosylate) alcohol 2 can be transformed to a compound of formula 3 by reaction with $MeSO_2Cl$, pyridine, DMAP or TosCl, pyridine, DMAP in $CH_2Cl_2$ (0° C. to room temperature).

For the introduction of a protected thiol moiety, compounds of formula 3 are treated with e.g. triphenyl-methanethiol or 4-methoxybenzylmercaptane and K-Ot-Bu in DMF (for Br: 0° C. to room temperature; for Cl: 0° C.; for Mesylate: room temperature to 100° C.) or with potassium thioacetate in DMF room temperature to 100° C. (step c).

In the case of $X-R^2$=BOC and R=/t-butyl, BOC deprotection can be accomplished with TFA in $CH_2Cl_2$ at -20° C. to room temperature to give an amine. For the introduction of a new $R^2$, the amine may be reacted with $R^2OCOCl/$ pyridine in THF or with (a) $R^2OH/Cl_3COCl/$quinoline (formation of the chloroformate) followed by reaction with $NaH$, in case new $R^2X$ is a carbamate. In case $R^2X$ is a sulfonamide the amine may be treated with $R^2SO_2Cl$, (i-Pr)$_2$EtN, optionally in the presence of catalytic DMAP or DMAP-poly. in $CH_2Cl_2$ at room temperature or in case $R^2X$ is amide the amine may be reacted with with $R^2COOH$, EDCI, DMAP.

Hydrolysis of ester 4 (PG=Acetyl, step d) can be achieved with aqueous lithium hydroxide in THF (0° C. to RT) or sodium hydroxide in ethanol to give acid 5, in the case of t-butyl esters the saponification can be accomplished with TFA in $CH_2Cl_2$.

For the reaction of compound 5 to compound 6 (step e) the Arndt-Eistert reaction may be used. Therefore in the case m=1 the following procedure is used: addition of (COCl)$_2$, cat DMF in $CH_2Cl_2$ at 0° C. to room temperature to give the corresponding acid chloride followed by reaction with trimethylsilyldiazomethane in THF, $CH_3CN$ at 0° C. to room temperature to give the corresponding diazoethanone and rearrangement to the methyl ester with silver benzoate in MeOH, THF at −25° C. to room temperature, followed by ester cleavage with aqueous lithium hydroxide in THF (0° C. to RT) or sodium hydroxide in ethanol to give compound 6. For m=2 compounds of formula 5 can be transformed into the corresponding Weinreb amide (e.g. HCl•HNMeOMe, NMM, EDCI, HOBT) and can be converted to an aldehyde (LAH, −78 to −30° C. in THF). The obtained compound can be converted by a Horner-Emmons reaction (e.g. (EtO)$_2$P(=O)CH$_2$COOEt, NaH in THF) followed by reduction of the double bond (e.g. Mg in MeOH) and saponification of the ester with either aqueous lithium hydroxide in THF (0° C. to RT) or sodium hydroxide to give compound 6.

BOC replacement against other $R^2X$ may follow by BOC-cleavage and treatment of the amine with the reagents described above.

Starting from the S-acetyl protected ester 4, saponification of the ester and the thioester moiety with 0.1M LiOH in THF or 1M NaOH in THF gives the thiol, which is treated with iodine and triethylamine or iPr$_2$NEt in $CH_2Cl_2$ to yield the disulfid-diacid 7 (step f, scheme 1).

SCHEME 1

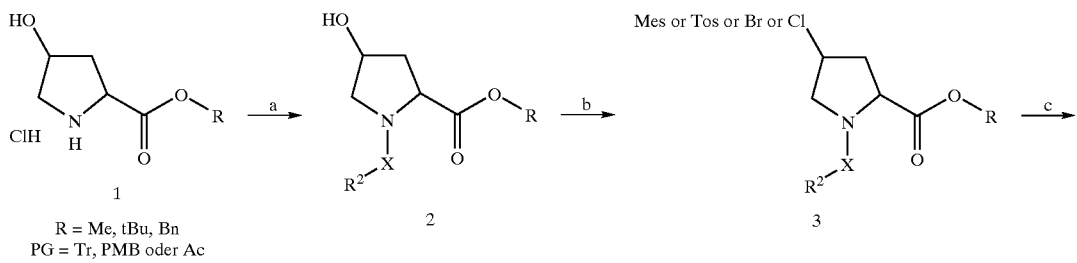

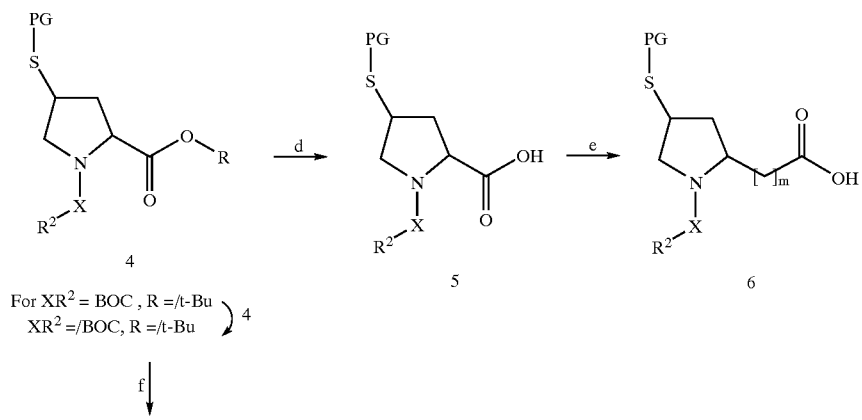

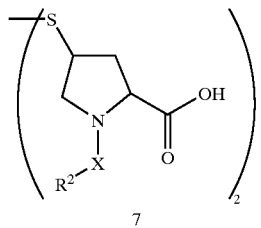

SCHEME 2

PG = Z, BOC

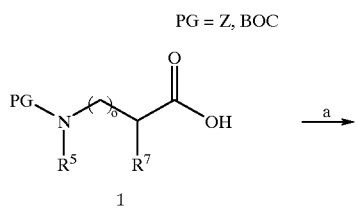

wherein o = 1 for $R^7$ = H
or o = 0 for $R^7$ = /H

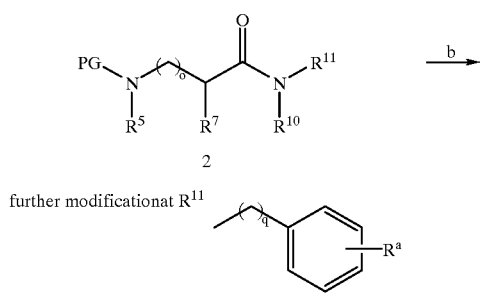

c. for $R^a$: CO₂Me to CH₂OH
eg. d. for $R^a$: CH₂OH to CH₂OMe
e. for $R^a$: CH₂OH to CH₂OTBDMS

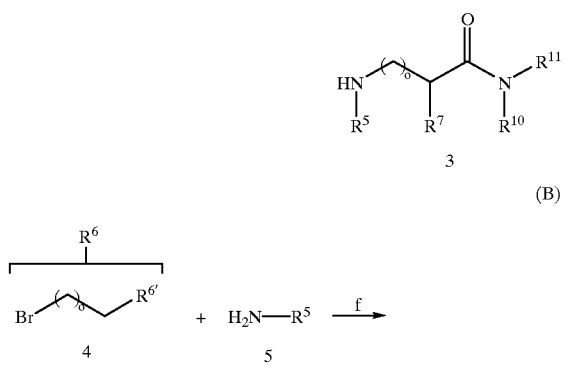

(A)

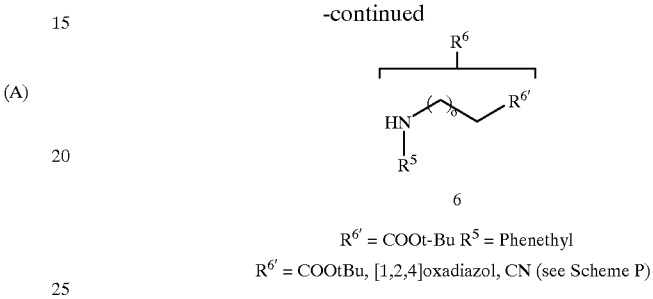

$R^{6'}$ = COOt-Bu $R^5$ = Phenethyl
$R^{6'}$ = COOtBu, [1,2,4]oxadiazol, CN (see Scheme P)

The side chain A can be readily assembled as depicted in Scheme 2a prior to the coupling to the acids which were prepared according to scheme 1. A suitably protected aminoacid is treated with TPTU, 4-Methylmorpholine in CH₂Cl₂ and the approprioate amine NHR¹⁰R¹¹, or with 2-chloro-4,6-dimethoxy-1,3,5-triazine, 4-methyl-morpholine, amine NHR¹⁰R¹¹ and 4-dimethylamino-pyridin in DMF. Alternatively, the amide 2 can be prepared by transferring the acid 1 into the corresponding chloride (e.g. oxalyl chloride in toluene) or into the corresponding mixed anhydride (e.g. isobutyl chloroformate and N-ethylmorpholine in DMF) followed by treatment with the desired amine NHR¹⁰R¹¹ in DMF.

Deprotected amine 3 can be obtained (step b) in the case of BOC-protection by treatment with TFA in CH₂Cl₂ and in the case of Z-protection by hydrogenation (e.g. 10%Pd/C, H₂ in MeOH in the presence of HCl or 10%Pd/C, H₂ in MeOH/NEt₃).

Further modifications of the side chain may be achieved prior to deprotection: An ester moiety at the aromatic ring (R$^a$) may be reduced to the hydroxymethyl group on treatment with lithium borhydride in THF (50° C., 2 h, step c). This maybe protected as a TBDMS ether using TBDMSCl and imidazole in DMF, 12 h, 5° C. to room temperature (step d) or transferred into an ether by treatment with sodium hydride, alkyl iodide in DMF (step e).

Other amines may be prepared using the route outlined in Scheme 2b: namely the alkylation of the amine 4 with the bromo derivative 5 gives the corresponding secondary amine 6 (step f).

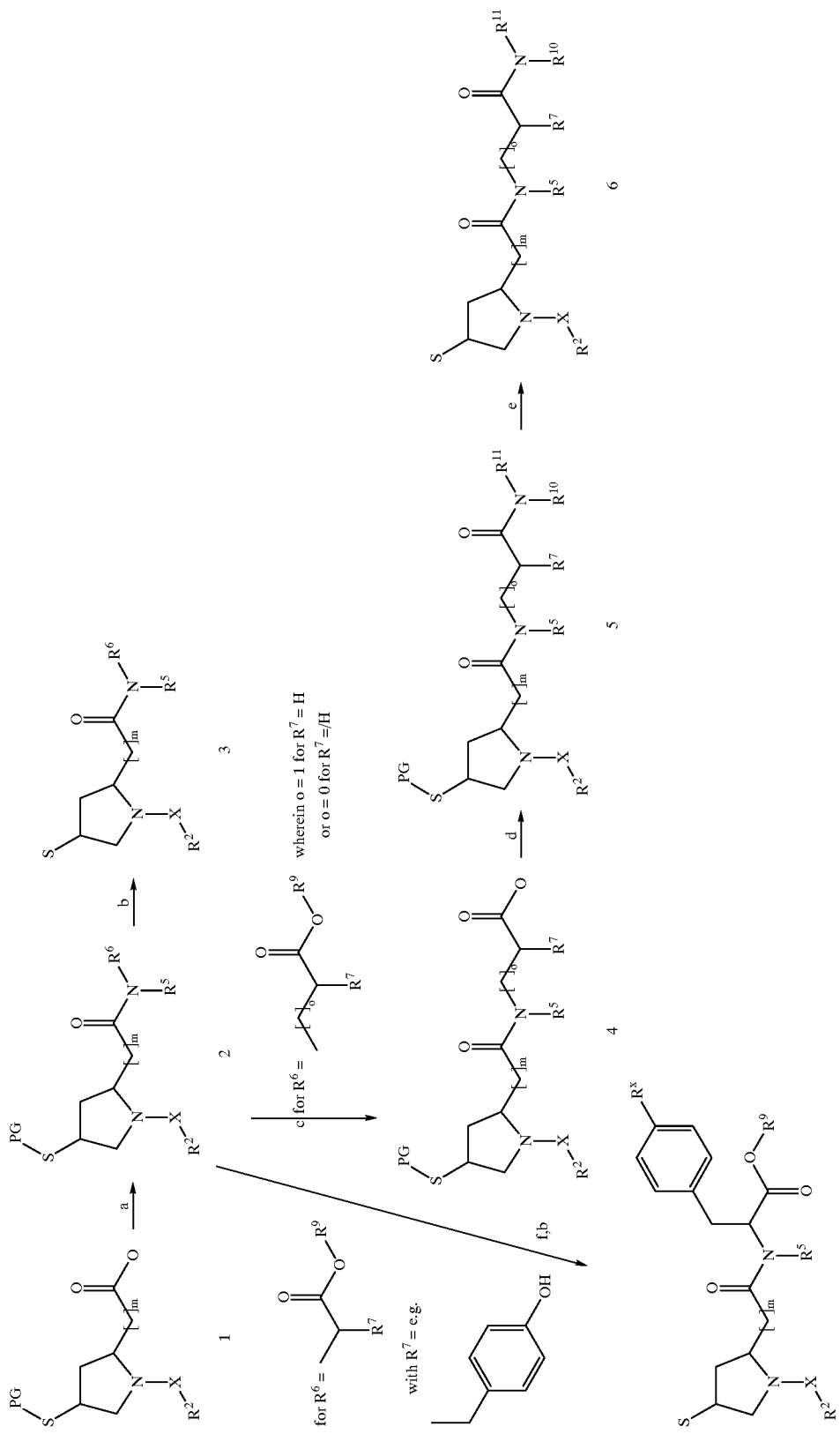

Compounds of the formula (I) can be prepared as depicted in Scheme 3 from the acid 1 and a corresponding amine $NHR^5R^6$. For the synthesis of thio protected amide 2 several methods may be employed: TPTU, NMM or $iPr_2NEt$, $HNR^5R^6$ in $CH_2Cl_2$ or EDCI, HOBT, $HNR^5R^6$ in THF, transformation of the acid into the corresponding chloride (e.g. oxalyl chloride in DMF) or into the corresponding mixed anhydride (e.g. i-propyl—or ethyl chloroformate in DMF) followed by treatment with $HNR^3R^4$ in DMF (step a).

Deprotection of the thio moiety (step b) may be achieved in the case PG is either p-methoxybenzyl or trityl using triethylsilane in TFA, or triisopropylsilane in TFA, for PG is acetyl using lithium hydroxide in THF/water or sodium alkoholates in THF.

In the case PG is the homodimer, disulfide cleavage with tri-n-butylphosphine and water in 2,2,2-tri-fluoroethanol or DTT, 2M aq. $K_2CO_3$ in MeOH, THF gives the thiol compound 3.

In the case of $R^2X$=BOC, the final $R^2X$ can be introduced by BOC deprotection (e.g. TFA, $CH_2Cl_2$ at 0° C. to room temperature) to get the amine which can be further modified.

In case $R^2X$ is a carbamate this amine may be reacted with $R^2OCOCl$, pyridine or $(i-Pr)_2EtN$ in THF or $CH_2Cl_2$ or by reaction with (a) $R^2OH$, $Cl_3COCl$, quinoline (formation of the chloroformate) followed by reaction with NaH. In case $R^2X$ is a sulfonamide the starting compounds may be reacted with $R^2SO_2Cl$, $(i-Pr)_2EtN$, cat DMAP in $Cl_2CH_2$ at room temperature. In case $R^2X$ is urea the starting compounds may be reacted with isocyanate in EtOH at room temperature. In case $R^2X$ is an alkylated urea the starting compounds may be reacted with isocyanate in EtOH at room temperature followed by reaction with the corresponding alkylhalogenide, K-OtBu at 0° C. to room temperature. In case $R^2X$ is an amide, the starting compounds may be reacted with $R^2COOH$, EDCI, DMAP (with anhydride formation, and subsequent addition of the starting amine at-10° C. to room temperature or as alternative with $R^2COOH$/EDCI/DMAP at room temperature. In case $R^2X$ is a sulfamide (for $R^{13}$ is H) the amine may be reacted with sulfamoyl chlorides in dioxane in the presence of an excess of triethylamine. The sulfamoyl chlorides may be synthesized from $R^2NH_2$ and chlorosulfonic acid in $CH_2Cl_2$ at 0° C. to room temperature followed by reaction with $PCl_5$ in toluene at 75° C. Alternatively the sulfamoyl chlorides can be synthesized in acetonitrile with $R^2NH_2$ and sulfuryl chloride at 0° C. to 65° C. In case $R^2X$ is an alkylated sulfamide ($R^{13}$ is not H) the sulfamide $R^2SONH$-may be reacted with NaH, alkyl halide in DMF at 0° C. to room temperature.

In the cases in which $R^6$ contains a cyano moiety treatment with triethyl silane in TFA at 0° C. to room temperature may give reduction to the amide concomitant to the S-PMB-ether cleavage. Selective thio deprotection may be accomplished with triethyl silane in TFA at 0° C. for 15 min. A further modification of the residue at $R^6$ may be the transformation of the cyano moiety into a tetrazole by treatment with sodium azide and ammonium chloride in DMF at 70–120° C. followed by deprotection as described above (e.g. TFA, $Et_3SiH$, reflux).

In the cases in which $R^6$ is of the formula (II) with $R^8$ is $OR^9$, further modifications of the side chain can be achieved by ester saponification using lithium hydroxide in THF followed by amide formation with the amine $HNR^{10}R^{11}$ by one of the methods given before (step c,d, Scheme 3). The compound 5 can be deprotected according to the methods listed above (step e, see step b).

In the cases in which one of the residues $R^7$ or $R^{11}$ contains an ester this can be hydolyzed prior to S-deprotection (for S-PMB or S— Tr ) or for the homodimers using lithium hydroxide in THF or sodium hydroxide in THF.

A further method for the modification of the $R^{11}$ comprises the reduction of an ester to a methylhydroxy group (e.g. with lithium borhydride in THF) or the deprotection of an alcohol moiety according to the methods known in the art (e.g. HF acetonitrile, $CH_2Cl_2$). Optionally this alkohol can be alkylated using e.g. sodium hydride, alkyl halogenides in THF or DMF or tert-Butyl 2,2,2-trichloroacetimidate with triflic acid in $CH_2Cl_2$, c-hexane or $CCl_4$.

The hydroxy moiety of a tyrosine may be further manipulated by treating the compound 2 in case R12Y is a sulfonamide with $R^{12}SO_2Cl$, $(i-Pr)_2EtN$, cat DMAP in $CH_2 Cl_2$ at room temperature, in case $R^{12}Y$ is a carbamate with $R^{12}OCOCl$, pyridine or $(i-Pr)_2EtN$ in THF or $CH_2Cl_2$, in case R 12Y is urea the starting compounds may be reacted with isocyanate in EtOH at room temperature, in case $R^{12}Y$ is an amide, with $R^{12}COOH$, EDCI, DMAP at-10° C. to room temperature, in case $R^{12}Y$ is an ether with reactive alkyl halogenidesor arylalky halogenides. Deprotection of the thio moiety with trietylsilane, TFA for S-PMB and S-Tr or disulfide cleavage with tri-n-butylphosphine and water in 2,2,2-tri-fluoroethanol or DTT, 2M aq. $K_2CO_3$ in MeOH, THF gives compound 7 (steps f, b). Furthermore, compounds of the formula (I) with A is —$CONR^5R^6$ may be prepared as depicted in Scheme 4. The acid 1 can be treated with amine $H_2NR^5$ or $H_2NR^6$, EDCI, HOBT in THF or one of the other methods for amide formation described above followed by deprotection of the thio moiety with triethylsilane in TFA at reflux to give amide 3 (steps a, b). The second substituent may be introduced via alkylation. Therefore amide 2 may be treated with reactive $R^5$-halogenides and sodium hydride in DMF to give after S-Tr or S-PMB deprotection with triethylsilane in TFA amide 4. In the case that $R^6$ contains an ester, α-alkylation leads to a modification of the side chain A (e.g. a. LiHMDS, b. $R^5$—Br in THF). On deprotection the amide 5 can be obtained (steps d, b).

SCHEME 4

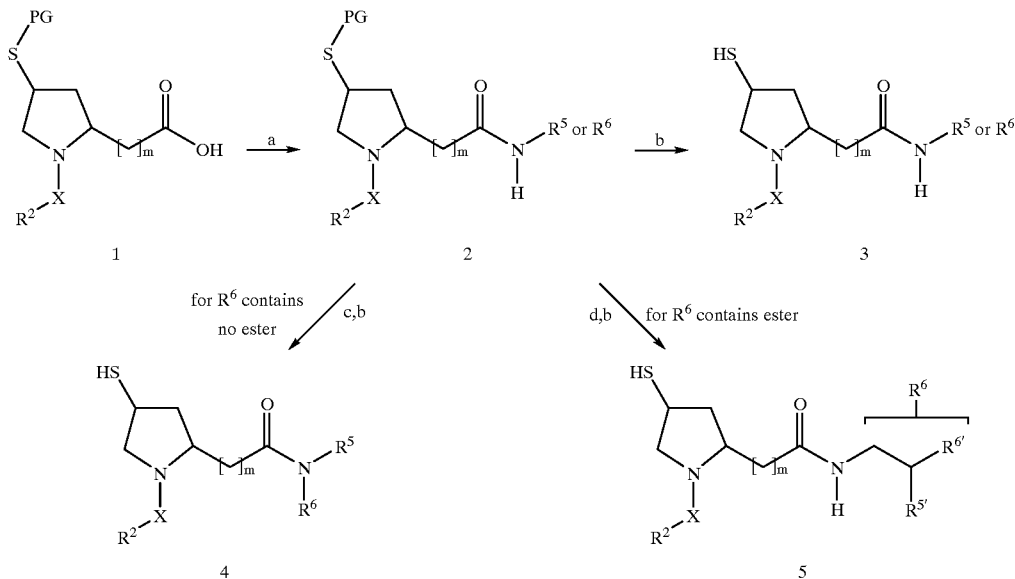

SCHEME 5

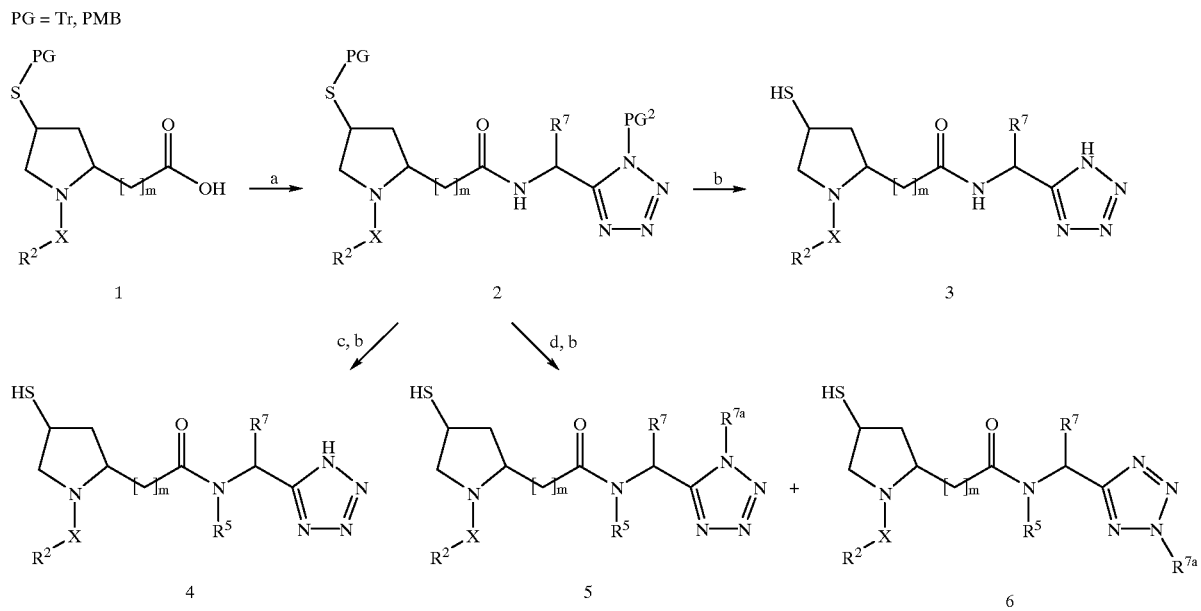

Tetrazole derivatives may be prepared as depicted in Scheme 5. Acid 1 can be transformed into the amide 2 which contains a tetrazole moiety by treatment with an aminotetrazol, HOBT, EDCI in THF, followed by treatment with DBU in $CH_2Cl_2$ or using one of the methods described above (step b). For the synthesis of the tetrazolamino derivative see for example Sephane De Lombaert, Preparation of tetrazolylalkylaminomethylphosphonates as neutral endopeptidase inhibitors. U.S. Pat. No. 5,273,990 A 931228 or S. De Lombaert et al J. Med Chem, 2000, 43, 488–504 and literature sited therein. The tetrazole moiety may be protected before introduction of the side chain (e.g. $PG^2$ is $CH_2CH_2CN$) or by manipulations of the amide 2 (e.g. 4-methoxybenzylchloride, NaI, $Et_3N$ in acetone).

Alkylation of the amide 2 which contains a $PG^2$-protected tetrazole (e.g. sodium hydride, alkyl halogenide in DMF) gives after deprotection of the thio and the tetrazole moieties (e.g. triethylsilane, TFA, 80° C.) the compound 3 (steps c,b).

In the case of the unprotected tetrazole derivative 2 ($PG^2$ is H) alkylation using sodium hydride, alkyl halogenide in DMF may give a mixture of double alkylated regioisomers which can be separated and deprotected (e.g. triethylsilane, TFA, 80° C.) to give compound 5 and 6 (step d,b).

Another method for the modification at the residue $R^2X$ is depicted in Scheme 6.

Treatment of the methylsulfonamide derivative 1 with LDA followed by alkylation with e.g. benzylbromide followed by transformation to the amide 2 by treatment with $NHR^5R^6$, HOBT, EDCI in THF or any other method described above for the amide formation (steps a,b). Dialkylation can be accomplished with LiHMDS, followed by treatment with e.g. benzylbromide followed by transformation to the amide 4. In both cases thiol deprotection may be achieved with triethysilane in TFA.

An alternative synthetic route is depicted in Scheme 7, in which the amide formation is performed prior to the introduction of the thio moiety. Acid 1 is preactivated with TPTU in $CH_2Cl_2$, NMM or by treatment with EDCI, $CH_2Cl_2$, NMM in $CH_2Cl_2$ followed by treatment with the amine $NHR^3R^4$ or by any other amide formation described in the previous schemes.

For inversion of the configuration (via mesylate) the resulting alcohol 2 is treated with $MeSO_3H,/Ph_3P$, DIAD or DEAD in toluene (room temperature to 80° C.) or (via bromide) with LiBr, DEAD, $Ph_3P$ in THF (4° C. to room temperature) or (via chloride) with $Ph_3P$, $CCl_4$ in $CH_2Cl_2$ (3° C. to room temperature). In case of retention of the configuration (via mesylate or tosylate) alcohol 2 can be transformed to a compound of formula 3 by reaction with $MeSO_2Cl$, pyridine, DMAP or TosCl, pyridine, DMAP in $CH_2Cl_2$ (0° C. to room temperature).

Transformation to the corresponding protected thio compound 4 can be achieved e.g. by treatment with potassium thioacetate in DMF.

If further modification of the $R^2X$ moiety is desired, in the case of $R^2X$ is BOC deprotection can be achieved with TFA in $CH_2Cl_2$ followed by further modification of the liberated amine by treatment with the reagents described for reactions in Scheme 1 and 3.

Cleavage of the thioester 4 can be achieved by treatment with 0.1M lithium hydroxide in THF or 1M sodium hydroxide in THF (cleavage of all other ester moieties) or with sodium alkanolate in THF to give compound 5.

SCHEME 6

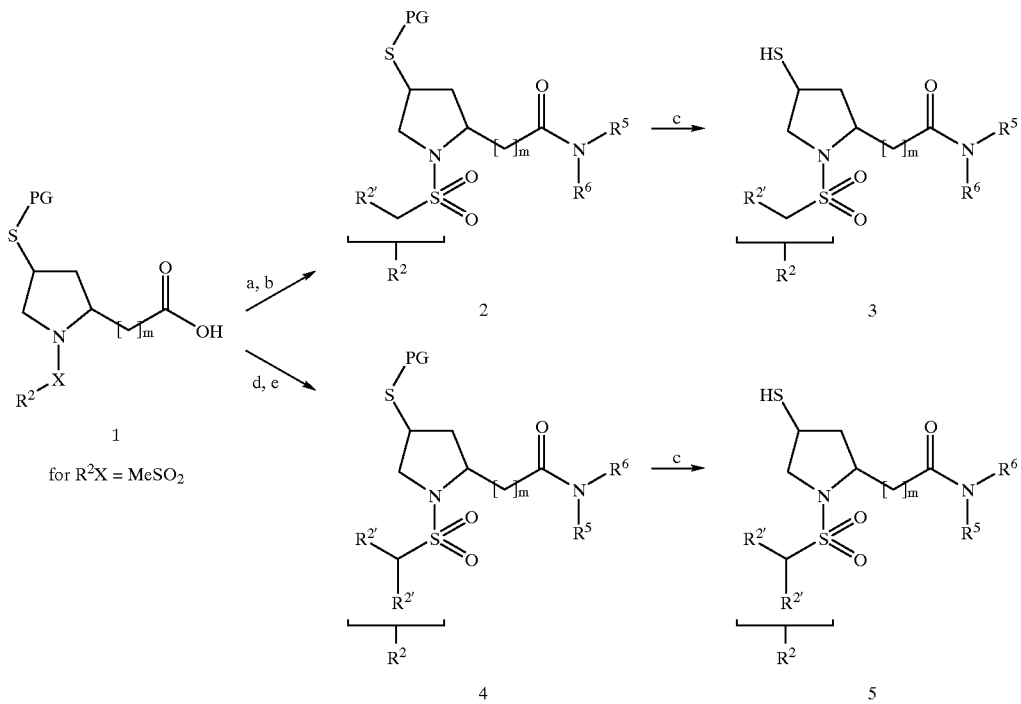

SCHEME 7

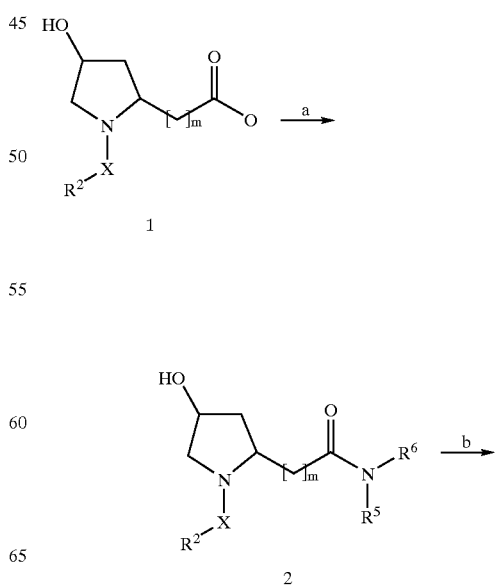

-continued
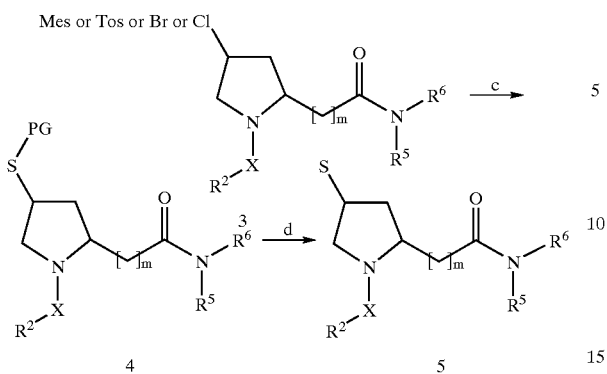
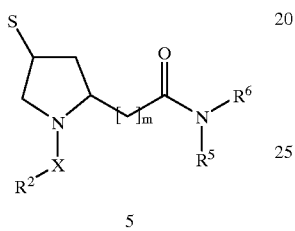
SCHEME 8
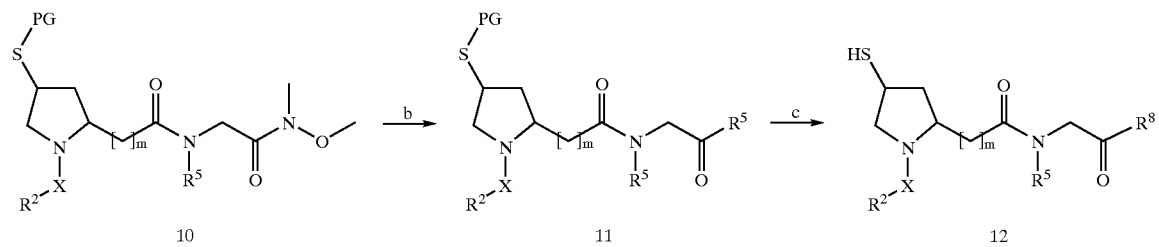
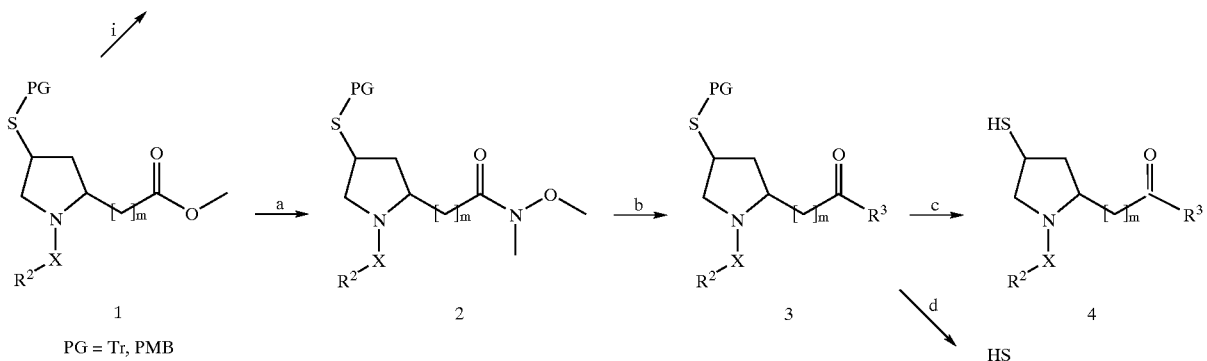
PG = Tr, PMB
PG² = Ac

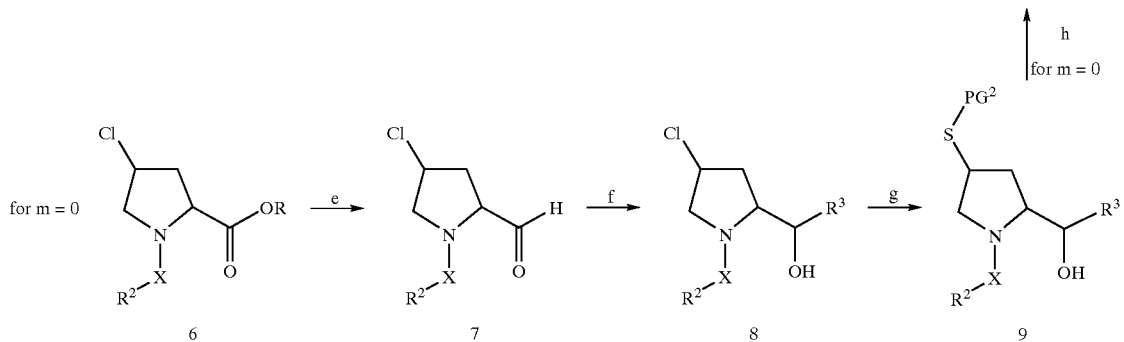

Ketones and alcohols of formula (I, A=—C(O)—$R^3$ or —CH(OH)—$R^4$) may be prepared as depicted in Scheme 8. In the scheme the group $R^3$ also includes the definitions for $R^4$ as mentioned above. The starting acid 1 may be transferred into the Weinreb derivative with NHMeOMe·HCl, Me$_3$Al (excess) in toluene or by pre-activation of acid 1 with TPTU, Huenig's base in DMF at RT followed by reaction with NH(OMe)Me.

In the case of $R^2$X=BOC, the final $R^2$X can be introduced by BOC deprotection (e.g. TFA, CH$_2$Cl$_2$ at 0° C. to room temperature) to get the amine which can be further reacted with one of the reagents described for the compounds in Scheme 1 or 3.

The Weinreb derivative 2 may be treated with metal organic compounds (e.g. $R^3$MgBr in THF or $R^3$Li −25° C. to RT in THF) to give the S-protected ketones 3. Deprotection may be accomplished by oxidation to the corresponding disulfide employing DMSO, Me$_3$SiCl in acetonitril followed by disulfid cleavage with DTT in the presence of potassium carbonate in methanol or with triethylsilane in TFA to give ketone 4. Deprotection and reduction to the alcohols 5 may be achieved using iPr$_3$SiH, TFA in CH$_2$Cl$_2$.

For the synthesis of ketones of the type 12 (steps i, b, c), the acid 1 can be transferred into the corresponding Weinreb derivative 10 by pre-activation with TPTU, Huenig's base in DMF at RT followed by reaction with NHR$^5$CH$_2$NH(OMe)Me. From Weinreb derivative 10 the desired ketones can be prepared by treatment with metal organic compounds (e.g. $R^3$MgBr in THF or $R^3$Li −25° C. to RT in THF) followed by deprotection using triethylsilane in TFA.

Alternatively, the alcohols 5 (for m=0) can be prepared from the ester 6 by selctive reduction to the aldehyde 7 (e.g. di-isobutylaluminium hydride in toluene, THF at −78° C. (step e)) followed by treatment with metal organic compounds (e.g. $R^3$MgBr in THF or $R^3$Li −25° C. to RT in THF, step f) to give alcohol 8 as a mixture of diastereomers. In the case $R^3$ contains a triple bond, this can optionally be reduced (H$_2$/Pd/C in MeOH at 1 atm). For the introduction of the protected thio moiety, compound 8 may be treated with potassium acetate in DMF at 100° C., 2.5 h. After separation of the diastereomers the single compounds are liberated from the S-Ac prodrugs by treatment with 1N LiOH in EtOH (step h).

For the preparation of compounds of formula (I) the reaction pathway of Scheme 9,10-resin synthesis can be followed: the synthesis of the starting material 1 from hydroxyproline is described in Scheme 1. TFA, triisopropyl deprotection at reflux for 30 minutes gives thiol 2 (step a). The final $R^2$X may be introduced either before attachment to the resin or after the preparation of the ketone on the resin (Scheme 10). For the second case, $R^2$X ideally comprises FMOC. This may be prepared from $R^2$X (=BOC) of starting acid 1 by methods known in the art and described for example in "The Practice of Peptide Synthesis", M. Bodanszky and A. Bodanszky, Springer Verlag, Berlin, 1984 to a nonacid labile protecting group (e.g. $R^2$X=FMOC, first selective BOC-deprotection with 40% TFA in CH$_2$Cl$_2$ at RT followed by reaction with Fmoc—OSu in dioxane/water and NaHCO$_3$ as base).

The resin may be prepared as follows (step b, Scheme 9): The linker 4-(α,α-diphenylhydroxymethyl)benzoic acid is activated using TPTU, diisopropylethylamine in DMF and added to benzhydrylamine resin 3. The resin 4 is then treated with thiol 2 in CH$_2$Cl$_2$, TFA to give the resin loaded starting material 5.

The synthesis of final compounds of formula (I) is shown in Scheme 10: The resin linked acid 1 is transformed into the corresponding Weinreb derivative 2 by pre-activation of acid 1 (TPTU, Huenig's base in DMF at RT) followed by reaction with NH(OMe)Me. The compound 2 is treated with metal organic compounds of type R$^5$MX to give the resin bound ketones 3 which can be detached by treatment with TFA, iPr$_3$SiH in CH$_2$Cl$_2$ at RT (step d).

Further modification of $R^2$ can be accomplished in the case of $R^2$X=FMOC before detaching the compound of the resin. Therefore, the FMOC protected compound 2 is treated with 20% piperidine in DMF, followed by introduction of the new $R^2$X by the methods described for synthesis in Schemes 1 and 3.

SCHEME 9
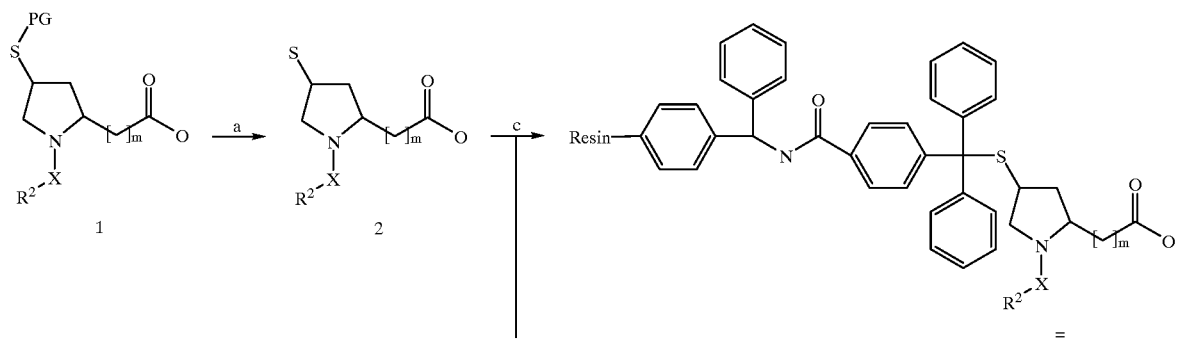
SCHEME 10
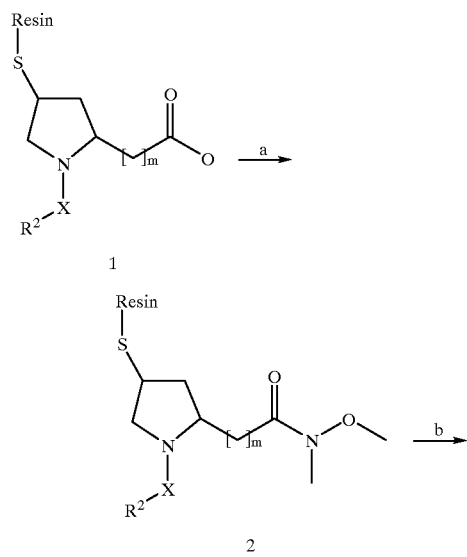

-continued

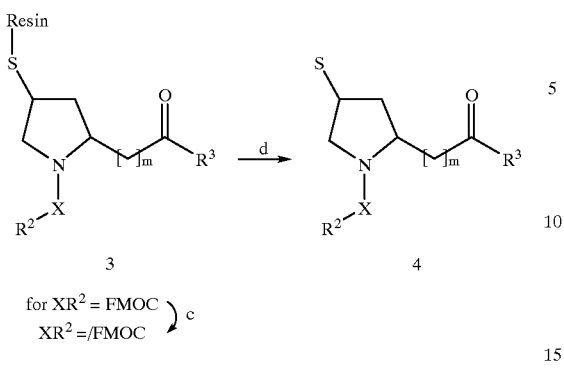

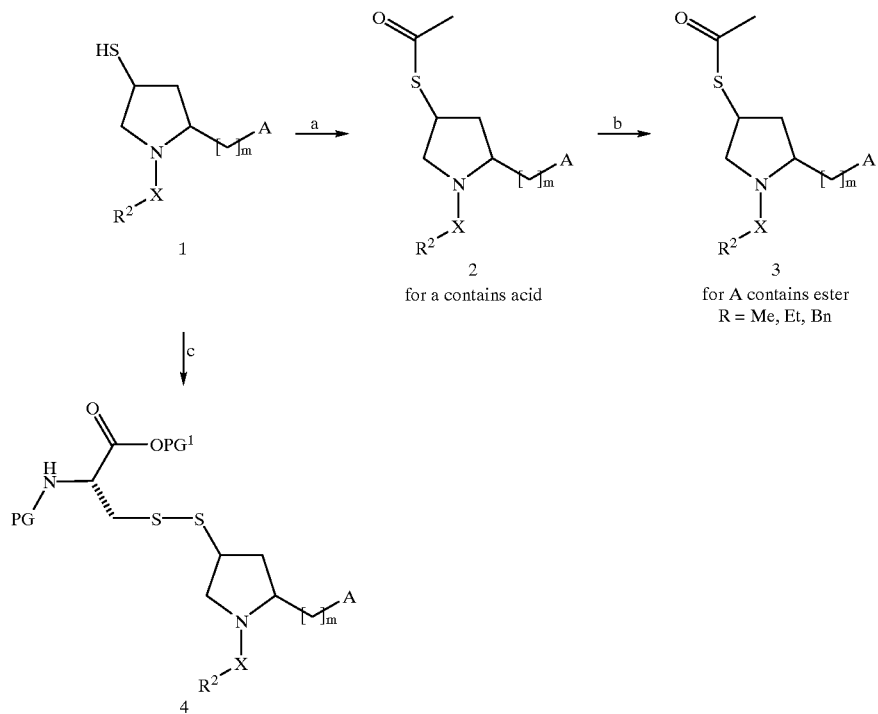

SCHEME 11 for a contains acid for A contains ester
R = Me, Et, Bn

Preparation of prodrugs (Scheme 11) may be accomplished by treating the thiols 1 with the corresponding anhydrides or acid chlorides (e.g. $Ac_2O$/pyridine in $CH_2Cl_2$ at room temperature or AcCl/ pyridine in $CH_2Cl_2$(step a)). If the residue A contains a carboxylic acid moiety this can be transferred into an ester (e.g. alcohol, EDCI, DMAP, $CH_2Cl_2$, step b).

Disulfide derivatives may be prepared by treating the thiol 1 with Ac-Cys(NPys)-OH in DMF as depicted in step c.

On the basis of their capability of inhibiting metalloprotease activity, especially zinc hydrolase activity, the compounds of formula I can be used as medicaments for the treatment and prophylaxis of disorders which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The ability of the compounds of formula (I) to inhibit metalloprotease activity, particularly zinc hydrolase activity, may be demonstrated by a variety of in vitro and in vivo assays known to those of ordinary skill in the art.

A) Cell Culture

A stable human umbilical vein endothelial cell line (ECV304) was cultured in "cell factories" as described until confluency (Schweizer et al. 1997, Biochem. J. 328: 871-878). At confluency cells were detached with a trypsin/EDTA solution and collected by low speed centrifugation.

The cell pellet was washed once with phosphate buffered saline pH 7.0 and stored at −80° C. until use.

B) Solubilization of ECE from ECV304 cells

All procedures were performed at 0–4° C. if not stated otherwise. The cell pellet of $1\times10^9$ cells was suspended in 50 ml of buffer A (20 mM Tris/HCl, pH 7.5 containing 5 mM $MgCl_2$, 100 µM PMSF, 20 µM E64, 20 µM leupeptin) and sonicated. The resulting cell homogenate was centrifuged at 100,000 $g_{av}$ for 60 minutes. The supernatant was discarded and the resulting membrane pellet was homogenized in 50 ml buffer A and centrifugated as described. The washing of the membrane fraction in buffer A was repeated twice. The final membrane preparation was homogenized in 50 ml of buffer B (buffer A+0.5% Tween 20 (v/v), 0.5% CHAPS (w/v), 0.5% Digitonin (w/v)) and stirred at 4° C. for 2 hours. Thereafter the remaining membrane fragments were sedimented as described. The resulting clear supernatant containing the solubilized ECE was stored in 1.0 ml aliquots at −120° C. until use.

C) ECE Assay

The assay measured the production of ET-1 from human big ET-1. To measure high numbers of samples an assay performed in 96 well plates was invented. The enzyme reaction and the radioimmunological detection of the produced ET-1 was performed in the same well, using a specifically developed and optimized coating technique.

D) Coating of Plates

Fluoronunc Maxisorp White (code 437796) 96 well plates were irradiated with 1 joule for 30 minutes in a UV Stratalinker 2400 (Stratagene). The 96 well plates were then fill with 300 µl protein A solution (2 µg/ml in 0.1 M $Na_2CO_3$ pH 9.5) per well and incubated for 48 hours at 4° C. Coated plates can be stored for up to 3 weeks at 4° C. until use.

Before use the protein A solution is discarded and the plates are blocked for 2 hours at 4° C. with 0.5% BSA in 0.1M $Na_2CO_3$, pH 9.5.

Plates were washed with bidestilled water and were ready to perform the ECE assay.

E) Screening Assay

Test compounds are solved and diluted in DMSO. 10 µl of DMSO was placed in the wells, followed by 125 µl of assay buffer (50 mM Tris/HCl, pH 7.0, 1 µM Thiorphan, 0,1% $NaN_3$, 0.1% BSA) containing 200 ng big ET-1. The enzyme reaction was started by the addition of 50 µl of solubilized ECE (diluted in assay buffer 1:30 to 1:60 fold (v/v)). The enzyme reaction was carried out for 30 minutes at 37° C. The enzyme reaction was stopped by addition of 10 µl 150 mM ETDA, pH 7.0.

Radioimmunoassay:

The ET-1 RIA was performed principally as described earlier (Löffler, B. -M. and Maire, J. -P. 1994, Endothelium 1: 273–286). To plates containing the EDTA stopped enzyme reaction mixture 25 µl of assay buffer containing 20000 cpm (3-($^{125}I$)Tyr)-endothelin-1 and 25 µl of the ET specific antiserum AS-3 (dilution in assay buffer 1:1000) was added. Plates were incubated under mixing at 4° C. over night. Thereafter, the liquid phase was sucked with a plate washer and plates were washed once with bidestilled water. To the washed plates 200 µl scintillation cocktail (Microscint 40 LSC-Cocktail, Packard, code 6013641) was added and plates were counted for 2 minutes per well in a Topcount.

Standard curves were prepared in plates with synthetic ET-1 with final concentrations of 0 to 3000 pg ET-1 per well. In all plates controls for maximal ECE activity (in the presence of 10 µl DMSO) and for background production of ET-1 immunoreactivity (in the presence of 10 mM EDTA or 100 µM phosphoramidon) were performed. Assays were run in triplicate.

F) Kinetic Assay

The described assay format could be used to determine the kinetic characteristics of the used ECE preparation as well as different ECE inhibitors (i.e. Km, Ki) by variation of the substrate concentration used in the assay.

G) Cell based ECE Assay

Human ECE-1c was stable expressed in MDCK cells as described (Schweizer et al. 1997, Biochem. J. 328: 871–878). Cells were cultured in 24 well plates to confluency in Dulbecco's modified Eagles's medium (DMEM) supplemented with 10% (v/v) fetal bovine serum (FBS), 0.8 mg/ml geneticin, 100 i.u./ml penicillin and 100 µg/ml streptomycin in a humidified air/$CO_2$ (19:1) atmosphere. Before ECE assay the medium was replaced by 0.5 ml DMEM-HBSS 1:1, 10 mM HEPES pH 7.0 supplemented with 0.1% (w/v) BSA. The inhibitors were added in DMSO at a final concentration of 1%. The enzyme reaction was started by the addition of 0.42 µM human big ET-1 and performed for 1.5 hours at 37° C. in an incubator. At the end of incubation, the incubation medium was quickly removed and aliquots were analysed by radioimmunoassay for produced ET-1 as described above.

The ECE screening assay was validated by the measurement of the characteristic inhibitor constants of phosphoramidon ($IC_{50}$ 0.8±0.2 µM) and CGS 314447 ($IC_{50}$ 20±4 nM) [De Lombaert, Stephane; Stamford, Lisa B.; Blanchard, Louis; Tan, Jenny; Hoyer, Denton; Diefenbacher, Clive G.; Wei, Dongchu; Wallace, Eli M.; Moskal, Michael A.; et al. Potent non-peptidic dual inhibitors of endothelin-converting enzyme and neutral endopeptidase 24.11. Bioorg. Med. Chem. Lett. (1997), 7(8), 1059–1064]. The two inhibitors were measured with $IC_{50}$ values not significantly different from those described in the literature but measured with different assay protocols. In the cell based assay phosphoramidon showed an $IC_{50}$ of 4 µM. This assay gave additional information about the inhibitory potency of inhibitors under much more physiologic conditions, as e.g. the ECE was embedded in a normal plasma membrane environment. It is important to state, that the screening assay was performed in the presence of 1 µM Thiorphan to block any potential big ET-1 degradation due to the action of NEP24.11. No NEP activity was present in MDCK-ECE-1 c transfected cells in preliminary experiments when ET-1 production was measured in presence or absence of thiorphan. In subsequent experiments no thiorphan was added in the incubation medium.

According to the above methods, the compounds of the present invention show $IC_{50}$ values in the radioimmunoassay (E on ECE-inhibition) of about 5 nM to about 1000 µM. The preferred compounds show values of 5 nM to 1000 nM.

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

The pharmaceutical compositions may be administered orally, for example in the form of tablets, coated tablets, dragées, hard or soft gelatin capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragées or hard gelatin capsules the compounds of the present invention may be admixed with pharmaceutically inert, inorganic or organic excipients. Examples of suitable excipients for tablets, dragées or hard gelatin capsules include lactose, maize starch or derivatives thereof, talc or stearic acid or salts thereof.

Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, alcohols, polyols, glycerin, and vegetable oils.

For suppositories, and local or percutaneous application, excipients which may be used include for example natural or hardened oils, waxes, fats and semi-solid or liquid polyols.

The pharmaceutical compositions may also contain preserving agents antioxidants, solubilising agents, stabilizing agents, wetting agents, emulsifiers, sweeteners, colorants, odorants, salts for the variation of osmotic pressure, buffers, coating agents or antioxidants. They may also contain other therapeutically valuable agents.

The dosages in which the compounds of formula I are administered in effective amounts depend on the nature of the specific active ingredient, the age and the requirements of the patient and the mode of application. In general, dosages of 0.1–100 mg/kg body weight per day come into consideration, although the upper limit quoted can be exceeded when this is shown to be indicated.

The following specific examples are provided as a guide to assist in the practice of the invention, and are not intended as a limitation on the scope of the invention.

EXAMPLES

General Remarks and Abbreviations

All reactions were performed under argon.

Abbreviations: aq. aqueous, brine saturated aqueous solution of NaCl, $CH_2Cl_2$ dichloromethane, DBU 1,8-Diazabicyclo[5.4.0]undec-7-ene, DCHA Dicyclohexylamine, DEAD Diethylazodicarboxylate, DIAD Diisopropyl azodicarboxylate, DIEA diisopropyl ethylamine, DMA dimethyl acetamide, DMAP 4-Dimethylaminopyridine, DMF dimethyl formamide, DMSO dimethylsulfoxide, DTT 1,4-Dithio-DL-threitol, EDCI N-(3-Dimethylaminopropyl)-N'-ethylcarbodiimide-hydrochloride, $Et_2O$ diethyl ether, EtOAc ethyl acetate, EtOH ethanol, Fmoc 9-fluorenylmethoxycarbonyl, Fmoc—OSu N-(9H-Fluoren-2-ylmethoxycarbonyloxy)succinimide, hexane hexane, HOBT 1-Hydroxybenzotriazole, LAH Lithium aluminium hydride, LDA lithium diisopropylamide, LiHMDS lithium bis(trimethylsilyl)amide, MeOH methanol, NaH sodium hydride, NaKtartrate sodium potassium tartrate, NEM N-ethylmorpholine, NMM N-methylmorpholine, PMB paramethoxybenzyl, sat. saturated, TBAF tetrabutylammonium fluoride., TBDMSCl tert butyl dimethylsilyl chloride, TFA trifluoro acetic acid, THF tetrahydrofurane, TPTU O-(1,2-dihydro-2-oxo-1-pyridyl)-N,N,N',N'-tetra-methyluronium-tetrafluorborate.

Example 1

General Procedures

1. Amide Formation with Ethyl Chloroformate

To 1 eq of the acid in (10–20 ml/mmol) THF are added 1.1–1.3 eq 4-ethyl morpholine, followed by 1.1–1.3 eq ethyl chloroformate at 0° C.. The suspension is stirred at that temperature for 1 h, before 1.1–1.3 eq amine in THF are added. The mixture is stirred at RT over night, diluted with EtOAc, and water is added. The organic phase is washed with 1M HCl, water, aq. solution of $NaHCO_3$, water, and brine, dried over $Na_2SO_4$, filtered and evaporated. The crude product is purified by flash chromatography.

Amide Formation with TPTU as Reagent

To 1 eq of the acid in (10–20 ml/mmol) $CH_2Cl_2$ are added 1.1 eq 4-methyl morpholine, followed by 1.2 eq TPTU and 1.1 eq of the amine. The solution is stirred at RT until no starting material can be detected. The mixture is concentrated, the residue is dissolved in EtOAc and the organic phase is washed with 1M $KHSO_4$, 5% aq. $NaHCO_3$ solution and brine, dried over $Na_2SO_4$, filtered and evaporated. The crude product is purified by flash chromatography.

Amide Formation with EDCI as Reagent

To 1 eq of the acid in (10–20 ml/mmol) THF are added 2–3 eq 4-methyl morpholine, followed by 0.2 eq HOBT, and 1.2 eq EDCI and 1.1 eq of the amine or amine·HCl. The solution is stirred at RT until no starting material can be detected. The mixture is diluted with EtOAc, the residue is dissolved in EtOAc and the organic phase is washed with 1M $KHSO_4$, 5% aq. $NaHCO_3$ solution and brine, dried over $Na_2SO_4$, filtered and evaporated. The crude product is purified by flash chromatography.

2.1. Preparation of Sulfonamides 1 eq of the amine is treated with (1.5 eq for each $NH_2$) $RSO_2Cl$ in (20–30 ml/mmol amine) $CH_2Cl_2$ in the presence of 0.15–1.5 eq DMAP (optional) at RT until no starting material can be detected with TLC. 1M HCl is added, the inorganic phase is extracted with $CH_2Cl_2$ and the combined organic phases are washed with 1M HCl, brine and dried over $Na_2SO_4$, filtered and evaporated. The crude material is purified by flash chromatography.

2.2. Preparation of Carbonamides 1 eq of the amine is treated with (1.5 eq for each $NH_2$) RCOCl in (20–30 ml/mmol amine) $CH_2Cl_2$ in the presence of 0.15–1.5 eq DMAP (optional) at RT until no starting material can be detected with TLC. 1M HCl is added, the inorganic phase is extracted with $CH_2Cl_2$ and the combined organic phases are washed with 1M HCl, saturated solution of $NaHCO_3$, brine and dried over $Na_2SO_4$, filtered and evaporated. The crude material is purified by flash chromatography.

2.3. Preparation of Ureas 1 eq of the amine·HCl is treated with (2.1 eq for each $NH_2$) R isocyanate in (5–10 ml/mmol amine) $CH_2Cl_2$ in the presence of 5 eq Hünigs base at RT until no starting material can be detected with TLC. 1M $KHSO_4$ is added, the inorganic phase is extracted with $CH_2Cl_2$ and the combined organic phases are washed with brine and dried over $Na_2SO_4$, filtered and evaporated. The crude material is purified by flash chromatography.

3.1. BOC-cleavage 1 eq of the Boc-protected amine is treated with (8–15 ml/mmol BOC-amine) $CH_2Cl_2$: TFA (2:1–10:1) until no starting material can be detected with TLC. The solution is poured into a saturated aqueous solution of $NaHCO_3$, and the inorganic phase is extracted with EtOAc or $CH_2Cl_2$. The combined organic phases are washed with $NaHCO_3$ solution and are dried over $Na_2CO_3$, filtered and evaporated.

3.2. General Method for a Selective BOC-deprotection in the Presence of S-Trityl A solution of 15.1 mmol N-BOC—S-Trityl compound in 30 ml $CH_2Cl_2$ is treated at −20° C. with 34 ml TFA and warmed up to RT over a period of 5.5 h. The reaction is evaporated and treated with sat. aqueous $NaHCO_3$ solution/EtOAc (3×), the organic phase is dried over $Na_2SO_4$ and evaporated to give the free amino-tritylsulfanyl compound.

4.1. Disulfide Cleavage with tri-n-butyphosphine 1 eq of disulfide in (25–30 ml/mmol) 2,2,2-trifluoroethanol is treated with 1.2–1.5 eq tri-n-butylphosphine and (trace) 0.009 eq $H_2O$ at 0° C. until no starting material can be detected with TLC. The solution is evaporated in vacuo and immediately purified by flash chromatography on silica gel.

4.2. Disulfide Cleavage with DTT

To 1 eq of disulfide in (15–30 ml/mmol) MeOH - optional additional (10–15 ml/mmol) THF or (10–15 ml/mmol) acetonitrile —is added a sat. solution of $K_2CO_3$ in MeOH, and 1.1 eq DTT. The solution is stirred at RT until no starting material can be detected, the solution is acidified with 1M aq $KHSO_4$ (pH 2) and the inorganic phase is extracted with EtOAc. The combined organic phases are washed with brine, dried over $Na_2SO_4$, filtered and evaporated. The crude product is purified by crystallization or column chromatography.

4.3. Cleavage of Disulfide and Ester in One-pot

To 1 eq of the diester in (50–60 mmol) THF are added (50–60 ml/mmol) 0.1M LiOH at 0° C. and the solution is stirred at RT until no starting material can be detected. To this solution are added 3 eq DTT. The solution is stirred at RT until no intermediate can be detected, the solution is acidified with 1M aq $KHSO_4$ (pH 2) and the inorganic phase is extracted with EtOAc. The combined organic phases are washed with brine, dried over $Na_2SO_4$, filtered and evaporated. The crude product is purified by crystallization or column chromatography.

5.1. Ester Cleavage with LiOH for Diesters

To 1 eq of the diester in (50–60 ml/mmol) THF are added (50–60 ml/mmol) 0.1M LiOH at 0° C. and the solution is stirred at RT until no starting material can be detected. The solution is diluted with ether, the layers are separated and the inorganic phase is acidified with $KHSO_4$ and extracted with EtOAc. The organic layers are dried over $Na_2SO_4$ and evaporated.

5.2. Ester Cleavage with LiOH for Monoesters

To 1 eq of the ester in (30–60 ml/mmol) THF are added (30–60 ml/mmol) 0.1M LiOH at 0° C. (all solutions are degased with argon for 30 min, prior to the reaction) and the solution is stirred at RT until no starting material can be detected. The solution is diluted with ether, the layers are separated and the inorganic phase is acidified with $KHSO_4$ and extracted with EtOAc. The organic layers are dried over $Na_2SO_4$ and evaporated.

5.3. Cleavage of t-butyl Ester 1 eq of the ester is stirred in a solution of (1–4 ml/mmol) $CH_2Cl_2:CF_3CO_2H$ (1:10-1:2) at RT until no starting material can be detected. The solution is concentrated and the product isolated by standard procedures.

5.4. Ester Cleavage with NaOH

A solution of 5.38 mmol carboxylic acid methyl ester is dissolved in 150 ml EtOH or EtOH/THF (1:1) and treated at RT with 10.8 ml (10.8 mmol) aqueous 1 N NaOH. After 3 h (followed by TLC) the reaction is evaporated and poured into aqueous 10% $KHSO_4$/EtOAc (3×). The organic phases are washed with aqueous 10% NaCl solution and dried over $Na_2SO_4$ to give the carboxylic acid.

6.1. Cleavage of Cbz-group 1 eq of Cbz-protected amine in (10–15 ml/mmol) MeOH and 0.05 eq palladium on charcoal are stirred under 1 atm of hydrogen for 1h. The catalyst is removed by filtration, and the crude product is purified by chromatography or crystallization.

7.1. Cleavage of a S-acetyl-protected Thiol

To 1 eq of the Thioester in (20–40 ml/mmol) THF are added (20–40 ml/mmol) 0.1M LiOH at 0° C. (all solutions are degased with argon for 30 min, prior to the reaction) and the solution is stirred at RT until no starting material can be detected. The solution is diluted with ether, the layers are separated and the inorganic phase is acidified with $KHSO_4$ and extracted with EtOAc. The organic layers are dried over $Na_2SO_4$ and evaporated.

7.2. Cleavage of a S-acetyl-protected Thiol and an Ester

To 1 eq of the Thioester in (45–60 ml/mmol) THF are added (45–60 ml/mmol) (6eq) 0.1M LiOH at 0° C. (all solutions are degased with argon for 30 min, prior to the reaction) and the solution is stirred at RT until no starting material can be detected. The solution is diluted with ether, the layers are separated and the inorganic phase is acidified with $KHSO_4$ and extracted with EtOAc. The organic layers are dried over $Na_2SO_4$ and evaporated.

7.3. Cleavage of a S-acetyl-protected Thiol in the Presence of an ethyl/methyl Ester To 1 eq of the protected compound in (20–30 ml/mmol) ethanol/methanol are added 0.6–0.7M (1.5eq) NaOEt/NaOMe at 0° C. (all solutions are degased with argon for 30 min, prior to the reaction) and the solution is stirred at 0° C. until no starting material can be detected. The solution is diluted with EtOAc/IM $KHSO_4$, the layers are separated and the inorganic phase is extracted with EtOAc, the organic one washed with brine and dried over $Na_2SO_4$ and evaporated.

8.1. General Procedure for the Cleavage of PMB-thioethers

To 1 eq of the PMB thioether in TFA (15–30 ml/mmol) are added 10 eq triethylsilane at RT and the solution is heated to 80° C. for 1 min–2 h or stirred at RT for 2 days, recooled and concentrated in vacuo. Standard workup and purification by flash chromatography yields the corresponding thiols.

9.1. Trityl Deprotection for Single Compounds with Triethylsilane

A solution of 0.58 mmol tritylsulfanyl in 5.8 ml TFA is treated at 0° C. with 0.92 ml (5.78 mmol) triethylsilane and after 10–30 min at RT evaporated and purified by flash chromatography on silicagel or precipitated from Et$_2$O or Et$_2$O/pentane to give the thiol-compound.

9.2.: Trityl deprotection for Single Compounds with Triisopropylsilane

A solution of 2.84 mmol trityl-protected compound in 30 ml CH$_2$Cl$_2$ is treated at 0° C. with 8 ml TFA and 5.82 ml (28 mmol) triisopropylsilane. After 30 min at RT the solution is completely evaporated and the compound precipitated twice from Et$_2$O/pentane or purified by flash chromatography on silicagel to give the thiol.

9.3. Trityl Deprotection for Parallel Synthesis

A solution of 0.32 mmol trityl-protected compound is dissolved in 1.5 ml acetonitril/0.4 ml TFA/0. 1 ml triethylsilane and after 1 night at RT purified by prep HPLC (RP18, CH$_3$CN/H$_2$O 80:20 to 95:5) to give the free thiols.

Example 2

Synthesis of Pyrrolidine-derivatives

2.1. Preparation of Esters 40 g (220 mmol) of L-hydroxyproline methylester·hydrochloride (twice suspended in toluene and evaporated under reduced pressure to remove water) was suspended in 600 ml hexamethyldisilazane and refluxed for 2 h. The solution was evaporated under reduced pressure and dissolved in 100 ml THF. 49.9 g (220 mmol) of 2-naphthalene-sulphonyl chloride in 200 ml of THF were added slowly and stirred for 16 h at RT. 150 ml H$_2$O were added and after 1h the solvents were evaporated. The residue was partitioned between water/EtOAc (3x), the organic phases were washed with 10% NaCl and dried over Na$_2$SO$_4$ to give 60.4 g (82%) of (2S,4R)-4-Hydroxy-1-(naphthalene-2-sulfonyl)-pyrrolidine-2-carboxylic acid methyl ester, MS: 335 (M$^+$).

In analogy the following compound were prepared:
L-hydroxyproline benzylester·hydrochloride and 1-naphthalenesulfonyl chloride gave (2S,4R)-4-Hydroxy-1-(naphthalene-2-sulfonyl)-pyrrolidine-2-carboxylic acid benzyl ester, MS: 411 (MH$^+$);
L-hydroxyproline methylester·hydrochloride and 1-naphthalenesulfonyl chloride gave (2S,4R)-4-Hydroxy-1-(naphthalene-2-sulfonyl)-pyrrolidine-2-carboxylic acid methyl ester, MS: 335 (M);
L-hydroxyproline benzylester·hydrochloride and methanesulfonyl chloride gave (2S,4R)-4-Hydroxy-1-methanesulfonyl-pyrrolidine-2-carboxylic acid benzyl ester, mp 132–133° C., MS: 300 (MH$^+$);
L-hydroxyproline methylester·hydrochloride and methanesulfonyl chloride gave (2S,4R)-4-Hydroxy-1-methanesulfonyl-pyrrolidine-2-carboxylic acid methyl ester, mp 115.5–117° C., MS: 164 (M-COOMe).

(2S,4R)-4-Hydroxy-pyrrolidine-2-carboxylic acid tert-butyl ester* and naphthyl sulfonyl chloride gave (2S,4R)-4-Hydroxy-1-(naphthalene-2-sulfonyl)-pyrrolidine-2-carboxylic acid tert-butyl ester which was directly subjected to the following reactions.

Prepared from Z-Hyp-OtBu according to T. Ken-ichi, S. Hiroyuki Tetrahedron: Asymmetry 1995, 6, 7, 1641–1656.

Via Mesylate:

A biphasic solution of 13.9 ml (215 mmol) methanesulfonic acid, 29.8 ml (215 mmol) triethylamine and 58.7 g (224 mmol) triphenylphosphine in 150 ml toluene was added to a suspension of 60 g (179 mmol) (2S,4R)-4-Hydroxy-1-(naphthalene-2-sulfonyl)-pyrrolidine-2-carboxylic acid methyl ester in 300 ml toluene which was stirred mechanically. After adding 44.9 ml (233 mmol) of diisopropyl azodicaboxylate (exothermic!) the solution was heated for 2.5 h at 80° C. 300 ml water was added at RT and extracted with ethylacetate (3x300 ml). The organic phase was washed with aqueous 10% KHSO$_4$ (2x100 ml), 10% NaCl (2x150 ml), dried over Na$_2$SO$_4$ and evaporated to give 180 g of crude product. Flash chromatography (EtOAc/hexane 1:1) gave 63.7 g (86%) of (4S,2S)-4-Methanesulfonyloxy-1-(naphthalene-2-sulfonyl)-pyrrolidine-2-carboxylic acid methylester.

64.2 g (167 mmol) of triphenylmethanthiol was slowly added at RT to a solution of 17.9 g (160 mmol) of potassium tert-butylate in 300 ml DMF and stirred mechanically for 30 min. Then 63 g (152 mmol) of (4S,2S)-4-Methanesulfonyloxy-1-(naphthalene-2-sulfonyl)-pyrrolidine-2-carboxylic acid methylester in 300 ml DMF were added at 20° C. by cooling at the end with an ice bath. The reaction was heated for 1.3 h at 100° C., cooled, evaporated to 400 ml and extracted with 250 ml aqueous saturated NH$_4$Cl/EtOAc (3x300). The organic phases were washed with aq. 10% NaCl, dried over Na$_2$SO$_4$ and evaporated. Flash chromatography (CH$_2$Cl$_2$/MeOH 99:1) gave 58.6 g (65%, (2S,4R)/(2R,4R)-isomer ca 4:1, $^1$H-NMR) and 9.2 g (10%), (2S,4R)/(2R,4R)-isomer ca 1:1, $^1$H-NMR) of (2S,4R)-1-(Naphthalene-2-sulfonyl)-4-tritylsulfanyl-pyrrolidine-2-carboxylic acid methyl ester, MS: 594 (MH$^+$).

In analogy the following compounds were prepared:
(2S,4R)-4-Hydroxy-1-methanesulfonyl-pyrrolidine-2-carboxylic acid methyl ester gave after 3.75 h at 80° C. (4S,2S)-4-Methanesulfonyloxy-1-(methylsulfonyl)-pyrrolidine-2-carboxylic acid methylester which was heated for 45 min at 100° C. with triphenylmethanthiolate to give (2S,4R)-1-Methanesulfonyl-4-tritylsulfanyl-pyrrolidine-2-carboxylic acid methyl ester (2S,4R)/(2R,4R)-isomer ca 9:1, $^1$H-NMR), MS: 482 (MH$^+$);

(2S,4R)-4-Hydroxy-1-methanesulfonyl-pyrrolidine-2-carboxylic acid benzyl ester gave after 5 h at 80° C. (2S,4S)-1-Methanesulfonyl-4-methanesulfonyloxy-pyrrolidine-2-carboxylic acid benzyl ester which was heated for 30 min with 4-methoxybenzylthiol/potassium tert-butylate to give (2S,4S)-1-Methanesulfonyl-4-methanesulfonyloxy-pyrrolidine-2-carboxylic acid benzyl ester, mp 91–92° C., MS: 453 (MNH$_4^+$).

(2S,4R)-4-Hydroxy-1-(naphthalene-2-sulfonyl)-pyrrolidine-2-carboxylic acid methyl ester gave via (2S,4S)-4-Methanesulfonyloxy-1-(naphthalene-2-sulfonyl)-pyrrolidine-2-carboxylic acid methyl ester which was heated with 4-methoxybenzylthiol/ potassium tert-butylate (2S,4R)-4-(4-methoxy-benzylsulfanyl)-1-naphthalene-2-sulfonyl)-pyrrolidine-2-carboxylic acid methyl ester as colorless oil (Rf 0.4 CH$_2$Cl$_2$:MeOH 9:1), MS: 472 (MH$^+$).

(2S,4R)-4-Hydroxy-pyrrolidine-1,2-dicarboxylic acid 1-tert-butyl ester 2-methyl ester gavevia (2S,4S)-4-Methanesulfonyloxy-pyrrolidine-1,2-dicarboxylic acid 1-tert-butyl ester 2-methyl ester which was heated with potassium thioacetate in DMF (2S,4R)-4-Acetylsulfanyl-pyrrolidine-1,2-dicarboxylic acid 1-tert-butyl ester 2-methyl ester as orange liquid, MS: 303 (MH$^+$).

(2S,4R)-4-Hydroxy-1-(naphthalene-2-sulfonyl)-pyrrolidine-2-carboxylic acid tert-butyl ester via (2S,4S)-4-Methanesulfonyloxy-1-(naphthalene-2-sulfonyl)-pyrrolidine-2-carboxylic acid tert-butyl ester which was treated with potassium thioacetate at 100° C. to give (2S, 4R)-4-Acetylsulfanyl- 1-(naphthalene-2-sulfonyl)- pyrrolidine-2-carboxylic acid tert-butyl ester as light yellow solid, MS: 359 (M-HSCOCH$_3$).

(2S,4R)-4-Hydroxy-pyrrolidine-1,2-dicarboxylic acid 1-benzyl ester 2-tert-butyl ester (Z-Hyp-OtBu*) gave via (2S,4S)-4-Methanesulfonyloxy-pyrrolidine-1,2-dicarboxylic acid 1-benzyl ester 2-tert-butyl ester which was treated with potassium thioacetate in DMF at 100° C. (2S,4R)-4-Acetylsulfanyl-pyrrolidine-1,2-dicarboxylic acid 1-benzyl ester 2-tert-butyl ester.

prepared according to:M. A. Williams, H. Rapoport "Synthesis of Conformationally Constrained DTPA Analogs. Incorporation of the Ethylenediamine Units as Aminopyrrolidines." J. Org. Chem. (1994), 59(13), 3616–25.]

Via Bromide:

To a solution of 76.5 g (291.6 mmol, 6 eq) triphenylphosphine in 650 ml THF were added 44.6 ml (286.8 mmol, 5.9 eq) DEAD in 70 ml THF at a temperature between 1.5–4.5° C. over a period of 0.5 h. The solution was stirred for 0.5 h before 42.2 g (486.1 mmol, 10 eq) LiBr were added, and the reaction mixture was recooled to 4° C. for the addition of 20 g (48.6 mmol) (2S,4R)-4-Hydroxy-1-(naphthalene-2-sulfonyl)-pyrrolidine-2-carboxylic acid benzyl ester in 75 ml THF. After stirring at RT for 3 h, water was added and the suspension concentrated and redissolved in 700 ml EtOAc and water. The layers were separated, the inorganic one was extracted with 100 ml of EtOAc (3x), and the combined organic layers were washed with brine, dried over MgSO$_4$ and evaporated. Triphenylphosphine oxide was removed by crystallization from EtOAc/hexane and the mother liquid was purified by colum chromatography on silica gel with hexane:EtOAc 3:1 yielding 13.4 g (62%) of (2S,4S)-4-Bromo-1-(naphthalene-2-sulfonyl)-pyrrolidine-2-carboxylic acid benzyl ester as colorless solid, mp 97–98° C., MS: 473 (MH$^+$).

3.38 g (30.1 mmol, 1.1 eq) potassium tert. butylate in 150 ml DMF were treated with 4.4 ml (31.5 mmol, 1.15 eq) 4-methoxybenzyl mercaptane at 0° C.. The solution was stirred for 1 h at RT before 12.99 g (27.4 mmol) (2S,4S)-4-Bromo-1-(naphthalene-2-sulfonyl)-pyrrolidine-2-carboxylic acid benzyl ester in 100 ml DMF were added. The reaction was stirred at RT overnight, DMF was removed under vacuum, and the residue redissolved in EtOAc and 1M aq. KHSO$_4$. The layers were separated, and the organic one washed with brine, dried over Na$_2$SO$_4$ and evaporated. The crude oil was purified by flash chromatography on silica gel with hexane/EtOAc (3:1-2:1) as eluent yielding 7.23 g (48%) (2S,4R)-4-(4-Methoxy-benzylsulfanyl)-1-(naphthalene-2-sulfonyl)-pyrrolidine-2-carboxylic acid benzyl ester as light yellow solid, mp 90–91° C., MS: 547 (M$^+$).

In analogy the following compound was prepared:
(2S,4R)-4-Hydroxy-pyrrolidine-1,2-dicarboxylic acid 1-tert-butyl ester 2-methyl ester with 4-methoxybenzylthiol/potassium tert-butylate gave (2S,4R)-4-(4-Methoxy-benzylsulfanyl)-pyrrolidine-1,2-dicarboxylic acid 1-tert-butyl ester 2-methyl ester, MS: 382 (MH$^+$).

Via Chloride:

((2S,4R)-4-Tritylsulfanyl-pyrrolidine-1,2-dicarboxylic acid 1-tert-butyl ester 2-methyl ester: the synthesis of the intermediate of the present invention is known in the art and described for example in International Patent Application WO 9820001 and European Patent Application Publication No. EP-A-696593.)

A solution of 374 g (1.48 mol) (2S,4R)-4-Hydroxy-pyrrolidine-1,2-dicarboxylic acid 1-tert-butyl ester 2-methyl ester in 1.61 CH$_2$Cl$_2$ was treated with 680 g (2.6 mol) triphenylphosphine, cooled to 3–5° C. and treated in 10 min with 1.24l (12.8 mol) CCl$_4$, after 2 h at this temperature cooling was stopped, the reaction temperature was raised to 35° C. over a period of 2 h. It was cooled down to 20° C. and stirred for further 45 min. After addition of 4l of n-heptane, the reaction was evaporated to 2.9l, cooled to 0° C., filtered, the residue was treated twice the same way, the third time by dissolving the residue again in 2 of CH$_2$Cl$_2$. The solvents were evaporated and filtered through silicagel with hexane/tert.-buthyl-methylether 9:1 as eluent. Evaporation of the solvents gave 347 g (89%) of (2S,4S)-4-Chloro-pyrrolidine-1,2-dicarboxylic acid 1-tert-butyl ester 2-methyl ester, MS: 246 (MH$^+$).

A solution of 76 g (0.68 mol) potassium-tert.-butylate in 1.5 l DMF was cooled (−3° C.) and treated slowly (1.5 h) with 202 g (0.73 mol) triphenylmethanethiol in 0.8 l DMF (at max 1° C.). After 2.5 h at 0° C., a solution of 161 g (0.61 mol) of (2S,4S)-4-Chloro-pyrrolidine-1,2-dicarboxylic acid 1-tert-butyl ester 2-methyl ester in 0.35 l DMF was added. The reaction was stirred over night at 2° C., evaporated, dissolved in 1.5 l EtOAc, poured into 2.7 l aqueous saturated NH$_4$Cl solution and extracted with EtOAc (2x). The organic phase was washed with aqueous saturated NaHCO$_3$, dried over Na$_2$SO$_4$ and evaporated. Chromatography on silicagel with hexane/EtOAc (95:5 to 7:3) gave 268 g (87%) (2S,4R)-4-Tritylsulfanyl-pyrrolidine-1,2-dicarboxylic acid 1-tert-butyl ester 2-methyl ester, MS: 504 (MH$^+$).

2.2. Modification of the Substitution Pattern at the Amine Moiety

From (2S,4R)-4-Acetylsulfanyl-pyrrolidine-1,2-dicarboxylic acid 1-tert-butyl ester 2-methyl ester the following esters were prepared by BOC-deprotection according to 3.1. followed by treatment with naphthalene-2-sulfonyl chloride (2.1.), 4-tert-butyl-benzenesulfonyl chloride (2.1.) and naphthalene-2-carbonyl chloride (2.2.), respectively:

(2S,4R)-4-Acetylsulfanyl-1-(naphthalene-2-sulfonyl)-pyrrolidine-2-carboxylic acid methyl ester as white solid, MS: 393 (MH$^+$);

(2S,4R)-4-Acetylsulfanyl-1-(4-tert-butyl-benzenesulfonyl)-pyrrolidine-2-carboxylic acid methyl ester as white solid, MS: 400 (MH$^+$);

(2S,4R)-4-Acetylsulfanyl-1-(naphthalene-2-carbonyl)-pyrrolidine-2-carboxylic acid methyl ester as colorless oil, MS: 358(MH$^+$);

2.3. Preparation of the Acids

A solution of 14.7 g (29.2 mmol) (2S,4R)-4-Tritylsulfanyl-pyrrolidine-1,2-dicarboxylic acid 1-tert-butyl ester 2-methyl ester was dissolved in 660 ml THF/EtOH (1:1) and treated at RT with 58.4 ml (58.4 mmol) aqueous 1 N NaOH. After 2 h the reaction was poured into aqueous 10% KHSO$_4$/EtOAc (3x). The organic phases were washed with aqueous 10% NaCl solution and dried over Na$_2$SO$_4$ to give 14.8 g (quantitativ) of (2S,4R)-4-Tritylsulfanyl-pyrrolidine-1,2-dicarboxylic acid 1-tert-butyl ester. MS: 488 (M-H)$^-$.

In analogy the following compounds were prepared:
(2S,4R)-1-Methanesulfonyl-4-tritylsulfanyl-pyrrolidine-2-carboxylic acid methyl ester gave (2S,4R)-1-Methanesulfonyl-4-tritylsulfanyl-pyrrolidine-2-carboxylic acid, mp 64–69° C., MS: 466 (M-H)$^-$;

(2S,4R)-1-Methanesulfonyl-4-methanesulfonyloxy-pyrrolidine-2-carboxylic acid benzyl ester gave (2S,4R)-1-Methanesulfonyl-4-(4-methoxy-benzylsulfanyl)-pyrrolidine-2-carboxylic acid, MS: 344 (M-H)$^-$;

(2S,4R)-1-(Naphthalene-2-sulfonyl)-4-tritylsulfanyl-pyrrolidine-2-carboxylic acid methyl ester gave (2S,4R)-

1-(Naphthalene-2-sulfonyl)-4-tritylsulfanyl-pyrrolidine-2-carboxylic acid, MS: 578 (M-H)⁻;

(2S,4R)-4-(4-Methoxy-benzylsulfanyl)-1-(naphthalene-2-sulfonyl)-pyrrolidine-2-carboxylic acid benzyl ester gave (2S,4R)-4-(4-Methoxy-benzylsulfanyl)-1-(naphthalene-2-sulfonyl)-pyrrolidine-2-carboxylic acid, MS: 456 (M-H)⁻;

(2S,4R)-4-(4-Methoxy-benzylsulfanyl)-pyrrolidine-1,2-dicarboxylic acid 1-tert-butyl ester 2-methyl ester gave (2S,4R)-4-(4-Methoxy-benzylsulfanyl)-pyrrolidine-1,2-dicarboxylic acid 1-tert-butyl ester, MS: 366 (M-H)⁻.

(2S,4R)-4-(4-Methoxy-benzylsulfanyl)-1-(naphthalene-2-sulfonyl)-pyrrolidine-2-carboxylic acid methyl ester gave (2S,4R)-4-(4-methoxy-benzylsulfanyl)-1-(naphthalene-2-sulfonyl)-pyrrolidine-2-carboxylic acid as colorless solid, MS: 456 (M-H)⁻.

From (2S,4R)-4-Acetylsulfanyl-pyrrolidine-1,2-dicarboxylic acid 1-benzyl ester 2-tert-butyl ester was prepared according to 5.3. (2S,4R)-4-Acetylsulfanyl-pyrrolidine-1,2-dicarboxylic acid 1-benzyl ester as light pink amorphous, MS: 322(M-H)⁻.

Preparation of the acids: Using other methods:
From (2S,4R)-4-Acetylsulfanyl-1-(naphthalene-2-sulfonyl)-pyrrolidine-2-carboxylic acid tert-butyl ester was prepared according to 5.3. (2S,4R)-4-Acetylsulfanyl-1-(naphthalene-2-sulfonyl)-pyrrolidine-2-carboxylic acid as beige solid, MS: 378 (M-H)⁻.

Example 3

Disulfid-diacids

To 1.65 g (2S,4R)-4-Acetylsulfanyl-1-(naphthalene-2-sulfonyl)-pyrrolidine-2-carboxylic acid methyl ester in 220 ml THF were added 220 ml 0.1 N LiOH at 0° C. and the solution was stirred at RT for 1h, concentrated, the inorganic layer was washed with $CH_2Cl_2$, acidified and exracted with EtOAc. The organic layer was washed with brine, dried over $Na_2SO_4$ and evaporated yielding (2S,4R)-4-Mercapto-1-(naphthalene-2-sulfonyl)-pyrrolidine-2-carboxylic acid as white solid, MS: 337 (MH⁺).

To 1.41 g (4.18 mmol) (2S,4R)-4-Mercapto-1-(naphthalene-2-sulfonyl)-pyrrolidine-2-carboxylic acid 1.22 ml (8.8 mmol, 2.2 eq) triethylamine in 20 ml $CH_2Cl_2$ was added a 0.13 M solution of $I_2$ in $CH_2Cl_2$ until no iodide was consumed. The access of iodide was destroyed by the addition of aq. $NaHSO_3$ solution, the phases were separated and the inorganic layer was extracted with $CH_2Cl_2$, the combined organic phases were washed with brine and were dried over $Na_2SO_4$. The residue was triturated with hexane yielding 1.3 g (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid (93%) as light yellow solid, MS: 673 (MH⁺).

Analogously, the following compounds were prepared
from (2S,4R)-4-Acetylsulfanyl-1-(4-tert-butyl-benzenesulfonyl)-pyrrolidine-2-carboxylic acid methyl ester to give (2S,4R)-4-[(3R,5S)-5-carboxy-1-(4-tert-butyl-benzenesulfonyl)-pyrrolidin-3-yldisulfanyl]-1-(4-tert-butyl-benzenesulfonyl)-pyrrolidine-2-carboxylic acid as yellow foam.
from (2S,4R)-4-Acetylsulfanyl-1-(naphthalene-2-carbonyl)-pyrrolidine-2-carboxylic acid methyl ester to give (2S,4R)-4-[(3R,5S)-5-carboxy-1-(naphthalene-2-carbonyl)-pyrrolidin-3-yldisulfanyl]-1-(naphthalene-2-carbonyl)-pyrrolidine-2-carboxylic acid as yellow foam.

Example 4

Other Stereoisomers Derived from L-Hyp-OMe 4.54 g (13.5 mmol) (2S,4R)-4-Hydroxy-1-(naphthalene-2-sulfonyl)-pyrrolidine-2-carboxylicc acid methyl ester in 250 ml $CH_2Cl_2$ were treated with 2.48 g (20.3 mmol, 1.5 eq) DMAP and 3.87 g (20.3 mmol, 1.5 eq) p-toluene sulfonyl chloride at RT for 36 h, poured on 1M $KHSO_4$ and extracted with $CH_2Cl_2$. The organic phase was washed with brine, dried over $Na_2SO_4$ and evaporated. Column chromatography with EtOAc:hexane 1:1 yielded 5.43 g (82%) (2S,4R)-1-(Naphthalene-2-sulfonyl)-4-(toluene-4-sulfonyloxy)-pyrrolidine-2-carboxylic acid methyl ester 16217B112 as white solid.

5.42 g (11 mmol) (2S,4R)-1-(Naphthalene-2-sulfonyl)-4-(toluene-4-sulfonyloxy)-pyrrolidine-2-carboxylic acid methyl ester were suspended in 60 ml DMF and treated with 1.89 g (16.55 mmol, 1.5 eq) potassium thioacetate. The reaction mixture was heated to 100° C. for 45 min, cooled to RT and concentrated. The residue was redissolved in $CH_2Cl_2$/sat. $NaHCO_3$ solution. The inorganic phase was extracted with EtOAc, the organic phases were washed with brine and dried over $Na_2SO_4$. After evaporation the residue was purified by column chromatography yielding 3.6 g (83%) (2S,4S)-4-Acetylsulfanyl-1-(naphthalene-2-sulfonyl)-pyrrolidine-2-carboxylic acid methyl ester as orange oil, MS: 394 (MH⁺).

Analogously, from
(2S,4R)-4-Hydroxy-pyrrolidine-1,2-dicarboxylic acid 1-tert-butyl ester 2-methyl ester was prepared (2S,4S)-4-Acetylsulfanyl-pyrrolidine-1,2-dicarboxylic acid 1-tert-butyl ester 2-methyl ester as orange oil, MS: 304 (MH⁺).

Analogously, to the disulfiddiacid formation described in the previous section the following compounds were prepared:
from (2S,4S)-4-Acetylsulfanyl-1-(naphthalene-2-sulfonyl)-pyrrolidine-2-carboxylic acid methyl ester: (2S,4S)-4-[(3S,5S)-5-Carboxy-1-(naphthalene-2-sulfonyl)-pyrrolidin-3-yldisulfanyl]-1-(naphthalene-2-sulfonyl)-pyrrolidine-2-carboxylic acid as beige solid, MS: 671 (M-H)⁻.
from (2S,4S)-4-Acetylsulfanyl-pyrrolidine-1,2-dicarboxylic acid 1-tert-butyl ester 2-methyl ester: (2S,2'S,4S,4S')-4,4'-Disulfanediyl-bis-pyrrolidine-1,2-dicarboxylic acid 1,1'-di-tert-butyl ester as light yellow solid, MS: 491 (M-H)⁻.

Example 5

Preparation of Extended Esters 5.1. Extended Esters I

Homo-Series [in analogy to J. Podlech, D. Seebach: On the preparation of beta-amino acids from alpha-amino acids using the Arndt-Eistert reaction: scope, limitations and stereoselectivity. Application to carbohydrate peptidation. Stereoselective alpha-alkylations of some beta -amino acids. Liebigs Ann. (1995), Issue 7, 1217–28]

A solution of 25 g (93 mmol) (2S,4R)-1-Methanesulfonyl-4-tritylsulfanyl-pyrrolidine-2-carboxylic acid in 265 ml $CH_2Cl_2$ at 0° C. was treated with 2 drops of DMF followed by 8 ml (99 mmol) oxalylchloride. After 15 min at 0° C. the reaction was stirred 2 h at RT, evaporated and dissolved in 260 ml THF/$CH_3CN$ 1:1. 58.5 ml (117 mmol) 2M trimethylsilyldiazomethane solution in hexane was then added at 0° C.. The reaction was stirred 16h at RT, evaporated and poured in $H_2O$/EtOAc. The organic phase was dried over $Na_2SO_4$, evaporated and purified by flash column chromatography on silicagel with hexane/EtOAc (7:3 to 1:1) to give 12.4 g (48%) of (2S,4R)-2-Diazo-1-(1-methanesulfonyl-4-tritylsulfanyl-pyrrolidin-2-yl)-ethanone, MS: 509 ($MNH_4$+).

In analogy to above, (2S,4R)-1-(Naphthalene-2-sulfonyl)-4-tritylsulfanyl-pyrrolidine-2-carboxylic acid (with 2.3 eq trimethylsilyldiazomethane) gave (2S,4R)-2-Diazo-1-[1-(naphthalene-2-sulfonyl)-4-tritylsulfanyl-pyrrolidin-2-yl]-ethanone in 57% yield, MS: 621 (MNH$_4^+$).

A solution of 12 g (24.4 mmol) (2S,4R)-2-Diazo-1-(1-methanesulfonyl-4-tritylsulfanyl-pyrrolidin-2-yl)-ethanone in 96 ml MeOH/67 ml THF was cooled (−25° C.) and treated in the dark with 0.62 g (2.7 mmol) silver benzoate in 13.9 ml (99.7 mmol) triethylamine. The reaction was warmed to RT and stirred 1 h at RT, evaporated, extracted with H$_2$O/EtOAc and flash column chromatography on silicagel with hexane/EtOAc (7:3) gave 8.7 g (72%) of (2R,4R)-(1-Methanesulfonyl-4-tritylsulfanyl-pyrrolidin-2-yl)-acetic acid methyl ester, MS: 496 (MH$^+$).

In analogy to above, (2S,4R)-2-Diazo-1-[1-(naphthalene-2-sulfonyl)-4-tritylsulfanyl-pyrrolidin-2-yl]-ethanone gave (2R,4R)-[1-(Naphthalene-2-sulfonyl)-4-tritylsulfanyl-pyrrolidin-2-yl]-acetic acid methyl ester in 72% yield, MS: 625 (MNH$_4$+).

5.2. Extended Esters II 30 g (81.6 mmol) (2S,4R)-4-(4-Methoxy-benzylsulfanyl)-pyrrolidine-1,2-dicarboxylic acid 1-tert-butyl ester in 800 ml CH$_2$Cl$_2$ were treated with 62.8 ml (571.2, 7 eq) NMM, 2.19 g (16.24 mmol, 0.2 eq) hydroxybenzotriazole, 37.5 g (195.84 mmol, 2.4 eq) EDCI and 17.5 g (179.52 mmol, 2.2 eq) N,O-dimethylhydroxylamine-hydrochloride. The solution was stirred for 3 h at RT, concentrated and dissolved in 500 ml 1M KHSO$_4$ solution and 500 ml EtOAc were added. The organic layer was separated and washed with brine, dried over Na$_2$SO$_4$ and evaporated. The crude product was purified by flash chromatography on silica gel with EtOAc:hexane 1:1 as eluent yielding 3.6 g (62.4%) (2S,4R)-4-(4-Methoxy-benzylsulfanyl)-2-(methoxy-methyl-carbamoyl)-pyrrolidine-1-carboxylic acid tert-butyl ester as light yellow oil, MS: 411 (MH$^+$).

To 360 ml THF 30.8 ml LiAlH$_4$ solution (30.8 mmol, 1M in THF, 1.2 eq) were added, the solution was cooled to −30° C. and 10.9 g (25.67 mmol) (2S,4R)-4-(4-Methoxy-benzylsulfanyl)-2-(methoxy-methyl-carbamoyl)-pyrrolidine-1-carboxylic acid tert-butyl ester in 100 ml THF were added at that temperature, stirred for 30 min. The solution was cooled to −78° C. and a suspension of silica gel, MgSO$_4$ and 10% KHSO$_4$ solution was added, and slowly warmed to RT. The suspension was filtered, thoroughly washed with THF and evaporated. The crude product was redissolved in CH$_2$Cl$_2$ and dried over Na$_2$SO$_4$ and evaporated yielding 9 g (quant.) (2S,4R)-2-Formyl-4-(4-methoxy-benzylsulfanyl)-pyrrolidine-1-carboxylic acid tert-butyl ester as yellow oil, MS: 351 (M$^+$).

To a solution of 6.2 ml (30.82 mmol, 1.2 eq) triethylphosphono acetate in 80 ml THF were added 1.35 g (30.82 mmol, 1.2 eq, 55%) NaH at −78° C., followed by 9 g (25.68 mmol, 1 eq) (2S,4R)-2-Formyl-4-(4-methoxy-benzylsulfanyl)-pyrrolidine-1-carboxylic acid tert-butyl ester in 50 ml THF. The solution was warmed to RT over night, cooled to 0° C. and 5 ml MeOH were added, followed by 105 ml sat. aq. Sodium potassium tartrate solution and 105 ml 10% NaHCO$_3$ solution. The suspension was filtered, the layers separated and the inorganic ones extracted with EtOAc, the combined organic ones were dried over Na$_2$SO$_4$, filtered and evaporated. The crude product was purified by column chromatograohy on silica gel with hexane:EtOAc (9:1-8:2) yielding 6.21 g (58%) (E)- and/or (Z)-(2S,4R)-2-(2-Ethoxycarbonyl-vinyl)-4-(4-methoxy-benzylsulfanyl)-pyrrolidine-1-carboxylic acid tert-butyl ester as a colorless gum, MS: 422 (MH$^+$).

In analogy to literature [T. Hudlicky, G. Sinai-Zingde, M. G. Natchus, Selective reduction of alpha,beta-unsaturated esters in the presence of olefins. Tetrahedron Lett. (1987), 28(44), 5287-90]:

3.78 g (9 mmol, 1eq) (E)- and/or (Z)-(2S,4R)-2-(2-Ethoxycarbonyl-vinyl)-4-(4-methoxy-benzylsulfanyl)-pyrrolidine-1-carboxylic acid tert-butyl ester in 42 ml MeOH were treated with 1.32 g (54 mmol, 6 eq) magnesium at RT for 5 h. The solvent was evaporated, the crude product dissolved in EtOAc and filtered from the solid particles. This process was repeated, the solvent evaporated yielding 3.67 g (quant) (2R,4R)-4-(4-Methoxy-benzylsulfanyl)-2-(2-methoxycarbonyl-ethyl)-pyrrolidine-1-carboxylic acid tert-butyl ester as colorless oil, MS: 410 (MH$^+$).

To 1.54 g (3.76 mmol, 1 eq) (2R,4R)-4-(4-Methoxy-benzylsulfanyl)-2-(2-methoxycarbonyl-ethyl)-pyrrolidine-1-carboxylic acid tert-butyl ester in 40 ml CH$_2$Cl$_2$ were added 4.32 ml (56.4 mmol, 15 eq) TFA at 0° C. and the solution was stirred at RT for 4 h. The solvent was evaporated and the crude product (2R,4R)-3-[4-(4-Methoxy-benzylsulfanyl)-pyrrolidin-2-yl]-propionic acid methyl ester.trifluoro-acetate was subjected to the following reaction without further purification.

g (0.24 mmol, 1eq) (2R,4R)-3-[4-(4-Methoxy-benzylsulfanyl)-pyrrolidin-2-yl]-propionic acid methyl ester.trifluoro-acetate in CH$_2$Cl$_2$ were treated with 0.1 ml (0.72 mmol, 3 eq) triethylamine and 82 mg (0.36 mmol, 1.5 eq) naphthyl sulfonylchloride at RT for 2 h. Further 0.2 ml (1.44 mmol, 6 eq) triethyl amine were added, and the solution was stirred for additional 2 h. The solution was extracted with 10% NaHCO$_3$ solution and water, dried over Na$_2$SO$_4$ and evaporated. 0.11 g (92%) (2R,4R)-3-[4-(Methoxy-benzylsulfanyl)-1-(naphthalene-2-sulfonyl)-pyrrolidin-2-yl]-propionic acid methyl ester were isolated as yellow oil, MS: 500 (MH$^+$).

Analogously, (2R,4R)-3-[1-Methanesulfonyl-4-(4-methoxy-benzylsulfanyl)-pyrrolidin-2-yl]-propionic acid methyl ester, MS: 388 (MH$^+$), was prepared from (2R,4R)-3-[4-(4-Methoxy-benzylsulfanyl)-pyrrolidin-2-yl]-propionic acid methyl ester-trifluoro-acetate and methylsulfonyl chloride.

Example 6

Preparation of Extended Acids 6.1. Extended Acids I

Following the general method for the hydrolysis of an ester 5.4., (2R,4R)-[1-(Naphthalene-2-sulfonyl)-4-tritylsulfanyl-pyrrolidin-2-yl]-acetic acid methyl ester gave (2R,4R)-[1-(Naphthalene-2-sulfonyl)-4-tritylsulfanyl-pyrrolidin-2-yl]-acetic acid, MS: 592 (M-H)$^−$.

Following the general method for the hydrolysis of an ester 5.4., (2R,4R)-(1-Methanesulfonyl-4-tritylsulfanyl-pyrrolidin-2-yl)-acetic acid methyl ester gave (2R,4R)-(1-Methanesulfonyl-4-tritylsulfanyl-pyrrolidin-2-yl)-acetic acid, MS: 480 (M-H)$^−$.

6.2. Extended Acids II 185 mg (0.37 mmol, 1eq) (2R,4R)-3-[4-(4-Methoxy-benzylsulfanyl)-1-(naphthalene-2-sulfonyl)-pyrrolidin-2-yl]-propionic acid methyl ester in 5 ml EtOH were treated with 1.85 ml 1M NaOH (1.85 mmol, 5 eq) for 2 h at RT, the pH was adjusted to 7 by the addition of 1M HCl, the solvent was evaporated and the crude product redissolved in EtOH and filtered from solids and evaporated, yielding 170 mg (94%) (2R,4R)-3-[4-(4-Methoxy-benzylsulfanyl)-1-(naphthalene-2-sulfonyl)-pyrrolidin-2-yl]-propionic acid as brown gum, MS: 486 (MH$^+$).

Analogously, (2R,4R)-3-[1-Methanesulfonyl-4-(4-methoxy-benzylsulfanyl)-pyrrolidin-2-yl]-propionic acid, MS: 374 (MH$^+$), was prepared from (2R,4R)-3-[1-Methanesulfonyl-4-(4-methoxy-benzylsulfanyl)-pyrrolidin-2-yl]-propionic acid methyl ester.

Example 7

Preparation of the Side Chains 7.1. Compounds Derived from Z-Sar:

Under argon 18.03 g (80 mmol) Z-Sar-OH and 11.3 ml (88 mmol, 1.1 eq) N-ethyl morpholine in 400 ml DMF were treated with 11.75 ml (88 mmol) isobutyl chloroformate at 3° C. and stirred for 2 h. 12.81 g (76 mmol, 0.96 eq) methyl (4-methylamino) benzoate in 100 ml DMF were added slowly and the solution was stirred over night at RT. The solvent was evaporated and the residue redissolved in 200 ml water and 250 ml EtOAc. The inorganic layer was extracted with 300 ml EtOAc (2×), the combined organic layers were washed with 150 ml of lN KHSO$_4$ (2×), 200 ml of water (2×), 200 ml of diluted NaHCO$_3$-solution (2×), 200 ml of water and dried over MgSO$_4$, filtered and evaporated. Purification by flash chromatography on silica gel using a gradient of hexane:EtOAc (4:1-1:2) yielded 24.54 g (83%) of 4-[[(Benzyloxycarbonyl-methyl-amino)-acetyl]-methyl-amino]-benzoic acid methyl ester as yellow oil, which was deprotected according to 6.1. to give 4-(methyl-methylaminoacetyl-amino)-benzoic acid methyl ester, MS: 237 (MH$^+$).

Analogously, from Z-Sar-OH and methyl N-methyl was prepared 2-[[(Benzyloxycarbonyl-methyl-amino)-acetyl]-methyl-amino]-benzoic acid methyl ester as light yellow oil (Rf 0.3 hexane:EtOAc1:2), MS: 370 (M), which was deprotected according to 6.1. and transferred into its HCl.salt by treatment with HCl/MeOH to give 2-(Methyl-methylaminoacetyl-amino)-benzoic acid methyl ester·hydrochloride, MS: 237 (MH$^+$).

Under argon 15.784 g (70 mmol) Z-Sar-OH and 13.52 g (77 mmol, 1.1 eq) 2-chloro-4,6-dimethoxy-1,3,5-triazine in 400 ml DMF were treated with 7.95 g (77 mmol, 1.1 eq) N-methyl morpholine at 0° C. and stirred for 2 h. 12.26 g (73.5 mmol, 1.05 eq) ethyl 4-amino benzoate in 100 ml DMF were added, followed by 3.41 g (28 mmol, 0.40 eq) DMAP and warmed to RT. The mixture was stirred over night, the solvent evaporated, the residue dissolved in 200 ml of water and 250 ml CH$_2$Cl$_2$. The aqueous layer was extracted with 250 ml CH$_2$Cl$_2$ (2×), the combined organic layers were washed with water and dried over MgSO$_4$, filtered and evaporated. Flash chromatography on silica gel with a gradient hexane/EtOAc (4:1-1:1-EtOAc) yielded 21.69 g (83.7%) of 4-[2-(Benzyloxycarbonyl-methyl-amino)-acetylamino]-benzoic acid ethyl ester as a light yellow solid, which was deprotected according to 6.1. to give 4-(2-Methylamino-acetylamino)-benzoic acid ethyl ester as off white syrup, MS: 237 (MH$^+$).

Analogously, the following compounds were prepared:
from Z-Sar-OH and ethyl 3-amino benzoate via 3-[2-(Benzyloxycarbonyl-methyl-amino)-acetylamino]-benzoic acid ethyl ester, white solid (Rf 0.4 hexane:EtOAcl:2), MS: 371 (MH$^+$), followed by deprotection according to 6.1. and treatment with HCl/MeOH to give 3-(2-Methylamino-acetylamino)-benzoic acid ethyl ester·hydrochloride (1:1) as a white solid (Rf 0.05; EtOAc), MS: 236 (M);

from Z-Sar-OH and methyl anthranilate followed by deprotection according to 6.1. and treatment with HCl/ MeOH to give 2-(2-Methylamino-acetylamino)-benzoic acid methyl ester·hydrochloride (1:1) as white crystals (Rf 0.1; EtOAc), MS: 222 (M).

Further manipulation of the side chain intermediates results in the following compounds:

7.2. Alkylation at the Nitrogen

Under argon 2.6 g (7.02 mmol) 3-[2-(Benzyloxycarbonyl-methyl-amino)-acetylamino]-benzoic acid ethyl ester in 80 ml DMF were treated with 1.13 g (25.97 mmol, 3.7 eq) NaH (55% Disp), followed by 7.34 ml (116.5 mmol) methyl iodide. The suspension was stirred at RT over night, added to ice water and extracted with 100 ml of CH$_2$Cl$_2$ (3×). The combined organic layers were washed with water, dried over MgSO$_4$, filtered and evaporated. The residue was purified by flash chromatography on silica gel with a gradient of hexane/EtOAc (9:1-3:2) yielding 1.61 g (59%) of 3-[[(Benzyloxycarbonyl-methyl-amino)-acetyl]-methyl-amino]-benzoic acid ethyl ester as a yellow oil (Rf 0.4 hexane:EtOAcl:2), MS: 384 (M), which was deprotected according to 6.1. and was treated with HCl:MeOH to give 3-(Methyl-methylaminoacetyl-amino)-benzoic acid ethyl ester·hydrochloride (1:1) as white crystals (Rf 0.1; EtOAc), MS: 250 (M).

7.3. Reduction

Under argon 742.7 mg (32.4 mmol, 1.5 eq) lithium borhydride in 35 ml THF were added dropwise to 8 g (21.6 mmol) 4-[[(Benzyloxycarbonyl-methyl-amino)-acetyl]-methyl-amino]-benzoic acid methyl ester in 100 ml THF at RT. The suspension was stirred at RT over night, heated to 50° C. for 3.25 h, recooled to RT and 21 ml MeOH were added slowly. The solution was added to ice water, extracted with ether (3×), the combined organic layers were washed with water, dried over MgSO$_4$, filtered and evaporated. The crude product was purified by flash chromatography on silica gel with a gradient of CH$_2$Cl$_2$/MeOH (100:0-99.9:0.1) yielding 3.9 g (52%) {[(4-Hydroxymethyl-phenyl)-methyl-carbamoyl]-methyl}-methyl-carbamic acid benzyl ester as yellow oil (Rf 0.4 CH$_2$Cl$_2$:MeOH 9:1), MS: 343 (MH$^+$).

7.4. O-Silylprotection or ether formation

Under argon 2.4 g (7.0 mmol) [[(4-Hydroxymethyl-phenyl)-methyl-carbamoyl]-methyl]-methyl-carbamic acid benzyl ester and 1.2 g (7.7 mmol, 1.1 eq) TBDMSCl were dissolved in 35 ml DMF, cooled to 5° C. and 2.4 g (35.0 mmol, 5.0 eq) imidazole were added in small portions. The solution was stirred at RT over night, further 435.7 mg (2.8 mmol, 0.4 eq) TBDMSCl were added, and stirred for additional 4 h. The solution was added to ice water, the layers were separated, the inorganic one was extracted with 50 ml CH$_2$Cl$_2$ (3×), the combined organic layers were washed with water(2×), dried over MgSO$_4$, filtered and evaporated. Purification with flash chromatography on silica gel with with a gradient of CH$_2$Cl$_2$/MeOH (100:0-95:5) afforded 2.25 g (70%) of [[[4-(tert-Butyl-dimethyl-silanyloxymethyl)-phenyl]-methyl-carbamoyl]-methyl]-methyl-carbamic acid benzyl ester as a yellow oil (Rf 0.8

$CH_2Cl_2$:MeOH 9:1), MS: 457 (MH$^+$), which was deprotected according to 6.1. to give N-[4-(tert-Butyl-dimethyl-silanyloxymethyl)-phenyl]-N-methyl-2-methylamino-acetamide as brown oil (Rf 0.3 $CH_2Cl_2$:MeOH 9:1), MS: 323 (MH$^+$).

Under argon to 1.23 g (3.6 mmol) [[(4-Hydroxymethyl-phenyl)-methyl-carbamoyl]-methyl]-methyl-carbamic acid benzyl ester in 40 ml DMF were added 580 mg (13.3 mmol, 3.7 eq, 55% disp) sodium hydride, followed by 3.8 ml (59.6 mmol, 16.6 eq) methyl iodide. The suspension was stirred at RT over night, and added to ice water. The layers were separated and the inorganic one was extracted with 50 ml $CH_2Cl_2$ (3×). The combined organic layers were washed with water (2×), dried over $MgSO_4$, filtered and evaporated. Column chromatography on silica gel with a gradient of $CH_2Cl_2$/MeOH (100:0-98:2) afforded 0.984 g (77%) [[(4-Methoxymethyl-phenyl)-methyl-carbamoyl]-methyl]-methyl-carbamic acid benzyl ester as a light yellow oil (Rf 0.07 $CH_2Cl_2$:MeOH 9:1), MS: 356 (M), +), which was deprotected according to 6.1. to give N-(4-Methoxymethyl-phenyl)-N-methyl-2-methylamino-acetamide as yellow oil (Rf 0.2 $CH_2Cl_2$:MeOH 9:1), MS: 223 (MH$^+$).

7.5. Compounds Derived from BOC-glycine and Z-beta-Ala-OH and other Z-protected aminoacids Under argon 1.5 g (8.56 mmol) BOC-glycine in 210 ml $CH_2Cl_2$ were treated with 1.07 ml (9.42 mmol, 1.1 eq) 4-methyl morpholine, 3.08 g (10.27 mmol, 1.2 eq) TPTU and 1.59 g (9.42 mmol, 1.1 eq) ethyl 4-amino benzoate. The solution was stirred at RT over night and was concentrated. The residue was purified by flash chromatography on silica gel with a gradient of EtOAc/hexane (1:2–2:1) affording 3.28 g 4-(2-tert-Butoxycarbonylamino-acetylamino)-benzoic acid ethyl ester as light brown crystals which were subjected to BOC-cleavage according to 3.1. to give 4-(2-Amino-acetylamino)-benzoic acid ethyl ester as a white solid (Rf 0.1 $CH_2Cl_2$:MeOH 9:1), MS: 222 (MH$^+$).

Analogously the following compounds were prepared from:

BOC-glycine and methyl-4-methylaminobenzoate according to 1.2., followed by BOC-cleavage 3.1. to give 4-(Aminoacetyl-methyl-amino)-benzoic acid methyl ester as an orange gum (Rf 0.1 $CH_2Cl_2$:MeOH 9:1), MS: 222 (MH$^+$).

Z-beta-Ala-OH and ethyl-4-aminobenzoate according to 1.2., followed by deprotection according to 6.1. to give 4-(3-Amino-propionylamino)-benzoic acid ethyl ester, MS: 236 (M).

Z-Asp(OtBu)OH and N-Benzylmethylamine according to 1.2., followed by deprotection according to 6.1. and treatment with HCl/tBuOH, MeOH to give (S)-3-Amino-N-benzyl-N-methyl-succinamic acid tert-butyl ester-HCl, MS: 293 (MH$^+$).

Z-Asp(OtBu)OH and 4-Isopropylaniline according to 1.2., followed by deprotection according to 6.1. and treatment with HCl/MeOH to give (S)-3-Amino-N-(4-isopropyl-phenyl)-succinamic acid tert-butyl ester.HCl, MS: 307 (MH$^+$).

Z-N-Me-Asp(OtBu)—OH DCHA salt (1:1) and N-Benzylmethylamine according to 1.2., followed by deprotection (6.1.) and treatment with HCl/MeOH to give (S)-N-Benzyl-N-methyl-3-methylamino-succinamic acid tert-butyl ester-HCl, MS: 307 (MH$^+$)

Z-N-Me-Asp(OtBu)—OH DCHA salt (1:1) and 4-Isopropylaniline according to 1.2., followed by deprotection (6.1.) and treatment with HCl/MeOH to give (S)-N-(4-Isopropyl-phenyl)-3-methylamino-succinamic acid tert-butyl ester-HCl, MS: 321 (MH$^+$).

Z-MeAla-OH and N-Benzylmethylamine according to 1.2., followed by deprotection (6.1.) and treatment with HCl/MeOH to give (S)-N-Benzyl-N-methyl-2-methylamino-propionamide-HCl, MS: 206 (M).

7.6. Sidechains from Esters of γ-Bromo-alkanoic Acids

A solution of 12.6 ml (100 mmol) phenethylamine in 50 ml toluene was treated at RT with 7.4 ml (200 mmol) tert-butyl bromoacetate and heated at 95° C. for 4 h. After cooling (0° C.), filtration and evaporation of the filtrate, the residue was suspended in pentane, cooled (0° C.), filtrated and evaporated to give 11.5 g (98%) of phenethylamino-acetic acid tert-butyl ester as an oil, MS: 236 (MH$^+$).

The oil had the primary amine (phenethylamine) as by-product which resulted in the corresponding side-product, which could be separated after the EDCI-coupling.

In Analogy:

3-Phenyl-1-propylamine gave (3-Phenyl-propylamino)-acetic acid tert-butyl ester, MS: 249 (M);

Tryptamine gave [2-($^1$H-Indol-3-yl)-ethylamino]-acetic acid tert-butyl ester, MS: 274 (M);

2-Fluorophenethylamine gave [2-(2-Fluoro-phenyl)-ethylamino]-acetic acid tert-butyl ester, MS: 254 (MH$^+$);

4-Fluorophenethylamine gave [2-(4-Fluoro-phenyl)-ethylamino]-acetic acid tert-butyl ester, MS: 254 (MH$^+$);

3-Fluorophenethylamine gave [2-(3-Fluoro-phenyl)-ethylamino]-acetic acid tert-butyl ester, MS: 198 (MH$^+$-isobutene);

4-Methylphenethylamine gave (2-p-Tolyl-ethylamino)-acetic acid tert-butyl ester, MS: 250 (MH$^+$);

1-Amino-3-methylbutane gave (3-Methyl-butylamino)-acetic acid tert-butyl ester, MS: 146 (MH$^+$- isobutene).

28 g (138 mmol) N,N-dimethylformamide di-tert-butyl acetal was slowly added during 50 min to a solution of 5.3 g (34.5 mmol) 3-bromo-propionic acid in 50 ml toluene. The reaction was heated for further 30 min, cooled and extracted with $H_2O$/toluene (2×), aqueous saturated $NaHCO_3$ and aqueous saturated NaCl. The organic phase was dried over $Na_2SO_4$ and carefully (low boiling point of the product) evaporated to give 5.8 g (80%) of 3-bromo-propionic acid tert butylester [U. Widmer, A convenient preparation of tert-butyl esters. Synthesis (1983), Issue 2, 135–6].

In analogy to the general synthesis of the amines, 3-bromo-propionic acid tert butylester and:

Phenethylamine gave 3-Phenethylamino-propionic acid tert-butyl ester, MS: 250 (MH$^+$); 3-Phenyl-1-propylamine gave 3-(3-Phenyl-propylamino)-propionic acid tert-butyl ester, MS: 264 (MH$^+$);

2-Fluorobenzylamine gave 3-(2-Fluoro-benzylamino)-propionic acid tert-butyl ester, MS: 253 (M);

2,4,5-Trifluorobenzylamine gave 3-(2,4,5-Trifluoro-benzylamino)-propionic acid tert butyl ester, MS: 290 (MH$^+$);

2,5-Difluorobenzylamine gave 3-(2,5-Difluoro-benzylamino)-propionic acid tert-butyl ester, MS: 271 (M);

In analogy to the general synthesis of the amines, 3-(chloromethyl)-1,2,4-oxadiazole and 1-amino-3-methylbutane and NaI in toluene gave (3-Methyl-butyl)-[1,2,4]oxadiazol-3-ylmethyl-amine (3-Methyl-butyl)-[1,2,4] oxadiazol-3-ylmethyl-amine, MS: 170 (MH$^+$).

A solution of 9.55 g (48.6 mmol) 2-chloro-1,1,1-triethoxyethane and 3.9 ml (30 mmol) 4-methoxybenzylamine were heated at 40° C. for 15 min. Then a solution of 2.92 g (45 mmol) sodium azide in 60 ml acetic acid was added at RT and heated at 60° C. over night, 20h at 80° C. and 1h at 100° C. The reaction was neutralized with aqueous and solid NaHCO$_3$/EtOAc (3×), washed with aqueous 10% NaCl. The organic phase was dried over Na$_2$SO$_4$, evaporated and purified by flash-chromatography on silicagel (hexane/EtOAc 1:1) to give 3.36 g (47%) 5-Chloromethyl-1-(4-methoxy-benzyl)-1H-tetrazole, MS: 238 (M). [Y. Satoh, S. De Lombaert, N. Marcopulos, J. Moliterni, M. Moskal, J. Tan, E. Wallace, Synthesis of tetrazole analogs of alpha-amino acids by alkylation of a Schiff base of alpha-aminomethyltetrazole. Tetrahedron Lett. (1998), 39(21), 3367–3370].

In analogy to the general synthesis of the amines, 5-Chloromethyl-1-(4-methoxy-benzyl)-1H-tetrazole and:
Phenethylamine gave 11-(4-Methoxy-benzyl)-1H-tetrazol-5-ylmethyl]-phenethyl-amine, MS: 324 (MH$^+$);
Cyclopropylamine gave after 3 days at 50° C. Cyclopropyl-[1-(4-methoxy-benzyl)-1H-tetrazol-5-ylmethyl]-amine, MS: 259 (M);
In analogy to the general synthesis of the amines, 3-bromo-propionitril and:
Cyclopropylamine gave 3-Cyclopropylamino-propionitrile, MS: 110 (M);
Benzylamine gave 3-Benzylamino-propionitrile, MS: 160 (M);
Further sidechains as described in literature:
(Piperidin-4-yloxy)-acetic acid tert-butyl ester (MH$^+$) was prepared according to literature: L. Alig, A. Edenhofer, P. Hadvary, M. Huerzeler, D. Knopp, M. Mueller, B. Steiner, A. Trzeciak, T. Weller "Low molecular weight, non-peptide fibrinogen receptor antagonists." J. Med. Chem. (1992), 35(23), 4393–407.

Example 8

Further Reagents

The following reagents were prepared according to the given literature:
5-Chlorosulfonyl-2-ethoxy-benzoic acid: D: J. Dale, P. J. Dunn, C. Golightly, M. L. Hughes, P. C. Levett, A. K. Pearce, P. M. Searle, G. Ward, and A. S. Wood Organic Process Research & Development 2000, 4, 1, 17–22;
2-phenyl-ethanesulfonyl chloride Z. Zhong, J. A. Bibbs, W. Yuan, C.-H. Wong, J.Amer.Chem.Soc.; 113; 6; 1991; 2259–2263;
3-Phenyl-propane-1-sulfonyl chloride: M. Truce, J.Amer.Chem.Soc.; 74; 1952; 974–975.

Example 9

(2S,4R)-4-(4-Methoxy-benzylsulfanl)-pyrrolidine-1,2-dicarboxylic acid 1-tert-butyl ester as educt 20 g (54.4 mmol) (2S,4R)-4-(4-Methoxy-benzylsulfanyl)-pyrrolidine-1,2-dicarboxylic acid 1-tert-butyl ester in 1.5 1 CH$_2$Cl$_2$ were treated with 6.6 ml (60 mmol, 1.1 eq) 4-methyl morpholine, 19.4 g (65.3 mmol, 1.2 eq) TPTU and 12.7 g (59.8 mmol) sarcosine benzylester-hydrochloride. The mixture was stirred at RT for 39 h, was concentrated and purified by column chromatography with EtOAc:CH$_2$Cl$_2$ 4:1 as eluent yielding 14.2 g (50%) (2S,4R)-2-(benzyloxycarbonylmethyl-methyl-carbamoyl)-4-(4-methoxy-benzylsulfanyl)-pyrrolidine-1-carboxylic acid tert-butyl ester.

To 24.24 g (45.8 mmol) (2S,4R)-2-(benzyloxycarbonylmethyl-methyl-carbamoyl)-4-(4-methoxy-benzylsulfanyl)-pyrrolidine-1-carboxylic acid tert-butyl ester in 150 ml CH$_2$Cl$_2$ were added 30 ml TFA at 0° C. and the solution was stirred at RT until no starting material could be detected. The reaction mixture was concentrated in vacuo and dissolved in toluene and evaporated three times. The crude oil was redissolved in CH$_2$Cl$_2$ and treated with 22.6 ml (205 mmol, 4.5 eq) 4-methyl morpholine, 15.57 g (68.7 mmol, 1.5 eq) 2-naphthylsulfonyl chloride and 560 mg (4.58 mmol, 0.1 eq) DMAP. The mixture was stirred at RT over night, was diluted with CH$_2$Cl$_2$ and was washed with 150 ml 1M KHSO$_4$, brine and dried over Na$_2$SO$_4$ yielding 27.9 g crude (2S,4R)-[[4-(4-methoxy-benzylsulfanyl)-1-(naphthalene-1-sulfonyl)-pyrrolidine-2-carbonyl]-methyl-amino]-acetic acid benzyl ester.

27.44 g crude (2S,4R)-[[4-(4-methoxy-benzylsulfanyl)-1-(naphthalene-1-sulfonyl)-pyrrolidine-2-carbonyl]-methyl-amino]-acetic acid benzyl ester in 1 l THF were treated with 160 ml 0.33 M LiOH at RT for 2 h. Ether was added and the phases were separated. The inorganic phase was extracted with ether, the inorganic phase was acidified and extracted with EtOAc, washed with brine and dried over Na$_2$SO$_4$. The product was isolated by precipitation with hexane yielding 14.5 g (62%) (2S,4R)-[[4-(4-methoxy-benzylsulfanyl)-1-(naphthalene-2-sulfonyl)-pyrrolidine-2-carbonyl]-methyl-amino]-acetic acid as light grey solid, MS: 529 (MH$^+$).

Final Products-ester and Acid:

100 mg (0.19 mmol) (2S,4R)-[[4-(4-methoxy-benzylsulfanyl)-1-(naphthalene-2-sulfonyl)-pyrrolidine-2-carbonyl]-methyl-amino]-acetic acid and 28 mg (0.29 mmol) phenol in 1 ml TFA were heated to 75° C. for 1h. The mixture was concentrated, dissolved in toluene and evaporated (3×). The residue was purified by flash chromatography yielding 46 mg (59%) (2S,4R)-[[4-Mercapto-1-(naphthalene-2-sulfonyl)-pyrrolidine-2-carbonyl]-methyl-amino]-acetic acid as white solid, mp 200-201° C., MS: 409 (MH$^+$).

100 mg (0.16 mmol) (2S,4R)-[[4-(4-methoxy-benzylsulfanyl)-1-(naphthalene-2-sulfonyl)-pyrrolidine-2-carbonyl]-methyl-amino]-acetic acid benzyl ester in 0.7 ml TFA were treated with 0.08 ml (0.63 mmol, 3.9 eq) trim-ethylchloro silane and 23 µl (0.32 mmol, 2 eq) DMSO at 0° C. The mixture was stirred at RT for 45 min, was concentrated and redissolved in EtOAc/NaHCO$_3$. The organic phase was washed with brine, dried over Na$_2$SO$_4$, and the crude product was purified by chromatography yielding 38 mg (47%) (2S,4R)-[[4-[5-(Benzyloxycarbonylmethyl-methyl-carbamoyl)-1-(naphthalene-2-sulfonyl)-pyrrolidin-3-yldisulfanyl]-1-(naphthalene-2-sulfonyl)-pyrrolidine-2-carbonyl]-methyl-amino]-acetic acid benzyl ester as white foam. This was dissolved in 1 ml trifluoro ethanol and treated with 13 µl (0.053 mmol) tributyl phosphine and 6.5 µl (0.36 mmol) H$_2$O at 0° C.. After 1h the reaction mixture was concentrated in vacuo and purified by flash chromatography giving 28 mg (73%) (2S,4R)-[[4-mercapto-1-(naphthalene-2-sulfonyl)-pyrrolidine-2-carbonyl]-methyl-amino]-acetic acid benzyl ester as colorless oil, MS: 499 (MH$^+$).

Example 10

Further Modification of Intermediate (2S,4R)-[[4-(4-methoxy-benzylsulfanyl)-1-(naphthalene-2-sulfonyl)-pyrrolidine-2-carbonyl]-methyl-amino]-acetic acid 248 mg (0.47 mmol) (2S,4R)-[[4-(4-methoxy-benzylsulfanyl)-1-(naphthalene-2-sulfonyl)-pyrrolidine-2-carbonyl]-methyl-amino]-acetic acid in 1.13 ml CH$_2$Cl$_2$ were treated with 935 μl (0.94 mmol, 2.0 eq) NMM, 1.1 ml 0.085 M (0.09 mmol, 0.2 eq) HOBT in $CH_2Cl_2$, 3.77 ml 0.15M (0.56 mmol, 1.2 eq) EDCI in $CH_2Cl_2$ and 1.2 ml 0.43 M (0.52 mmol, 1.1 eq) o-toluidine in $CH_2Cl_2$. The solution was shaken over night, the solvent was evaporated and the residue was dissolved in EtOAc, extracted with 1M $KHSO_4$, sat. $NaHCO_3$ solution and brine, dried over $Na_2SO_4$ and evaporated.

The crude product was dissolved in 5.8 ml TFA and treated with 460 [μl (2.9 mmol) triethyl silane at 80° C. for 1 h. The solution was diluted with $CH_2Cl_2$ and water, and the pH was adjusted to 7 by adding sat. $NaHCO_3$ solution. The inorganic phase was extracted with $CH_2Cl_2$, the organic phase was washed with brine and dried with $Na_2SO_4$. Column chromatography yielded 26 mg (18%, 2 steps) (2S,4R)-4-Mercapto-1-(naphthalene-2-sulfonyl)-pyrrolidine-2-carboxylic acid methyl-(o-tolylcarbamoyl-methyl)-amide as white crystalline, MS: 498 ($MH^+$).

Analogously, the following compounds were prepared from (2S,4R)-[[4-(4-methoxy-benzylsulfanyl)-1-(naphthalene-2-sulfonyl)-pyrrolidine-2-carbonyl]-methyl-amino]-acetic acid and 3,5-difluoroaniline, 4-fluoroaniline, 3-fluoroaniline, 2-aminopyridine, 2-fluoroaniline and 2,6-difluoroaniline, aniline, respectively:

(2S,4R)-4-Mercapto-1-(naphthalene-2-sulfonyl)-pyrrolidine-2-carboxylic acid [(3,5-difluoro-phenylcarbamoyl)-methyl]-methyl-amide as white solid, MS: 520 ($MH^+$);

(2S,4R)-4-Mercapto-1-(naphthalene-2-sulfonyl)-pyrrolidine-2-carboxylic acid [(4-fluoro-phenylcarbamoyl)-methyl]-methyl-amide as white crystalline, MS: 502 ($MH^+$);

(2S,4R)-4-Mercapto-1-(naphthalene-2-sulfonyl)-pyrrolidine-2-carboxylic acid [(3-fluoro-phenylcarbamoyl)-methyl]-methyl-amide as white crystalline, MS: 502 ($MH^+$);

(2S,4R)-4-Mercapto-1-(naphthalene-2-sulfonyl)-pyrrolidine-2-carboxylic acid methyl-(pyridin-2-ylcarbamoylmethyl)-amide as white amorphous, MS: 485 ($MH^+$);

(2S,4R)-4-Mercapto-1-(naphthalene-2-sulfonyl)-pyrrolidine-2-carboxylic acid [(2-fluoro-phenylcarbamoyl)-methyl]-methyl-amide as white solid, MS: 502 ($MH^+$);

(2S,4R)-4-Mercapto-1-(naphthalene-2-sulfonyl)-pyrrolidine-2-carboxylic acid [(2,6-difluoro-phenylcarbamoyl)-methyl]-methyl-amide as white solid, MS: 520 ($MH^+$).

(2S,4R)-4-Mercapto-1-(naphthalene-2-sulfonyl)-pyrrolidine-2-carboxylic acid methyl-phenylcarbamoylmethyl-amide as white solid, mp 90° C., MS: 484 ($MH^+$).

Example 11

(2S,4R)-4-(4-Methoxy-benzylsulfanyl)-pyrrolidine-1,2-dicarboxylic acid 1-tert-butyl ester as educt From (2S,4R)-4-(4-Methoxy-benzylsulfanyl)-pyrrolidine-1,2-dicarboxylic acid 1-tert-butyl ester and 4-(2-Methylamino-acetylamino)-benzoic acid ethyl ester (1.2.), followed by BOC cleavage (3.1.) was prepared (2S,4R)-4-(2-[[4-(4-Methoxy-benzylsulfanyl)-pyrrolidine-2-carbonyl]-methyl-amino]-acetylamino)-benzoic acid ethyl ester.

(2S,4R)-4-(2-[[4-(4-Methoxy-benzylsulfanyl)-pyrrolidine-2-carbonyl]-methyl-amino]-acetylamino)-benzoic acid ethyl ester was treated with 2-phenyl-ethanesulfonyl chloride (see above: preparation of reagents) (2.1.) via (2S,4R)-4-(2-{[4-(4-Methoxy-benzylsulfanyl)-1-(2-phenyl-ethanesulfonyl)-pyrrolidine-2-carbonyl]-methyl-amino}-acetylamino)-benzoic acid ethyl ester as white solid, MS: 654 ($MH^+$), followed by PMBether cleavage according to general procedure 8.1. to give:

(2S,4R)-4-[2-[[4-Mercapto-1-(2-phenyl-ethanesulfonyl)-pyrrolidine-2-carbonyl]-methyl-amino]-acetylamino]-benzoic acid ethyl ester as white crystalline, MS: 534 ($MH^+$).

Analogously, (2S,4R)-4-(2-[[4-(4-Methoxy-benzylsulfanyl)-pyrrolidine-2-carbonyl]-methyl-amino]-acetylamino)-benzoic acid ethyl ester was treated with 3-Phenyl-propane-1-sulfonyl chloride folowed by deprotection according to 8.1. to give (2S,4R)-4-[2-[[4-Mercapto-1-(3-phenyl-propane-1-sulfonyl)-pyrrolidine-2-carbonyl]-methyl-amino]-acetylamino]-benzoic acid ethyl ester as colorless foam MS: 548 ($MH^+$).

157 mg (0.24 mmol) (2S,4R)-4-(2-{[4-(4-Methoxy-benzylsulfanyl)-1-(2-phenyl-ethanesulfonyl)-pyrrolidine-2-carbonyl]-methyl-amino}-acetylamino)-benzoic acid ethyl ester were treated with 0.1 M LiOH according to 5.2., the crude product (2S,4R)-4-(2-{[4-(4-Methoxy-benzylsulfanyl)-1-(2-phenyl-ethanesulfonyl)-pyrrolidine-2-carbonyl]-methyl-amino}-acetylamino)-benzoic acid was dissolved in 1 ml TFA and heated to 75° C. in the presence of 23 mg (0.24 mmol) phenol for 1.5 h. The solvent was evaporated, the oil dissolved in toluene and evaporated (twice), the residue was titurated from hexane to yield 45 mg (2S,4R)-4-[2-[[4-Mercapto-1-(2-phenyl-ethanesulfonyl)-pyrrolidine-2-carbonyl]-methyl-amino]-acetylamino]-benzoic acid as light yellow solid, MS: 506 ($MH^+$).

Analogously, the following compounds were prepared from (2S,4R)-4-(4-Methoxy-benzylsulfanyl)-pyrrolidine-1,2-dicarboxylic acid 1-tert-butyl ester by treatment with 2-(2-Methylamino-acetylamino)-benzoic acid methyl ester-.HCl according to 1.3., followed by BOC cleavage 3.1., followed by ethyl isocyanate or 2-naphthyl isocyanate treatment (2.3.), respectively, followed by PMBthioether cleavage (8.1.) to give:

(2S,4R)-2-[2-[(1-Ethylcarbamoyl-4-mercapto-pyrrolidine-2-carbonyl)-methyl-amino]-acetylamino]-benzoic acid methyl ester as white crystalline, MS: 423 ($MH^+$);

(2S,4R)-2-[2-[[4-Mercapto-1-(naphthalen-2-ylcarbamoyl)-pyrrolidine-2-carbonyl]-methyl-amino]-acetylamino]-benzoic acid methyl ester as white solid, MS: 521 ($MH^+$).

Analogously, the following compounds were prepared from (2S,4R)-4-(4-Methoxy-benzylsulfanyl)-pyrrolidine-1,2-dicarboxylic acid 1-tert-butyl ester by treatment with 2-(2-Methylamino-acetylamino)-benzoic acid methyl ester-.HCl according to 1.3., followed by BOC cleavage 3.1., followed by treatment with 5-Chlorosulfonyl-2-ethoxy-benzoic acid (see above: preparation of reagents), 2-naphthylsulfonyl chloride, methyl sulfonylchloride (2.1.), respectively, followed by PMBthioether cleavage (8.1.) to give:

(2S,4R)-2-Ethoxy-5-[4-mercapto-2-[[(2-methoxycarbonyl-phenylcarbamoyl)-methyl]-methyl-carbamoyl]-pyrrolidine-1-sulfonyl]-benzoic acid as white crystalline, mp 65° C., MS: 580 ($MH^+$);

(2S,4R)-4-Mercapto-1-(naphthalene-2-sulfonyl)-pyrrolidine-2-carboxylic acid [(2-methoxy-phenylcarbamoyl)-methyl]-methyl-amide as white solid, mp 72° C., MS: 514 ($MH^+$);

(2S,4R)-2-[2-[(4-Mercapto-1-methanesulfonyl-pyrrolidine-2-carbonyl)-methyl-amino]-acetylamino]-benzoic acid methyl ester as white solid, mp 48° C., MS: 430 ($MH^+$).

Example 12

Tertiary Amides

12.1. SAmides (direct), Method A

A solution of 800 mg (1.38 mmol) (2S,4R)-1-(Naphthalene-2-sulfonyl)-4-tritylsulfanyl-pyrrolidine-2-carboxylic acid and 390 mg (1.66 mmol) crude phenethylamino-acetic acid tert-butyl ester in 14 ml THF was cooled to 0° C. and treated with 318 mg (1.66 mmol) EDCI and 19 mg (0.14 mmol) HOBT. The reaction was warmed up to RT over night and partitioned between aqueous 10% KHSO$_4$/ethyl acetate (3×). The organic phases were washed with aqueous saturated NaHCO$_3$ solution and dried over Na$_2$SO$_4$. Purification by flash-chromatography on silicagel (Hexane/EtOAc 4:1 to 1:1) gave 290 mg (26%) (2S,4R)-{[1-(Naphthalene-2-sulfonyl)-4-tritylsulfanyl-pyrrolidine-2-carbonyl]-phenethyl-amino}-acetic acid tert-butyl ester, MS: 797 (MH$^+$)
and 90 mg (10%) of (2S,4R)-1-(Naphthalene-2-sulfonyl)-4-tritylsulfanyl-pyrrolidine-2-carboxylic acid phenethyl-amide, MS: 683 (MH$^+$).

Trityl-deprotection was performed by procedure 9.1. or 9.2., if a p-methoxybenzyl group was present, Method 8.1. was used.

A solution of 159 mg (0.2 mmol) (2S,4R)-{[1-(Naphthalene-2-sulfonyl)-4-tritylsulfanyl-pyrrolidine-2-carbonyl]-phenethyl-amino}-acetic acid tert-butyl ester in 2 ml TFA was treated at RT with 0.3 ml (2 mmol) triethylsilane and further stirred at RT for 10 min. Evaporation at RT under reduced pressure and precipitation with Et$_2$O/pentane twice gave 78 mg (78%) of (2S,4R)-{[4-Mercapto-1-(naphthalene-2-sulfonyl)-pyrrolidine-2-carbonyl]-phenethyl-amino}-acetic acid as a white powder, mp: 198–200° C., MS: 497 (M-H)$^-$.

In Analogy:
(2S,4R)-1-(Naphthalene-2-sulfonyl)-4-tritylsulfanyl-pyrrolidine-2-carboxylic acid phenethyl-amide gave (2S,4R)-4-Mercapto-1-(naphthalene-2-sulfonyl)-pyrrolidine-2-carboxylic acid phenethyl-amide, mp: 138.5–143° C., MS: 441 (MH$^+$).

In addition, the compounds according to Table 1 and 2 were prepared:

TABLE 1

By reaction of (2S,4R)-1-Methanesulfonyl-4-tritylsulfanyl-pyrrolidine-2-carboxylic acid with the 2. Educt, following Method A.

| NAME | 2. Educt | MS | | COLOR | Melting Point | PHYSICAL FORM |
|---|---|---|---|---|---|---|
| (2S,4R)-[(4-Mercapto-1-methanesulfonyl-pyrrolidine-2-carbonyl)-phenethyl-amino]-acetic acid | Phenethylamino-acetic acid tert-butyl ester | 387 | (MH+) | light yellow | | viscous oil |
| (2S,4R)-3-[(4-Mercapto-1-methanesulfonyl-pyrrolidine-2-carbonyl)-(3-phenyl-propyl)-amino]-propionic acid | 3-(3-Phenyl-propylamino)-propionic acid tert-butyl ester | 413 | (M−H)$^-$ | white | | viscous oil |
| (2S,4R)-[[2-(1H-Indol-3-yl)-ethyl]-(4-mercapto-1-methanesulfonyl-pyrrolidine-2-carbonyl)-amino]-acetic acid | [2-(1H-Indol-3-yl)-ethylamino]-acetic acid tert-butyl ester | 426 | (MH+) | off-white | 152–205° C., sl. dec. | powder |

TABLE 2

By reaction of (2S,4R)-1-Naphthalene-2-sulfonyl)-4-tritylsulfanyl-pyrrolidine-2-carboxylic acid with the 2. Educt, following Method A.

| NAME | 2. Educt | MS | | COLOR | MP | PHYSICAL FORM |
|---|---|---|---|---|---|---|
| (2S,4R)-{[4-Mercapto-1-(naphthalene-2-sulfonyl)-pyrrolidine-2-carbonyl]-phenyl-amino}-acetic acid | Phenylamino-acetic acid tert-butyl ester | 471 | (MH+) | white | 150–165° C. sl. dec. | solid |
| (2S,4R)-4-Mercapto-1-(naphthalene-2-sulfonyl)-pyrrolidine-2-carboxylic acid phenylamide | side product of (2S,4R)-{[4-Mercapto-1-(naphthalene-2-sulfonyl)-pyrrolidine-2-carbonyl]-phenyl-amino}-acetic acid | 413 | (MH+) | white | 181–183° C. | solid |
| (2S,4R)-{[4-Mercapto-1-(naphthalene-2-sulfonyl)-pyrrolidine-2-carbonyl]-phenethyl-amino}-acetic acid | Phenethylamino-acetic acid tert-butyl ester | 497 | (M−H)$^-$, descr. | white | 198–200° C. | powder |
| (2S,4R)-4-Mercapto-1-(naphthalene-2-sulfonyl)-pyrrolidine-2-carboxylic acid phenethyl-amide | side product of (2S,4R)-{[4-Mercapto-1-(naphthalene-2-sulfonyl)-pyrrolidine-2-carbonyl]-phenethyl-amino}-acetic acid | 441 | (MH+), descr. | white | 138.5–143° C. | solid |
| (2S,4R)-[[4-Mercapto-1-(naphthalene-2-sulfonyl)-pyrrolidine-2-carbonyl]-(3-phenyl-propyl)-amino]-acetic acid | (3-Phenyl-propylamino)-acetic acid tert-butyl ester | 511 | (M−H)$^-$ | white | 166–173° C. | solid |
| (2S,4R)-3-{[4-Mercapto-1-(naphthalene-2-sulfonyl)-pyrrolidine-2-carbonyl]-phenethyl-amino}-propionic acid | 3-Phenethylamino-propionic acid tert-butyl ester | 511 | (M−H)$^-$ | white | 138–140° C. | crystalline |
| (2S,4R)-3-[[4-Mercapto-1-(naphthalene-2- | 3-(3-Phenyl-propylamino)- | 525 | (M−H)$^-$ | white | 150–152° C. | solid |

TABLE 2-continued

By reaction of (2S,4R)-1-Naphthalene-2-sulfonyl)-4-tritylsulfanyl-pyrrolidine-2-carboxylic acid with the 2. Educt, following Method A.

| NAME | 2. Educt | MS | | COLOR | MP | PHYSICAL FORM |
|---|---|---|---|---|---|---|
| sulfonyl)-pyrrolidine-2-carbonyl]-(3-phenyl-propyl)-amino]-propionic acid | propionic acid tert-butyl ester | | | | | |
| (2S,4R)-4-Mercapto-1-(naphthalene-2-sulfonyl)-pyrrolidine-2-carboxylic acid (3-phenyl-propyl)-amide | side product of (2S,4R)-3-[[4-Mercapto-1-(naphthalene-2-sulfonyl)-pyrrolidine-2-carbonyl]-(3-phenyl-propyl)-amino]-propionic acid | 455 | (MH+) | light yellow | | viscous oil |
| (2S,4R)-{[2-(1H-Indol-3-yl)-ethyl]-[4-mercapto-1-(naphthalene-2-sulfonyl)-pyrrolidine-2-carbonyl]-amino}-acetic acid | [2-(1H-Indol-3-yl)-ethylamino]-acetic acid tert-butyl ester | 538 | (MH+) | off-white | 199–235° C., sl. dec. | powder |
| (2S,4R)-{[2-(2-Fluoro-phenyl)-ethyl]-[4-mercapto-1-(naphthalene-2-sulfonyl)-pyrrolidine-2-carbonyl]-amino}-acetic acid | [2-(2-Fluoro-phenyl)-ethylamino]-acetic acid tert-butyl ester | 515 | (M–H)⁻ | off-white | 182–189° C., dec. | powder |
| (2S,4R)-{[2-(4-Fluoro-phenyl)-ethyl]-[4-mercapto-1-(naphthalene-2-sulfonyl)-pyrrolidine-2-carbonyl]-amino}-acetic acid | [2-(4-Fluoro-phenyl)-ethylamino]-acetic acid tert-butyl ester | 517 | (MH+) | off-white | 168–178° C., dec. | powder |
| (2S,4R)-3-{(2-Fluoro-benzyl)-[4-mercapto-1-(naphthalene-2-sulfonyl)-pyrrolidine-2-carbonyl]-amino}-propionic acid | 3-(2-Fluoro-benzylamino)-propionic acid tert-butyl ester | 515 | (M–H)⁻ | white | | foam |
| (2S,4R)-{[2-(3-Fluoro-phenyl)-ethyl]-[4-mercapto-1-(naphthalene-2-sulfonyl)-pyrrolidine-2-carbonyl]-amino}-acetic acid | [2-(3-Fluoro-phenyl)-ethylamino]-acetic acid tert-butyl ester | 515 | (M–H)⁻ | white | 162–174° C., slowly dec. | powder |
| (2S,4R)-[[4-Mercapto-1-(naphthalene-2-sulfonyl)-pyrrolidine-2-carbonyl]-(2-p-tolyl-ethyl)-amino]-acetic acid | (2-p-Tolyl-ethylamino)-acetic acid tert-butyl ester | 513 | (MH+) | off-white | 146–166° C., slowly dec. | powder |
| (2S,4R)-[[4-Mercapto-1-(naphthalene-2-sulfonyl)-pyrrolidine-2-carbonyl]-(3-methyl-butyl)-amino]-acetic acid | (3-Methyl-butylamino)-acetic acid tert-butyl ester | 465 | (MH+) | off-white | | foam |
| (2S,4R)-3-[[4-Mercapto-1-(naphthalene-2-sulfonyl)-pyrrolidine-2-carbonyl]-(2,4,5-trifluoro-benzyl)-amino]-propionic acid | 3-(2,4,5-Trifluoro-benzylamino)-propionic acid tert-butyl ester | 553 | (MH+) | white | | foam |
| (2S,4R)-4-Mercapto-1-(naphthalene-2-sulfonyl)-pyrrolidine-2-carboxylic acid 2,4,5-trifluoro-benzylamide | side product of (2S,4R)-3-[[4-Mercapto-1-(naphthalene-2-sulfonyl)-pyrrolidine-2-carbonyl]-(2,4,5-trifluoro-benzyl)-amino]-propionic acid | 481 | (MH+) | white | | foam |
| (2S,4R)-4-Mercapto-1-(naphthalene-2-sulfonyl)-pyrrolidine-2-carboxylic acid phenethyl-(1H-tetrazol-5-ylmethyl)-amide | [1-(4-Methoxy-benzyl)-1H-tetrazol-5-ylmethyl]-phenethyl-amine | 523 | (MH+) | white | | solid |
| (2S,4R)-4-Mercapto-1-(naphthalene-2-sulfonyl)-pyrrolidine-2-carboxylic acid cyclopropyl-(1H-tetrazol-5-ylmethyl)-amide | Cyclopropyl-[1-(4-methoxy-benzyl)-1H-tetrazol-5-ylmethyl]-amine | 459 | (MH+) | white | 106° C. sl. dec. | solid |
| (2S,4R)-3-[(2,5-Difluoro-benzyl)-[4-mercapto-1-(naphthalene-2-sulfonyl)-pyrrolidine-2-carbonyl]-amino]-propionic acid | 3-(2,5-Difluoro-benzylamino)-propionic acid tert-butyl ester | 535 | (MH+) | white | 73° C. slowly dec. | solid |
| (2R,4R)-[[4-Mercapto-1-(naphthalene-2-sulfonyl)-pyrrolidine-2-carbonyl]-(2-p-tolyl-ethyl)-amino]-acetic acid | (2-p-Tolyl-ethylamino)-acetic acid tert-butyl ester | 513 | (MH+) | off-white | 109–123° C., slowly dec. | powder |
| (2S,4R)-4-Mercapto-1-(naphthalene-2-sulfonyl)-pyrrolidine-2-carboxylic acid (3-methyl-butyl)-[1,2,4]oxadiazol-3-ylmethyl-amide | (3-Methyl-butyl)-[1,2,4]oxadiazol-3-ylmethyl-amine | 489 | (MH+) | white | | foam |
| (2S,4R)-4-Mercapto-1-(naphthalene-2-sulfonyl)-pyrrolidine-2-carboxylic acid (1H-benzoimidazol-2-ylmethyl)-amide trifluoro-acetate (1:1) | 2-(aminomethyl)benzimidazole dihydrochloride/ iPr₃EtN | 467 | (MH+) | white | | crystalline |
| (2S,4R)-4-Mercapto-1-(naphthalene-2-sulfonyl)-pyrrolidine-2-carboxylic acid isopropylamide | isopropylamine | 379 | (MH+) | white | | amorph freeze-dried solid |
| (2S,4R)-4-Mercapto-1-(naphthalene-2-sulfonyl)-pyrrolidine-2-carboxylic acid hexyl-methyl-amide | hexyl-methylamine | 435 | (MH+) | white | | amorph freeze-dried solid |
| (2S,4R)-4-Mercapto-1-(naphthalene-2-sulfonyl)-pyrrolidine-2-carboxylic acid benzylamide | 2-Aminopyridine | 427 | (MH+) | white | 117° C. | solid |

12.2. Amides, Method B (indirect)

Following the the general method for EDCI-coupling 1.3. (2S,4R)-1-(Naphthalene-2-sulfonyl)-4-tritylsulfanyl-pyrrolidine-2-carboxylic acid with glycine tert-butylester•hydrochloride/N-methylmorpholine gave (2S,4R)-{[1-(Naphthalene-2-sulfonyl)-4-tritylsulfanyl-pyrrolidine-2-carbonyl]-amino}-acetic acid tert-butyl ester, MS: 693 (MH$^+$).

In analogy:

(2S,4R)-1-(Naphthalene-2-sulfonyl)-4-tritylsulfanyl-pyrrolidine-2-carboxylic acid and β-alanine t-butyl ester•hydrochloride gave (2S,4R)-3-{[1-(Naphthalene-2-sulfonyl)-4-tritylsulfanyl-pyrrolidine-2-carbonyl]-amino}-propionic acid tert-butyl ester, MS: 707 (MH$^+$);

(2S,4R)-1-(Naphthalene-2-sulfonyl)-4-tritylsulfanyl-pyrrolidine-2-carboxylic acid and 2,2,2-trifluoroethylamine gave (2S,4R)-1-(Naphthalene-2-sulfonyl)-4-tritylsulfanyl-pyrrolidine-2-carboxylic acid (2,2,2-trifluoro-ethyl)-amide, MS: 661 (MH$^+$).

A solution of 346.5 mg (0.5 mmol) (2S,4R)-{[1-(Naphthalene-2-sulfonyl)-4-tritylsulfanyl-pyrrolidine-2-carbonyl]-amino}-acetic acid tert-butyl ester in 3 ml DMF was treated at 0° C. with 0.24 ml (2 mmol) benzylbromide and 35 mg (0.8 mmol) 55% NaH, warmed up over night to RT. The reaction was poured into aqueous saturated NH$_4$Cl/EtOAc (3×). The organic phase was washed with aqueous 10% NaCl solution, dried over Na$_2$SO$_4$ and evaporated under reduced pressure. Purification by flash-chromatography on silicagel (Hexane/EtOAc 9:1) gave 277 mg (71%) (2S,4R)-[Benzyl-[1-(naphthalene-2-sulfonyl)-4-tritylsulfanyl-pyrrolidine-2-carbonyl]- amino}-acetic acid tert-butyl ester, MS: 781 (M-H)$^-$.

Trityl deprotection following method 9.2. gave (2S,4R)-{Benzyl-[4-mercapto-1-(naphthalene-2-sulfonyl)-pyrrolidine-2-carbonyl]-amino}-acetic acid, MS: 483 (M-H)$^-$.

In analogy:

(2S,4R)-{[1-(Naphthalene-2-sulfonyl)-4-tritylsulfanyl-pyrrolidine-2-carbonyl]-amino}-acetic acid tert-butyl ester and cyclopropylmethyl bromide gave (2S,4R)-{Cyclopropylmethyl-[4-mercapto-1-(naphthalene-2-sulfonyl)-pyrrolidine-2-carbonyl]-amino}-acetic acid, MS: 449 (MH$^+$);

(2S,4R)-{[-(Naphthalene-2-sulfonyl)-4-tritylsulfanyl-pyrrolidine-2-carbonyl]-amino}-acetic acid tert-butyl ester and methyl bromoacetate gave (2S,4R)-{[4-Mercapto-1-(naphthalene-2-sulfonyl)-pyrrolidine-2-carbonyl]-methoxycarbonylmethyl-amino}-acetic acid, mp: slow dec. 70–78° C., MS: 465 (M-H)$^-$;

(2S,4R)-3-{[1-(Naphthalene-2-sulfonyl)-4-tritylsulfanyl-pyrrolidine-2-carbonyl]-amino}-propionic acid tert-butyl ester and benzylbromide gave (2S,4R)-3-{Benzyl-[4-mercapto-1-(naphthalene-2-sulfonyl)-pyrrolidine-2-carbonyl]-amino}-propionic acid, mp: slow dec. 58–63° C., MS: 499 (MH$^+$);

(2S,4R)-3-{[1-(Naphthalene-2-sulfonyl)-4-tritylsulfanyl-pyrrolidine-2-carbonyl]-amino}-propionic acid tert-butyl ester and 3-Bromomethyl-indole-1-carboxylic acid tert-butyl ester [T. K. Venkatachalam, S. Mzengeza, M. Diksic.An improved synthesis of 1-(tert-butyloxycarbonyl)-3-(bromomethyl)indole. Org. Prep. Proced. Int. 1993, 25,249–51] gave (2S,4R)-3-{(1H-Indol-3-ylmethyl)-[4-mercapto-1-(naphthalene-2-sulfonyl)-pyrrolidine-2-carbonyl]-amino}-propionic acid, mp: 114–120° C., dec., MS: 538 (MH$^+$);

(2S,4R)-1-(Naphthalene-2-sulfonyl)-4-tritylsulfanyl-pyrrolidine-2-carboxylic acid (2,2,2-trifluoro-ethyl)-amide and tert-butyl bromoacetate gave (2S,4R)-[[4-Mercapto-1-(naphthalene-2-sulfonyl)-pyrrolidine-2-carbonyl]-(2,2,2-trifluoro-ethyl)-amino]-acetic acid, MS: 477 (MH$^+$);

(2S,4R)-[Benzyl-[1-(naphthalene-2-sulfonyl)-4-tritylsulfanyl-pyrrolidine-2-carbonyl]-amino}-acetic acid tert-butyl ester gave (2S,4R)-{[4-Mercapto-1-(naphthalene-2-sulfonyl)-pyrrolidine-2-carbonyl]-amino}-acetic acid, MS: 395 (MH$^+$);

(2S,4R)-1-(Naphthalene-2-sulfonyl)-4-tritylsulfanyl-pyrrolidine-2-carboxylic acid (2,2,2-trifluoro-ethyl)-amide gave (2S,4R)-4-Mercapto-1-(naphthalene-2-sulfonyl)-pyrrolidine-2-carboxylic acid (2,2,2-trifluoro-ethyl)-amide, MS: 419 (MH$^+$).

Alpha-alkylation:

A solution of 346 mg (0.5 mmol) (2S,4R)-{[1-(Naphthalene-2-sulfonyl)-4-tritylsulfanyl-pyrrolidine-2-carbonyl]-amino}-acetic acid tert-butyl ester in 10 ml THF at −78° C. was treated with 1.1 ml (1M in THF, 1.1 mmol) Lithium bis(trimethlsilyl)amide solution (LiHMDS). 0.127 ml (1.5 mmol) Allylbromide was added after 30 min and the reaction was warmed up to RT over night. The reaction was partitioned between aqueous 10% KHSO$_4$/EtOAc (4×), the organic phases were washed with aqueous 10% NaCl, dried over Na$_2$SO$_4$ and evaporated. Purification by flash-chromatography on silicagel (Hexane/EtOAc 2:1) and pre-cipitation with Et$_2$O/pentane gave 76 mg (21%) (2RS)-2-{(2S,4R)-[1-(Naphthalene-2-sulfonyl)-4-tritylsulfanyl-pyrrolidine-2-carbonyl]-amino}-pent-4-enoic acid tert-butyl ester, MS: 733 (MH$^+$).

Trityl deprotection following Method 9.2. gave a 1:1 Mixture of (R)- and (S)-2-{[(2S,4R)-4-mercapto-1-(naphthalene-2-sulfonyl)-pyrrolidine-2-carbonyl]-amino}-pent-4-enoic acid, MS: 433 (M-H)$^-$.

Example 13

Tetrazol derivatives

In analogy to the amide coupling, (1.3.): (2S,4R)-1-(Naphthalene-2-sulfonyl)-4-tritylsulfanyl-pyrrolidine-2-carboxylic acid and 3-Cyclopropylamino-propionitrile gave (2S,4R)-1-(Naphthalene-2-sulfonyl)-4-tritylsulfanyl-pyrrolidine-2-carboxylic acid (2-cyano-ethyl)-cyclopropyl-amide, MS: 672 (MH$^+$).

In analogy:

(2S,4R)-1-(Naphthalene-2-sulfonyl)-4-tritylsulfanyl-pyrrolidine-2-carboxylic acid and 3-Benzylamino-propionitrile gave (2S,4R)-1-(Naphthalene-2-sulfonyl)-4-tritylsulfanyl-pyrrolidine-2-carboxylic acid benzyl-(2-cyano-ethyl)-amide, MS: 722 (MH$^+$).

(2S,4R)-1-(Naphthalene-2-sulfonyl)-4-tritylsulfanyl-pyrrolidine-2-carboxylic acid and 3-amino-propionitrile gave (2S,4R)-1-(Naphthalene-2-sulfonyl)-4-tritylsulfanyl-pyrrolidine-2-carboxylic acid (2-cyano-ethyl)-amide, mp: 86–90° C., MS: 632 (MH$^+$).

Trityl deprotection following Method 9.2.:

(15 min at RT): (2S,4R)-1-(Naphthalene-2-sulfonyl)-4-tritylsulfanyl-pyrrolidine-2-carboxylic acid (2-cyano-ethyl)-cyclopropyl-amide gave (2S,4R)-4-Mercapto-1-(naphthalene-2-sulfonyl)-pyrrolidine-2-carboxylic acid (2-carbamoyl-ethyl)-cyclopropyl-amide, mp: 157.9-159.9° C., MS: 448 (MH$^+$).

(30 min at 0° C., and evaporation at max RT): (2S,4R)-1-(Naphthalene-2-sulfonyl)-4-tritylsulfanyl-pyrrolidine-2-carboxylic acid (2-cyano-ethyl)-amide gave (2S,4R)-4-Mercapto-1-(naphthalene-2-sulfonyl)-pyrrolidine-2-carboxylic acid (2-cyano-ethyl)-amide, MS: 412 (M$^+$Na$^+$).

Synthesis of the Tetrazol:

A solution of 336 mg (0.5 mmol) (2S,4R)-1-(Naphthalene-2-sulfonyl)-4-tritylsulfanyl-pyrrolidine-2-carboxylic acid (2-cyano-ethyl)-cyclopropyl-amide, 267 mg (5 mmol) $NH_4Cl$ and 325 mg (5 mmol) $NaN_3$ in 10 ml DMF were heated at 70° C. for 22 h. 267 mg (5 mmol) $NH_4Cl$ and 325 mg (5 mmol) $NaN_3$ together with 40 ml DMF were added and heated at 100° C. (24h) and at 120° C. (24h). The reaction was poured in $H_2O$ (0° C.)/EtOAc (3×). The organic phases were washed with aqueous 10% $KHSO_4$, 10% NaCl solution and dried over $Na_2SO_4$. Purification by flash-chromatography on silicagel ($CH_2Cl_2$/MeOH: 99:1) gave 143 mg (40%) (2S,4R)-1-(Naphthalene-2-sulfonyl)-4-tritylsulfanyl-pyrrolidine-2-carboxylic acid cyclopropyl-[2-(1H-tetrazol-5-yl)-ethyl]-amide, MS: 715 ($MH^+$).

Trityl deprotection following Method 9.2. (with a short heating to 80° C.) gave (2S,4R)-4-Mercapto-1-(naphthalene-2-sulfonyl)-pyrrolidine-2-carboxylic acid cyclopropyl-[2-(1H-tetrazol-5-yl)-ethyl]-amide, mp: 173.5° C. dec., MS: 473 ($MH^+$).

In analogy:
(2S,4R)-1-(Naphthalene-2-sulfonyl)-4-tritylsulfanyl-pyrrolidine-2-carboxylic acid benzyl-(2-cyano-ethyl)-amide gave (2S,4R)-4-Mercapto-1-(naphthalene-2-sulfonyl)-pyrrolidine-2-carboxylic acid benzyl-[2-(1H-tetrazol-5-yl)-ethyl]-amide, MS: 523 ($MH^+$).

Method A:

A solution of 520 mg (0.9 mmol) (2S,4R)-1-(Naphthalene-2-sulfonyl)-4-tritylsulfanyl-pyrrolidine-2-carboxylic acid and 315 mg (1 mmol) (1S)-3-[5-(1-Amino-2-biphenyl-4-yl-ethyl)-tetrazol-1-yl]-propionitrile [S. De Lombaert. Preparation of tetrazolylalkylaminomethylphosphonates as neutral endopeptidase inhibitors. U.S., 17 pp. CODEN: USXXAM. U.S. Pat. No. 5,273,990 A 931228] in 5 ml THF was cooled to 0° C. and treated with 206 mg (1.1 mmol) EDCI and 14 mg (0.09 mmol) HOBT. The reaction was stirred for 3 h at RT and partitioned between aqueous 10% $KHSO_4$/ethyl acetate (3×). The organic phases were washed with aqueous saturated $NaHCO_3$ solution and dried over $Na_2SO_4$. Purification by flash-chromatography on silicagel (Hexane/EtOAc 1:1) gave 639 mg (81%) (2S,4R)-1-(Naphthalene-2-sulfonyl)-4-tritylsulfanyl-pyrrolidine-2-carboxylic acid [(S)-2-biphenyl-4-yl-1-[1-(2-cyano-ethyl)-1H-tetrazol-5-yl]-ethyl]-amide, Mp: 122–133 slow dec, MS: 880 ($MH^+$).

A solution of 300 mg (0.34 mmol) (2S,4R)-1-(Naphthalene-2-sulfonyl)-4-tritylsulfanyl-pyrrolidine-2-carboxylic acid [(S)-2-biphenyl-4-yl-1-[1-(2-cyano-ethyl)-1H-tetrazol-5-yl]-ethyl]-amide in 10 ml $CH_2Cl_2$ was treated at 0° C. with 0.05 ml DBU and stirred 3 h at RT. The reaction was poured in aqueous 10% $KHSO_4$/EtOAc (3×). The organic phases were washed with aqueous 10% NaCl solution and dried over $Na_2SO_4$ to give 220 mg (78%) of (2S,4R)-1-(Naphthalene-2-sulfonyl)-4-tritylsulfanyl-pyrrolidine-2-carboxylic acid [(S)-2-biphenyl-4-yl-1-(1M-tetrazol-5-yl)-ethyl]-amide. mp: 135–145 slow dec, MS: 827 ($MH^+$).

Trityl deprotection following Method 9.2. gave (2S,4R)-4-Mercapto-1-(naphthalene-2-sulfonyl)-pyrrolidine-2-carboxylic acid [(S)-2-biphenyl-4-yl-1-(1H-tetrazol-5-yl)-ethyl]-amide, mp: 245–247.5° C., MS: 585 ($MH^+$).

In analogy:
(2S,4R)-1-Methanesulfonyl-4-tritylsulfanyl-pyrrolidine-2-carboxylic acid gave (2S,4R)-4-Mercapto-1-methanesulfonyl-pyrrolidine-2-carboxylic acid [(S)-2-biphenyl-4-yl-1-(1H-tetrazol-5-yl)-ethyl]-amide, mp: 208.5–213.5° C., MS: 473 ($MH^+$).

Method B:

A solution of 200 mg (0.34 mmol) (2S,4R)-1-(Naphthalene-2-sulfonyl)-4-tritylsulfanyl-pyrrolidine-2-carboxylic acid and 42 mg (0.38 mmol) N-hydroxy-2-pyridone in 15 ml $CH_2Cl_2$ were treated at 0° C. with 72 mg (0.38 mmol) of EDCI. After 3.5h at RT, it was cooled (0° C.) and treated with 37 mg (0.38 mmol) of 5-aminomethyl-tetrazol. The reaction was stirred over night at RT, 2 ml DMF were added and after 4 h at RT the reaction was extracted with EtOAc/aqueous saturated $NaHCO_3$. The organic phase was washed with aqueous 10% $KHSO_4$, dried over $Na_2SO_4$ and purified by flash-chromatography on silicagel ($CH_2Cl_2$/MeOH 9:1) to give 100 mg (44%) of (2S,4R)-1-(Naphthalene-2-sulfonyl)-4-tritylsulfanyl-pyrrolidine-2-carboxylic acid (1H-tetrazol-5-ylmethyl)-amide, mp: 135–145 slow dec, MS: 661 ($MH^+$).

Trityl deprotection following Method 9.2. gave (2S,4R)-4-Mercapto-1-(naphthalene-2-sulfonyl)-pyrrolidine-2-carboxylic acid (1H-tetrazol-5-ylmethyl)-amide, mp: 61–73° C. slow dec., MS: 419 ($MH^+$).

In analogy:
(2S,4R)-1-Methanesulfonyl-4-tritylsulfanyl-pyrrolidine-2-carboxylic acid gave (2S,4R)-1-Methanesulfonyl-4-tritylsulfanyl-pyrrolidine-2-carboxylic acid (1H-tetrazol-5-ylmethyl)-amide, MS: 549 ($MH^+$),
which was trityl-deprotected (method 9.2.) to give (2S,4R)-4-Mercapto-1-methanesulfonyl-pyrrolidine-2-carboxylic acid (1H-tetrazol-5-ylmethyl)-amide, MS: 307 ($MH^+$).

A solution of 800 mg (1.21 mmol) (2S,4R)-1-(Naphthalene-2-sulfonyl)-4-tritylsulfanyl-pyrrolidine-2-carboxylic acid (1H-tetrazol-5-ylmethyl)-amide in 15 ml DMF was treated at 0° C. with 0.15 ml (2.4 mmol) iodomethane and 122 mg (2.8 mmol) 55% NaH and warmed up to RT for 3 h. The reaction was stopped with $H_2O$ and extracted with $Et_2O$ (3×). The organic phases were washed with aqueous 10% $KHSO_4$, dried over $Na_2SO_4$ and evaporated. Purification by flash-chromatography on silica gel (Hexane/EtOAc 1:1 to 2:1) gave 2 isomers. The structure were determined retrospective from the final product (by CH—COSY):

180 mg (43%) (2S,4R)-1-(Naphthalene-2-sulfonyl)-4-tritylsulfanyl-pyrrolidine-2-carboxylic acid methyl-(2-methyl-2H-tetrazol-5-ylmethyl)-amide, mp: 69–80° C. slow dec., MS: 689 ($MH^+$);

190 mg (45%) (2S,4R)-1-(Naphthalene-2-sulfonyl)-4-tritylsulfanyl-pyrrolidine-2-carboxylic acid methyl-(1-methyl-1H-tetrazol-5-ylmethyl)-amide, mp: 46–56° C. slow dec., MS: 689 ($MH^+$).

Trityl Deprotection Following Method 9.2.:

(2S,4R)-1-(Naphthalene-2-sulfonyl)-4-tritylsulfanyl-pyrrolidine-2-carboxylic acid methyl-(2-methyl-2H-tetrazol-5-ylmethyl)-amide gave (2S,4R)-4-Mercapto-1-(naphthalene-2-sulfonyl)-pyrrolidine-2-carboxylic acid methyl-(2-methyl-2H-tetrazol-5-ylmethyl)-amide, MS: 447 ($MH^+$)

and (2S,4R)-1-(Naphthalene-2-sulfonyl)-4-tritylsulfanyl-pyrrolidine-2-carboxylic acid methyl-(1-methyl-1H-tetrazol-5-ylmethyl)-amide gave (2S,4R)-4-Mercapto-1-(naphthalene-2-sulfonyl)-pyrrolidine-2-carboxylic acid methyl-(1-methyl-1H-tetrazol-5-ylmethyl)-amide, mp: 103° C., slow dec., MS: 447 ($MH^+$).

A suspension of 865 mg (1.3 mmol) (2S,4R)-1-(Naphthalene-2-sulfonyl)-4-tritylsulfanyl-pyrrolidine-2-carboxylic acid (1H-tetrazol-5-ylmethyl)-amide, 0.19 ml (1.4 mmol) 4-methoxybenzyl chloride, 0.19 ml (1.4 mmol) triethylamine and a spatula of sodium iodide in 10 ml acetone was heated at 75° C. for 15 h. The reaction was partitioned between aqueous 10% KHSO$_4$/Et$_2$O (3×). The organic phases were dried over Na$_2$SO$_4$ and precipitated from Et$_2$O to give 1:1 mixture of (2S,4R)-1-(naphthalene-2-sulfonyl)-4-tritylsulfanyl-pyrrolidine-2-carboxylic acid 1-(4-methoxy-benzyl)-1H- and [2-(4-methoxy-benzyl)-2H-tetrazol-5-ylmethyl]-amide, MS: 781 (MH$^+$).

A solution of 350 mg (0.44 mmol) 1:1 mixture of (2S,4R)-1-(naphthalene-2-sulfonyl)-4-tritylsulfanyl-pyrrolidine-2-carboxylic acid 1-(4-methoxy-benzyl)-1H- and [2-(4-methoxy-benzyl)-2H-tetrazol-5-ylmethyl]-amide was treated at 0° C. with 0.11 ml (1.7 mmol) iodomethane and 31 mg (0.7 mmol) 55% NaH, warmed up during 3 h and stirred at RT for additional 1.5 h. The reaction was poured into aqueous 10% KHSO$_4$/EtOAc (3×). The organic phase was washed with aqueous 10% NaCl solution, dried over Na$_2$SO$_4$ and evaporated under reduced pressure. Purification by flash-chromatography on silicagel (Hexane/EtOAc 1:1) gave 359 mg (100%) of a 1:1 mixture of (2S,4R)-1-(Naphthalene-2-sulfonyl)-4-tritylsulfanyl-pyrrolidine-2-carboxylic acid [1-(4-methoxy-benzyl)-1H- and [2-(4-methoxy-benzyl)-2H-tetrazol-5-ylmethyl]-methyl-amide, MS: 795 (MH$^+$).

A solution of 150 mg (0.19 mmol) of a 1:1 mixture of (2S,4R)-1-(Naphthalene-2-sulfonyl)-4-tritylsulfanyl-pyrrolidine-2-carboxylic acid [1-(4-methoxy-benzyl)-1H- and [2-(4-methoxy-benzyl)-2H-tetrazol-5-ylmethyl]-methyl-amide in 10 ml TFA was treated with 0.3 ml (1.9 mmol) triethylsilane, refluxed for 7 min at 80° C. and evaporated. Crystallization from CH$_2$Cl$_2$/Et$_2$O gave 46 mg (57%) (2S,4R)-4-Mercapto-1-(naphthalene-2-sulfonyl)-pyrrolidine-2-carboxylic acid methyl-(1H-tetrazol-5-ylmethyl)-amide, mp: 175 slow dec., MS: 433 (MH$^+$).

In analogy:
A 1:1 mixture of (2S,4R)-1-(naphthalene-2-sulfonyl)-4-tritylsulfanyl-pyrrolidine-2-carboxylic acid 1-(4-methoxy-benzyl)-1H- and [2-(4-methoxy-benzyl)-2H-tetrazol-5-ylmethyl]-amide and benzylbromide gave (2S,4R)-4-Mercapto-1-(naphthalene-2-sulfonyl)-pyrrolidine-2-carboxylic acid benzyl-(1H-tetrazol-5-ylmethyl)-amide, mp: 152–155° C. dec., MS: 509 (MH$^+$);

(2S,4R)-1-Methanesulfonyl-4-tritylsulfanyl-pyrrolidine-2-carboxylic acid (1H-tetrazol-5-ylmethyl)-amide gave via the 1:1 Mixture of (2S,4R)-1-methanesulfonyl-4-tritylsulfanyl-pyrrolidine-2-carboxylic acid [1-(4-methoxy-benzyl)-1H- and [2-(4-methoxy-benzyl)-2H-tetrazol-5-ylmethyl]-amide with benzylbromide (2S,4R)-4-Mercapto-1-methanesulfonyl-pyrrolidine-2-carboxylic acid benzyl-(1H-tetrazol-5-ylmethyl)-amide, MS: 397 (MH$^+$).

Example 14

Alkylation of MeSO$_2$ amides

A solution of 138 mg (0.4 mmol) (2S,4R)-1-Methanesulfonyl-4-(4-methoxy-benzylsulfanyl)-pyrrolidine-2-carboxylic acid in 8 ml THF was treated at −78° C. with 0.83 ml (1.24 mmol, 1.5 M THF solution) of LDA. After 30 min 0.17 ml (1.4 mmol) benzylbromide were added and warmed up to RT over night. The reaction was poured into aqueous 10% KHSO$_4$/EtOAc (3×). The organic phases were washed with aqueous 10% NaCl solution and dried over Na$_2$SO$_4$ to give 242 mg (quantitativ) crude (2S,4R)-4-(4-Methoxy-benzylsulfanyl)-1-(2-phenyl-ethanesulfonyl)-pyrrolidine-2-carboxylic acid.

A solution of 242 mg (0.4 mmol) (2S,4R)-4-(4-Methoxy-benzylsulfanyl)-1-(2-phenyl-ethanesulfonyl)-pyrrolidine-2-carboxylic acid in 4 ml THF was treated at 0° C. with 0.057 ml (0.44 mmol) N-benzylmethylamine, 92 mg (0.48 mmol) EDCI, 6.1 mg (0.04 mmol) HOBT and warmed up over night to RT. The reaction was poured into aqueous 10% KHSO$_4$/EtOAc (3×). The organic phases were washed with aqueous 10% NaCl solution and dried over Na$_2$SO$_4$ to give after flash silicagel column (Hexane/EtOAc 4:1) 21 mg (10%) (2S,4R)-4-(4-Methoxy-benzylsulfanyl)-1-(2-phenyl-ethanesulfonyl)-pyrrolidine-2-carboxylic acid benzyl-methyl-amide, MS: 539 (MH$^+$).

Following Method 9.1., (2S,4R)-4-(4-Methoxy-benzylsulfanyl)-1-(2-phenyl-ethanesulfonyl)-pyrrolidine-2-carboxylic acid benzyl-methyl-amide gave (2S,4R)-4-Mercapto-1-(2-phenyl-ethanesulfonyl)-pyrrolidine-2-carboxylic acid benzyl-methyl-amide, MS: 419 (MH$^+$).

In analogy to the example above, deprotonation of (2S,4R)-1-Methanesulfonyl-4-(4-methoxy-benzylsulfanyl)-pyrrolidine-2-carboxylic acid with LiHMDS and alkylation with benzylbromide gave after EDCI/HOBT coupling with N-benzylamine (2S,4R)-1-(1,3-Diphenyl-propane-2-sulfonyl)-4-(4-methoxy-benzylsulfanyl)-pyrrolidine-2-carboxylic acid benzyl-methyl-amide in 7% yield, MS: 629 (MH$^+$).

Following Method 9.1., (2S,4R)-1-(1,3-Diphenyl-propane-2-sulfonyl)-4-(4-methoxy-benzylsulfanyl)-pyrrolidine-2-carboxylic acid benzyl-methyl-amide gave (2S,4R)-1-(1,3-Diphenyl-propane-2-sulfonyl)-4-mercapto-pyrrolidine-2-carboxylic acid benzyl-methyl-amide, MS: 509 (MH$^+$).

Example 15

Starting from Disulfid-diacids: (2S,2'S,3S,3S')-3,3'-Disulfanediyl-bis-pyrrolidine-1,2-dicarboxylic acid 1,1'-di-tert-butyl ester g (2.03 mmol) (2S,2'S,3S,3S')-3,3'-Disulfanediyl-bis-pyrrolidine-1,2-dicarboxylic acid 1,1'-di-tert-butyl ester in 50 ml CH$_2$Cl$_2$ was treated with 0.45 ml (4.08 mmol, 2 eq) NMM, 0.63 ml (4.09 mmol, 2 eq) piperidine-4-carboxylic acid ethyl ester and 1.5 g (5.05 mmol, 2.5 eq) TPTU at RT over night. The solution was diluted with CH$_2$Cl$_2$, washed with 1 M KHSO$_4$, 5% NaHCO$_3$, brine and was dried over Na$_2$SO$_4$. Column chromatography yielded 1.24 g (79%) 1-[(2S,4R)-4-[(3R,5S)-5-(4-ethoxycarbonyl-piperidine-1-carbonyl)-pyrrolidin-3-yldisulfanyl]-pyrrolidine-2-carbonyl]-piperidine-4-carboxylic acid 4-ethyl ester as white crystals.

200 mg (0.26 mmol) 1-[(2S,4R)-4-[(3R,5S)-5-(4-ethoxycarbonyl-piperidine-1-carbonyl)-pyrrolidin-3-yldisulfanyl]-pyrrolidine-2-carbonyl]-piperidine-4-carboxylic acid 4-ethyl ester were treated according to general procedure 3.1. to give 1-[(2S,4R)-4-[(3R,5S)-5-(4-ethoxycarbonyl-piperidine-1-carbonyl)-pyrrolidin-3-yldisulfanyl]-pyrrolidine-2-carbonyl]-piperidine-4-carboxylic acid 4-ethyl ester which was dissolved in 10 ml CH$_2$Cl$_2$ and treated with 176 mg (0.78 mmol, 3eq) 2-naphthalene sulfonylchloride and 95 mg (0.78 mmol, 3 eq) DMAP at RT for 30 min. The reaction mixture was poured on 1M KHSO$_4$ and CH$_2$Cl$_2$.

The organic phase was washed with brine, dried over Na$_2$SO$_4$ and purified by flash chromatography yielding 174 mg (70%) 1-[(2S,4R)-4-[(3R,5S)-5-(4-ethoxycarbonyl-piperidine-1-carbonyl)-1-(naphthalene-2-sulfonyl)-pyrrolidin-3-yldisulfanyl]-1-(naphthalene-2-sulfonyl)-pyrrolidine-2-carbonyl]-piperidine-4-carboxylic acid 4-ethyl ester as white solid, MS: 951 (MH$^+$).

Disulfide cleavage of 174 mg (0.18 mmol) 1-[(2S,4R)-4-[(3R,5S)-5-(4-ethoxycarbonyl-piperidine-1-carbonyl)-1-(naphthalene-2-sulfonyl)-pyrrolidin-3-yldisulfanyl]-1-(naphthalene-2-sulfonyl)-pyrrolidine-2-carbonyl]-piperidine-4-carboxylic acid 4-ethyl ester according to general procedure 4.1. gave 153 mg (88%) (2S,4S)-1-[4-mercapto-1-(naphthalene-2-sulfonyl)-pyrrolidine-2-carbonyl]-piperidine-4-carboxylic acid ethyl ester as white solid, MS: 475 (M-H)⁻.

Treatment of (2S,4S)-1-[4-mercapto-1-(naphthalene-2-sulfonyl)-pyrrolidine-2-carbonyl]-piperidine-4-carboxylic acid ethyl ester with LiOH according to 5.2. gave (2S,4S)-1-[4-Mercapto-1-(naphthalene-2-sulfonyl)-pyrrolidine-2-carbonyl]-piperidine-4-carboxylic acid as white lyoph. solid, MS: 449 (MH⁺).

Analogously, the following compounds were prepared from 1-[(2S,4R)-4-[(3R,5S)-5-(4-ethoxycarbonyl-piperidine-1-carbonyl)-pyrrolidin-3-yldisulfanyl]-pyrrolidine-2-carbonyl]-piperidine-4-carboxylic acid 4-ethyl ester and 4-t-butyl benzenesulfonyl chloride, 5-dimethylamino naphthalene 1-sulfonyl chloride and 1-naphthylsulfonyl chloride, respectively:

(2S,4S)-1-[1-(4-tert-Butyl-benzenesulfonyl)-4-mercapto-pyrrolidine-2-carbonyl]-piperidine-4-carboxylic acid ethyl ester as white solid, MS: 483 (MH⁺);

(2S,4S)-1-[1-(5-Dimethylamino-naphthalene-1-sulfonyl)-4-mercapto-pyrrolidine-2-carbonyl]-piperidine-4-carboxylic acid ethyl ester as yellow solid, MS: 520 (MH⁺);

(2S,4S)-1-[4-Mercapto-1-(naphthalene-1-sulfonyl)-pyrrolidine-2-carbonyl]-piperidine-4-carboxylic acid ethyl ester as colorless oil, MS: 477 (MH⁺).

Treatment of (2S,4S)-1-[1-(5-Dimethylamino-naphthalene-1-sulfonyl)-4-mercapto-pyrrolidine-2-carbonyl]-piperidine-4-carboxylic acid ethyl ester with LiOH according to 5.2. gave (2S,4S)-1-[1-(5-Dimethylamino-naphthalene-1-sulfonyl)-4-mercapto-pyrrolidine-2-carbonyl]-piperidine-4-carboxylic acid as yellow solid MS: 492 (MH⁺).

Formation of Urea as final product.

180 mg (0.31 mmol) 1-[(2S,4R)-4-[(3R,5S)-5-(4-Ethoxycarbonyl-piperidine-1-carbonyl)-pyrrolidin-3-yldisulfanyl]- pyrrolidine-2-carbonyl]-piperidine-4-carboxylic acid 4-ethyl ester in 5 ml toluene were treated with 82 mg (0.69 mmol, 2.02 eq) phenylisocyanate and 70 mg (0.69 mmol, 2.2 eq) NMM. The mixture was stirred at RT for 2 h, placed in the freezer and the crystals were isolated by filtration and were washed with toluene. The crude product was subjected to disulfide cleavage according to 4.1. to give 200 mg (77%) (2S,4S)-1-(4-Mercapto-1-phenylcarbamoyl-pyrrolidine-2-carbonyl)-piperidine-4-carboxylic acid ethyl ester as white solid, MS: 405 (M).

In analogy to the examples above, the following compounds were prepared from (2S,2'S,3S,3S')-3,3'-Disulfanediyl-bis-pyrrolidine-1,2-dicarboxylic acid 1,1'-di-tert-butyl ester with ethyl-4-amino-benzoate followed by BOC-cleavage (3.1.) via 4-[[(2S,4S)-4-[(3S,5S)-5-(4-Ethoxycarbonyl-phenylcarbamoyl)-pyrrolidin-3-yldisulfanyl]-pyrrolidine-2-carbonyl]-amino]-benzoic acid ethyl ester as beige solid, MS: 587 (MH⁺), followed by treatment with naphtoyl chloride (2.2.), 4-tert-butyl-benzenesulfonyl chloride, 4-n-butoxybenzene sulfonylchloride, 2-methoxycarbonylbenzene sulfonylchoride, 4-biphenyl sullfonylchloride, 1-butane sulfonyl chloride, 3,4-dimethoxybenzene sulfonylchloride (2.1.), respectively, followed by disulfide cleavage according to (4.1.) gave:

(2S,4S)-4-[[4-mercapto-1-(naphthalene-2-carbonyl)-pyrrolidine-2-carbonyl]-amino]-benzoic acid ethyl ester as white solid, MS: 449 (MH⁺);

(2S,4S)-4-[[1-(4-tert-butyl-benzenesulfonyl)-4-mercapto-pyrrolidine-2-carbonyl]-amino]-benzoic acid ethyl ester as white solid, MS: 489 (M-H)⁻(MH⁻).

(2S,4S)-4-[[1-(4-butoxy-benzenesulfonyl)-4-mercapto-pyrrolidine-2-carbonyl]-amino]-benzoic acid ethyl ester as white amorphous, MS: 507 (MH⁺);

(2S,4S)-4-[[4-mercapto-1-(2-methoxycarbonyl-benzenesulfonyl)-pyrrolidine-2-carbonyl]-amino]-benzoic acid ethyl ester as white amorphous, MS: 493 (MH⁺);

(2S,4S)-4-[[1-(biphenyl-4-sulfonyl)-4-mercapto-pyrrolidine-2-carbonyl]-amino]-benzoic acid ethyl ester as white amorphous, MS: 511 (MH⁺);

(2S,4S)-4-[[1-(butane-1-sulfonyl)-4-mercapto-pyrrolidine-2-carbonyl]-amino]-benzoic acid ethyl ester as white amorphous, MS: 415 (MH⁺);

(2S,4S)-4-[[1-(3,4-dimethoxy-benzenesulfonyl)-4-mercapto-pyrrolidine-2-carbonyl]-amino]-benzoic acid ethyl ester as white amorphous, MS: 495 (MH⁺);

Analogously, the following compounds were prepared from (2S,2'S,3S,3S')-3,3'-Disulfanediyl-bis-pyrrolidine-1,2-dicarboxylic acid 1,1'-di-tert-butyl ester with 4-(2-Methylamino-acetylamino)-benzoic acid ethyl ester followed by BOC-cleavage (3.1.), treatment with 2-naphthalene sulfonyl chloride, 8-quinoline sulfonyl chloride, alpha-toluene sulfonyl chloride, trans-beta-styrene sulfonyl chloride, propane-2-sulfonyl chloride, respectively, and disulfide cleavage (4.1.):

(2S,4S)-4-(2-[[4-Mercapto-1-(naphthalene-2-sulfonyl)-pyrrolidine-2-carbonyl]-methyl-amino]-acetylamino)-benzoic acid ethyl ester as white solid, MS: 554 (M-H)⁻;

(2S,4S)-4-[2-[[4-Mercapto-1-(quinoline-8-sulfonyl)-pyrrolidine-2-carbonyl]-methyl-amino]-acetylamino]-benzoic acid ethyl ester as white solid, MS: 557 (MH⁺);

(2S,4S)-4-[2-[(4-Mercapto-1-phenylmethanesulfonyl-pyrrolidine-2-carbonyl)-methyl-amino]-acetylamino]-benzoic acid ethyl ester as white solid, MS: 520 (MH⁺);

(2S,4S)-4-[2-[[4-Mercapto-1-(2-phenyl-ethenesulfonyl)-pyrrolidine-2-carbonyl]-methyl-amino]-acetylamino]-benzoic acid ethyl ester as white solid, MS: 532 (MH⁺);

(2S,4S)-4-[2-[[4-Mercapto-1-(propane-2-sulfonyl)-pyrrolidine-2-carbonyl]-methyl-amino]-acetylamino]-benzoic acid ethyl ester as white solid, MS: 471 (MH⁺).

Analogously, the following compounds were prepared from (2S,2'S,3S,3S')-3,3'-Disulfanediyl-bis-pyrrolidine-1,2-dicarboxylic acid 1,1'-di-tert-butyl ester with 4-(2-Methylamino-acetylamino)-benzoic acid ethyl ester, followed by BOC-cleavage (3.1.), treatment with 8-quinoline sulfonyl chloride, alpha-toluene sulfonyl chloride, trans-beta-styrene sulfonyl chloride, respectively, and ester cleavage with LiOH according to procedure (5.1.) and disulfide cleavage (4.1.):

(2S,4S)-4-[2-[[4-Mercapto-1-(quinoline-8-sulfonyl)-pyrrolidine-2-carbonyl]-methyl-amino]-acetylamino]-benzoic acid as white solid, MS: 529 (MH⁺);

(2S,4S)-4-[2-[(4-Mercapto-1-phenylmethanesulfonyl-pyrrolidine-2-carbonyl)-methyl-amino]-acetylamino]-benzoic acid as white solid, MS: 492 (MH⁺);

(2S,4S)-4-[2-[[4-Mercapto-1-(2-phenyl-ethenesulfonyl)-pyrrolidine-2-carbonyl]-methyl-amino]-acetylamino]-benzoic acid as white solid, MS: 504 (MH⁺).

Analogously, the following compound was prepared from (2S,2'S,3S,3S')-3,3'-Disulfanediyl-bis-pyrrolidine-1,2-dicarboxylic acid 1,1'-di-tert-butyl ester with N-Benzylmethylamine, followed by BOC-cleavage (3.1.), treatment 2-Naphtalenesulfonyl chloride and disulfide cleavage (4.1.):

(2S,4S)-4-Mercapto-1-(naphthalene-2-sulfonyl)-pyrrolidine-2-carboxylic acid benzyl-methyl-amide as white solid, MS: 441 (MH$^+$).

The following compounds were prepared from (2S,2'S,3S,3S')-3,3'-Disulfanediyl-bis-pyrrolidine-1,2-dicarboxylic acid 1,1'-di-tert-butyl ester by treatment with ethyl-4-amino benzoate according to 1.2., followed by BOC hydrolysis according to 3.1. and treatment with 2-naphthalenesulfonyl chloride, phenylmethanesulfonyl chloride, 4-methoxybenzenesulfonyl chloride, 2-thiophenesulfonyl chloride (2.1.), respectively, followed by disulfide cleavage according to general procedure 4.1.:

(2S,4S)-4-[[4-Mercapto-1-(naphthalene-2-sulfonyl)-pyrrolidine-2-carbonyl]-amino]-benzoic acid ethyl ester as white solid, MS: 483 (M-H)$^-$;

(2S,4S)-4-[(4-Mercapto-1-phenylmethanesulfonyl-pyrrolidine-2-carbonyl)-amino]-benzoic acid ethyl ester as white lyoph solid, MS: 447 (M-H)$^-$;

(2S,4S)-4-{[4-Mercapto-1-(4-methoxy-benzenesulfonyl)-pyrrolidine-2-carbonyl]-amino}-benzoic acid ethyl ester as white solid, MS: 463 (M-H)$^-$;

(2S,4S)-4-{[4-Mercapto-1-(thiophene-2-sulfonyl)-pyrrolidine-2-carbonyl]-amino}-benzoic acid ethyl ester as white solid, MS: 441 (MH$^+$).

The following compound was prepared from (2S,2'S,3S,3S')-3,3'-Disulfanediyl-bis-pyrrolidine-1,2-dicarboxylic acid 1,1'-di-tert-butyl ester by treatment with methyl benzylamine according to 1.2., followed by BOC hydrolysis according to 3.1., and treatment with 4-tert-butyl-benzenesulfonyl chloride (2.1.), followed by disulfide cleavage according to general procedure 4.1.

(2S,4S)-1-(4-tert-Butyl-benzenesulfonyl)-4-mercapto-pyrrolidine-2-carboxylic acid benzyl-methyl-amide as white solid, MS: 447 (MH$^+$).

The following compounds were prepared from (2S,2'S,3S,3S')-3,3'-Disulfanediyl-bis-pyrrolidine-1,2-dicarboxylic acid 1,1'-di-tert-butyl ester by treatment with ethyl-piperidine-4-carboxylate according to 1.2., followed by BOC hydrolysis according to 3. 1., and treatment with 4-tert-butyl benzoyl chloride (2.2.), 4-methoxybenzenesulfonyl chloride, phenylmethanesulfonyl chloride and 2-thiophenesulfonyl chloride (2.1.), respectively, followed by disulfide cleavage according to general procedure 4.1.:

(2S,4S)-1-[1-(4-tert-Butyl-benzoyl)-4-mercapto-pyrrolidine-2-carbonyl]-piperidine-4-carboxylic acid ethyl ester as white solid, MS: 447 (MH$^+$);

(2S,4S)-1-[4-Mercapto-1-(4-methoxy-benzenesulfonyl)-pyrrolidine-2-carbonyl]-piperidine-4-carboxylic acid ethyl ester as white solid, MS: 457 (MH$^+$);

(2S,4S)-1-(4-Mercapto-1-phenylmethanesulfonyl-pyrrolidine-2-carbonyl)-piperidine-4-carboxylic acid ethyl ester as white solid, MS: 441 (MH$^+$);

(2S,4S)-1-[4-Mercapto-1-(thiophene-2-sulfonyl)-pyrrolidine-2-carbonyl]-piperidine-4-carboxylic acid ethyl ester as white solid, MS: 433 (MH$^+$).

Example 16

Tyrosine-derivatives

Analogously, the following intermediate was prepared from (2S,2'S,3S,3S')-3,3'-Disulfanediyl-bis-pyrrolidine-1,2-dicarboxylic acid 1,1'-di-tert-butyl ester and L-tyrosine-methyl ester•hydrochloride, followed by BOC-cleavage (3.1.): (S)-3-(4-Hydroxy-phenyl)-2-[[(2S,4R)-4-[(3R,5S)-5-[(S)-2-(4-hydroxy-phenyl)-1-methoxycarbonyl-ethylcarbamoyl]-pyrrolidin-3-yldisulfanyl]-pyrrolidine-2-carbonyl]-amino]-propionic acid methyl ester as beige amorphous, MS: 647 (MH$^+$).

230 mg (0.35 mmol) (S)-3-(4-Hydroxy-phenyl)-2-[[(2S,4R)-4-[(3R,5S)-5-[(S)-2-(4-hydroxy-phenyl)-1-methoxycarbonyl-ethylcarbamoyl]-pyrrolidin-3-yldisulfanyl]-pyrrolidine-2-carbonyl]-amino]-propionic acid methyl ester were treated with 248 mg (1.06 mmol, 3 eq) 4-tert-butylbenzene sulfonyl chloride and 130 mg (1.03 mmol) DMAP in 6 ml CH$_2$Cl$_2$ at RT for 48 h. The solution was concentrated and the crude product subjected to disulfide cleavage according to 4.1. followed by column chromatography to give:

(S)-2-[[(2S,4S)-1-(4-tert-Butyl-benzenesulfonyl)-4-mercapto-pyrrolidine-2-carbonyl]-amino]-3-(4-hydroxy-phenyl)-propionic acid methyl ester as white solid, MS: 521 (MH$^+$) and (S)-2-[[(2S,4S)-1-(4-tert-Butyl-benzenesulfonyl)-4-mercapto-pyrrolidine-2-carbonyl]-amino]-3-[4-(4-tert-butyl-benzenesulfonyloxy)-phenyl]-propionic acid methyl ester as colorless amorphous, MS: 717 (MH$^+$).

Analogously, with 1-naphthalene sulfonylchloride:

(S)-3-(4-Hydroxy-phenyl)-2-[[(2S,4S)-4-mercapto-1-(naphthalene-1-sulfonyl)-pyrrolidine-2-carbonyl]-amino]-propionic acid methyl ester as colorless amorphous, MS: 515 (MH$^+$);

(S)-2-[[(2S,4S)-4-Mercapto-1-(naphthalene-1-sulfonyl)-pyrrolidine-2-carbonyl]-amino]-3-[4-(naphthalene-1-sulfonyloxy)-phenyl]-propionic acid methyl ester as colorless amorphous, MS: 705 (MH$^+$);

with 1-biphenyl-4-sulfonyl chloride:

(S)-2-[[(2S,4S)-1-(Biphenyl-4-sulfonyl)-4-mercapto-pyrrolidine-2-carbonyl]-amino]-3-(4-hydroxy-phenyl)-propionic acid methyl ester as white solid, MS: 541 (MH$^+$);

(S)-2-[[(2S,4S)-1-(Biphenyl-4-sulfonyl)-4-mercapto-pyrrolidine-2-carbonyl]-amino]-3-[4-(biphenyl-4-sulfonyloxy)-phenyl]-propionic acid methyl ester as white amorph freez, MS: 757 (MH$^+$);

with 4-butoxy-benzenesulfonyl chloride:

(S)-2-[[(2S,4S)-1-(4-Butoxy-benzenesulfonyl)-4-mercapto-pyrrolidine-2-carbonyl]-amino]-3-(4-hydroxy-phenyl)-propionic acid methyl ester as white solid, MS: 537 (MH$^+$);

(S)-2-[[(2S,4S)-1-(4-Butoxy-benzenesulfonyl)-4-mercapto-pyrrolidine-2-carbonyl]-amino]-3-[4-(4-butoxy-benzenesulfonyloxy)-phenyl]-propionic acid methyl ester as colorless amorphous, MS: 749 (MH$^+$);

with 3,4-dimethoxy-benzenesulfonyl chloride:

(S)-2-[[(2S,4S)-1-(3,4-Dimethoxy-benzenesulfonyl)-4-mercapto-pyrrolidine-2-carbonyl]-amino]-3-(4-hydroxy-phenyl)-propionic acid methyl ester as white solid, MS: 525 (MH$^+$);

(S)-2-[[(2S,4S)-1-(3,4-Dimethoxy-benzenesulfonyl)-4-mercapto-pyrrolidine-2-carbonyl]-amino]-3-[4-(3,4-dimethoxy-benzenesulfonyloxy)-phenyl]-propionic acid methyl ester as colorless amorphous, MS: 742 (MNH$_4^+$);

with butane-1-sulfonyl chloride:

(S)-2-[[(2S,4S)-1-(Butane-1-sulfonyl)-4-mercapto-pyrrolidine-2-carbonyl]-amino]-3-(4-hydroxy-phenyl)-propionic acid methyl ester as white solid, MS: 462 (MNH$_4^+$);

with 2-methoxycarbonyl benzene sulfonyl chloride: 2-[(2S,4S)-2-[(S)-2-(4-Hydroxy-phenyl)-1-methoxycarbonyl-ethylcarbamoyl]-4-mercapto-pyrrolidine-1-sulfonyl]-benzoic acid methyl ester as white crystalline, MS: 523 (MH$^+$).

with 2-naphthoyl chloride:
Naphthalene-2-carboxylic acid 4-[(S)-2-[[(2S,4S)-4-mercapto-1-(naphthalene-2-carbonyl)-pyrrolidine-2-carbonyl]-amino]-2-methoxycarbonyl-ethyl]-phenyl ester as white crystalline MS: 633 (MH$^+$).

Treatment of 2-[(2S,4S)-2-[(S)-2-(4-Hydroxy-phenyl)-1-methoxycarbonyl-ethylcarbamoyl]-4-mercapto-pyrrolidine-1-sulfonyl]-benzoic acid methyl ester according to general procedure 5.2. yielded 2-[(2S,4S)-2-[(S)-1-Carboxy-2-(4-hydroxy-phenyl)-ethylcarbamoyl]-4-mercapto-pyrrolidine-1-sulfonyl]-benzoic acid methyl ester as white solid, MS: 509 (MH$^+$).

Example 17

(2S,4S)-4-[(3S,5S)-5-carboxy-1-(naphthalene-2-sulfonyl)-pyrrolidin-3-yldisulfanyl]-1-(naphthalene-2-sulfonyl)-pyrrolidine-2-carboxylic Acid as Educt To 400 mg (0.59 mmol) (2S,4S)-4-[(3S,5S)-5-carboxy-1-(naphthalene-2-sulfonyl)-pyrrolidin-3-yldisulfanyl]-1-(naphthalene-2-sulfonyl)-pyrrolidine-2-carboxylic acid in 9 ml CH$_2$Cl$_2$ were added 220 mg (2.6 mmol, 2.2 eq) 4-methyl morpholine, followed by 440 mg (1.48 mmol, 1.25 eq) TPTU and 220 mg (1.3 mmol, 1.1 eq) L-valine methyl ester•hydrochloride. The solution was shaken at RT over night. The solution was concentrated and the crude product was purified by flash chromatography yielding 520 mg (98%) (S)-2-{[(2S,4S)-4-[(3S,5S)-5-((S)-1-Methoxycarbonyl-2-methyl-propylcarbamoyl)-1-(naphthalene-2-sulfonyl)-pyrrolidin-3-yldisulfanyl]-1-(naphthalene-2-sulfonyl)-pyrrolidine-2-carbonyl]-amino}-3-methyl-butyric acid methyl ester as white foam which was subjected to disulfide cleavage according to general procedure 4.1. to give (S)-2-[[(2S,4S)-4-Mercapto-1-(naphthalene-2-sulfonyl)-pyrrolidine-2-carbonyl]-amino]-3-methyl-butyric acid methyl ester as colorless foam, MS: 451 (MH$^+$).

(S)-2-[[(2S,4S)-4-Mercapto-1-(naphthalene-2-sulfonyl)-pyrrolidine-2-carbonyl]-amino]-3-methyl-butyric acid methyl ester was treated with 0.1M LiOH according to general procedure 5.2. to yield (S)-2-[[(2S,4S)-4-Mercapto-1-(naphthalene-2-sulfonyl)-pyrrolidine-2-carbonyl]-amino]-3-methyl-butyric acid as white foam, MS: 437 (MH$^+$).

Analogously the following compounds were prepared from (2S,4S)-4-[(3S,5S)-5-carboxy-1-(naphthalene-2-sulfonyl)-pyrrolidin-3-yldisulfanyl]-1-(naphthalene-2-sulfonyl)-pyrrolidine-2-carboxylic acid and β-alanine ethyl ester•hydrochloride, L-proline methylester•hydrochloride, L-tyrosine methyl ester-hydrochloride, L-methionine methyl ester·hydrochloride, 3,4-(methylenedioxy)aniline, methyl-4-hydroxy-L-prolinate•hydrochloride, piperonylamine, ethyl-(4-aminophenyl)acetate, ethyl anthranilate, ethyl-3-aminobenzoate•methanesulfonate, 4-aminobenzyl alcohol, D,L-ethyl pipecolinate, ethyl nipecotate, p-anisidine, 4-hydroxypiperidine, (Piperidin-4-yloxy)-acetic acid tert-butyl ester, L-tryptophan methyl ester·hydrochloride, 2-amino-1,3-propandiol, respectively:
(2S,4S)-3-[[4-Mercapto-1-(naphthalene-2-sulfonyl)-pyrrolidine-2-carbonyl]-amino]-propionic acid ethyl ester as white solid, MS: 437 (MH$^+$);
(S)-1-[(2S,4S)-4-Mercapto-1-(naphthalene-2-sulfonyl)-pyrrolidine-2-carbonyl]-pyrrolidine-2-carboxylic acid methyl ester as white solid, MS: 449 (MH$^+$);
(S)-3-(4-Hydroxy-phenyl)-2-[[(2S,4S)-4-mercapto-1-(naphthalene-2-sulfonyl)-pyrrolidine-2-carbonyl]-amino]-propionic acid methyl ester as white solid, MS: 515 (MH$^+$) via (S)-3-(4-Hydroxy-phenyl)-2-{[(2S,4S)-4-[(3S,5S)-5-[(S)-2-(4-hydroxy-phenyl)-1-methoxycarbonyl-ethylcarbamoyl]-1-(naphthalene-2-sulfonyl)-pyrrolidin-3-yldisulfanyl]-1-(naphthalene-2-sulfonyl)-pyrrolidine-2-carbonyl]-amino}-propionic acid methyl ester;
(S)-2-[[(2S,4S)-4-Mercapto-1-(naphthalene-2-sulfonyl)-pyrrolidine-2-carbonyl]-amino]-3-methyl-butyric acid methyl ester as colorless foam, MS: 451 (MH$^+$);
(S)-2-(2S,4S)-4-Mercapto-1-(naphthalene-2-sulfonyl)-pyrrolidine-2-carbonyl]-amino]-4-methylsulfanyl-butyric acid methyl ester as colorless gum, MS: 483 (MH$^+$);
(2S,4S)-4-Mercapto-1-(naphthalene-2-sulfonyl)-pyrrolidine-2-carboxylic acid benzo[1,3]dioxol-5-ylamide as light pink solid, MS: 457 (MH$^+$);
(2S,4R)-4-Hydroxy-1-[(2S,4S)-4-mercapto-1-(naphthalene-2-sulfonyl)-pyrrolidine-2-carbonyl]-pyrrolidine-2-carboxylic acid methyl ester as white solid, MS: 465 (MH$^+$);
(2S,4S)-4-Mercapto-1-(naphthalene-2-sulfonyl)-pyrrolidine-2-carboxylic acid (benzo[1,3]dioxol-5-ylmethyl)-amide as white solid, MS: 471 (MH$^+$);
(2S,4S)-[4-[[4-Mercapto-1-(naphthalene-2-sulfonyl)-pyrrolidine-2-carbonyl]-amino]-phenyl]-acetic acid ethyl ester as white solid, MS: 499 (MH$^+$);
(2S,4S)-2-[[4-Mercapto-1-(naphthalene-2-sulfonyl)-pyrrolidine-2-carbonyl]-amino]-benzoic acid ethyl ester as white solid, MS: 485 (MH$^+$);
(2S,4S)-3-[[4-Mercapto-1-(naphthalene-2-sulfonyl)-pyrrolidine-2-carbonyl]-amino]-benzoic acid ethyl ester as white solid, MS: 485 (MH$^+$);
(2S,4S)-4-Mercapto-1-(naphthalene-2-sulfonyl)-pyrrolidine-2-carboxylic acid (4-hydroxymethyl-phenyl)-amide as white solid, MS: 443 (MH$^+$);
Mixture of (R)- and (S)-1-[(2S,4S)-4-mercapto-1-(naphthalene-2-sulfonyl)-pyrrolidine-2-carbonyl]-piperidine-2-carboxylic acid ethyl ester as colorless gum, MS: 477 (MH$^+$);
Mixture of (R)- and (S)-1-[(2S,4S)-4-mercapto-1-(naphthalene-2-sulfonyl)-pyrrolidine-2-carbonyl]-piperidine-3-carboxylic acid ethyl ester as colorless gum, MS: 477 (MH$^+$);
(2S,4S)-4-Mercapto-1-(naphthalene-2-sulfonyl)-pyrrolidine-2-carboxylic acid (4-methoxy-phenyl)-amide as white solid, MS: 443 (MH$^+$);
(2S,4S)-(4-Hydroxy-piperidin-1-yl)-[4-mercapto-1-(naphthalene-2-sulfonyl)-pyrrolidin-2-yl]-methanone as white solid, MS: 421 (MH$^+$);
(2S,4S)-[1-[4-Mercapto-1-(naphthalene-2-sulfonyl)-pyrrolidine-2-carbonyl]-piperidin-4-yloxy]-acetic acid tert-butyl ester as white solid, MS: 535 (MH$^+$);
(S)-3-(1H-Indol-3-yl)-2-[[(2S,4S)-4-mercapto-1-(naphthalene-2-sulfonyl)-pyrrolidine-2-carbonyl]-amino]-propionic acid methyl ester as white solid, MS: 538 (MH$^+$);
(2S,4S)-4-Mercapto-1-(naphthalene-2-sulfonyl)-pyrrolidine-2-carboxylic acid (2-hydroxy-1-hydroxymethyl-ethyl)-amide as white solid, MS: 411 (MH$^+$);
Preparation of the Corresponding Acids:
Analogously, the following compounds (acids) were prepared from (2S,4S)-4-(3S,5S)-5-Carboxy-1-(naphthalene-2-sulfonyl)-pyrrolidin-3-yldisulfanyl]-1-(naphthalene-2-sulfonyl)-pyrrolidine-2-carboxylic acid and β-alanine ethyl ester•hydrochloride, L-proline methylester•hydrochloride, L-tyrosine methyl ester·hydrochloride, L-methionine methyl ester•hydrochloride, methyl-4-hydroxy-L- prolinate•hydrochloride, ethyl-(4-aminophenyl)acetate, ethyl anthranilate, ethyl-3-aminobenzoate methanesulfonate, D,L-ethyl pipecolinate, ethyl nipecotate, respectively, followed by disulfide cleavage (4.1.) and ester hydrolysis (5.2.) as described above:

(2S,4S)-3-[[4-Mercapto-1-(naphthalene-2-sulfonyl)-pyrrolidine-2-carbonyl]-amino]-propionic acid as white solid, MS: 409 (MH$^+$);

(S)-1-[(2S,4S)-4-Mercapto-1-(naphthalene-2-sulfonyl)-pyrrolidine-2-carbonyl]-pyrrolidine-2-carboxylic acid as white solid, MS: 435 (MH$^+$);

(S)-3-(4-Hydroxy-phenyl)-2-[[(2S,4S)-4-mercapto-1-(naphthalene-2-sulfonyl)-pyrrolidine-2-carbonyl]-amino]-propionic acid as white solid, MS: 501 (MH$^+$);

(S)-2-[[(2S,4S)-4-Mercapto-1-(naphthalene-2-sulfonyl)-pyrrolidine-2-carbonyl]-amino]-4-methylsulfanyl-butyric acid as colorless gum, MS: 469 (MH$^+$);

(2S,4R)-4-Hydroxy-1-[(2S,4S)-4-mercapto-1-(naphthalene-2-sulfonyl)-pyrrolidine-2-carbonyl]-pyrrolidine-2-carboxylic acid as white solid, MS: 451 (MH$^+$);

(2S,4S)-[4-[[4-Mercapto-1-(naphthalene-2-sulfonyl)-pyrrolidine-2-carbonyl]-amin]-phenyl]-acetic acid as light yellow solid, MS: 471 (MH$^+$);

(2S,4S)-2-[[4-Mercapto-1-(naphthalene-2-sulfonyl)-pyrrolidine-2-carbonyl]-amino]-benzoic acid as white solid, MS: 457 (MH$^+$);

(2S,4S)-3-[[4-Mercapto-1-(naphthalene-2-sulfonyl)-pyrrolidine-2-carbonyl]-amino]-benzoic acid as white solid, MS: 457 (MH$^+$);

Mixture of (R)- and (S)-1-[(2S,4S)-4-mercapto-1-(naphthalene-2-sulfonyl)-pyrrolidine-2-carbonyl]-piperidine-2-carboxylic acid as white solid, MS: 449 (MH$^+$);

Mixture of (R)- and (S)-1-[(2S,4S)-4-mercapto-1(naphthalene-2-sulfonyl)-pyrrolidine-2-carbonyl]-piperidine-3-carboxylic acid as white solid, MS: 449 (MH$^+$).

243 mg (4.5 mmol) (S)-3-(1H-Indol-3-yl)-2-[[(2S,4S)-4-mercapto-1-(naphthalene-2-sulfonyl)-pyrrolidine-2-carbonyl]-amino]-propionic acid methyl ester in 13.5 ml THF were treated 22.5 ml 0.1M LiOH in the presence of 209 mg (13.5 mmol) DTT at RT for 72h. The solution was acidified with 1MKHSO$_4$KHS04 and the inorganic phase was extracted with EtOAc. The combined organic phases were washed with brine and were dried with Na$_2$SO$_4$. Column chromatography with CH$_2$Cl$_2$:MeOH 9:1, followed by trituration with hexane yielded 204 mg (86%) (S)-3-(1H-Indol-3-yl)-2-[[(2S,4S)-4-mercapto-1-(naphthalene-2-sulfonyl)-pyrrolidine-2-carbonyl]-amino]-propionic acid as white solid, mp 130° C., MS: 522 (M-H)$^-$.

Further Modifications:

192 mg (0.187 mmol) (S)-3-(4-Hydroxy-phenyl)-2-{[(2S,4S)-4-[(3S,5S)-5-[(S)-2-(4-hydroxy-phenyl)1-methoxycarbonyl-ethylcarbamoyl]-1-(naphthalene-2-sulfonyl)-pyrrolidin-3-yldisulfanyl]-1-(naphthalene-2-sulfonyl)-pyrrolidine-2-carbonyl]-amino }-propionic acid methyl ester in 6 ml CH$_2$Cl$_2$ were treated with 107 mg (0.56 mmol, 1.5 eq) 2-naphthoyl chloride and 68 mg (0.56 mmol, 1.5 eq) DMAP at RT for 30 min. The solvent was evaporated and the residue purified by flash chromatography with CH$_2$Cl$_2$:EtOAc 8:1 to yield 218 mg (87%) white foam, which was subjected to disulfide cleavage according to general procedure 4.1. to give Naphthalene-2-carboxylic acid 4-[(S)-2-[[(2S,4S)-4-mercapto-1-(naphthalene-2-sulfonyl)-pyrrolidine-2-carbonyl]-amino]-2-methoxycarbonyl-ethyl]-phenyl ester as white foam, MS: 669 (MH$^+$).

Accordingly, replacing naphthoyl chloride by 4-tert butyl benzoyl chloride gave 4-tert-Butyl-benzoic acid 4-[(S)-2-[[(2S,4S)-4-mercapto-1-(naphthalene-2-sulfonyl)-pyrrolidine-2-carbonyl]-amino]-2-methoxycarbonyl-ethyl]-phenyl ester as white foam, MS: 675 (MH$^+$).

213 mg (0.21 mmol)(S)-3-(4-Hydroxy-phenyl)-2-{[(2S,4S)-4-[(3S,5S)-5-[(S)-2-(4-hydroxy-phenyl)-1-methoxycarbonyl-ethylcarbamoyl]-1-(naphthalene-2-sulfonyl)-pyrrolidin-3-yldisulfanyl]-1-(naphthalene-2-sulfonyl)-pyrrolidine-2-carbonyl]-amino}-propionic acid methyl ester in 6 ml DMF were treated with 54 µl (0.45 mmol, 1.1 eq) benzylbromide in the presence of 172 mg (1.24 mmol, 3 eq) K$_2$CO$_3$ at RT for 1 h. The mixture was filtered and evaporated. Column chromatography with CH$_2$Cl$_2$:EtOAc 8:1-4:1 yielded 93 mg white foam, which was subjected to disulfide cleavage according to general procedure 4.1. to give (S)-3-(4-Benzyloxy-phenyl)-2-[[(2S,4S)-4-mercapto-1-(naphthalene-2-sulfonyl)-pyrrolidine-2-carbonyl]-amino]-propionic acid methyl ester as white foam, MS: 605 (MH$^+$).

Analogously the following compounds were prepared using ethyl bromide and ethyl 2-bromopropionate instead of benzyl bromide:

(S)-3-(4-Ethoxy-phenyl)-2-[[(2S,4S)-4-mercapto-1-(naphthalene-2-sulfonyl)-pyrrolidine-2-carbonyl]-amino]-propionic acid methyl ester as white foam, MS: 543 (MH$^+$);

Mixture of (S)-3-[4-[(R)- and -[(S)-1-Ethoxycarbonyl-ethoxy)-phenyl]-2-[[(2S,4S)-4-mercapto-1-(naphthalene-2-sulfonyl)-pyrrolidine-2-carbonyl]-amino]-propionic acid methyl ester as white foam, MS: 615 (MH$^+$).

Hydrolysis of the Ester Moiety According to General Procedure 5.2. Gave:

(S)-3-(4-Ethoxy-phenyl)-2-[[(2S,4S)-4-mercapto-1-(naphthalene-2-sulfonyl)-pyrrolidine-2-carbonyl]-amino]-propionic acid as white solid, MS: 529 (MH$^+$);

Mixture of (S)-3-[4-[(R)- and -[(S)1-carboxy-ethoxy]-phenyl]-2-[[(2S,4S)-4-mercapto-1-(naphthalene-2-sulfonyl)-pyrrolidine-2-carbonyl]-amino]-propionic acid as white solid, MS: 573 (MH$^+$), respectively.

200 mg (0.19 mmol) (S)-3-(4-Hydroxy-phenyl)-2-{[(2S,4S)-4-[(3S,5S)-5-[(S)-2-(4-hydroxy-phenyl)-1-methoxycarbonyl-ethylcarbamoyl]-1-(naphthalene-2-sulfonyl)-pyrrolidin-3-yldisulfanyl]-1-(naphthalene-2-sulfonyl)-pyrrolidine-2-carbonyl]-amino}-propionic acid methyl ester in 2 ml DMF were treated with 50 µl (0.44 mmol, 1.2 eq) phenyl isocyanate at RT for 48 h. The solution was concentrated and the residue was purified by column chromatography with CH$_2$Cl$_2$:EtOAc 4:1 to give 150 mg white foam, which was subjected to disulfide cleavage according to general procedure 4.1. to give (S)-2-[[(2S,4S)-4-Mercapto-1-(naphthalene-2-sulfonyl)-pyrrolidine-2-carbonyl]-amino]-3-(4-phenylcarbamoyloxy-phenyl)-propionic acid methyl ester as white foam, MS: 634 (MH$^+$).

Accordingly, replacing phenyl isocyanate by 4-methoxyphenyl isocyanate gave:

(S)-2-[[(2S,4S)-4-Mercapto-1-(naphthalene-2-sulfonyl)-pyrrolidine-2-carbonyl]-amino]-3-[4-(4-methoxy-phenylcarbamoyloxy)-phenyl]-propionic acid methyl ester as white foam, MS: 664 (MH$^+$).

Example 18

(2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid as educt To 8.05 g (11.95 mmol) (2S,4R)-4-[(3R,5S)-5-Carboxy-1-(naphthalene-2-sulfonyl)-pyrrolidin-3-yldisulfanyl]-1-

(naphthalene-2-sulfonyl)-pyrrolidine-2-carboxylic acid in 450 ml CH$_2$Cl$_2$ were added 5.8 ml (52.8 mmol, 2.2 eq) 4-methyl morpholine, followed by 8.9 g (29.9 mmol, 1.2 eq) TPTU and 6.19 g (23.9 mmol, 1.0 eq) 2-(2-Methylamino-acetylamino)-benzoic acid methyl ester-hydrochloride. The solution was stirred at RT over night, washed with 1M KHSO$_4$, and 5% aq. NaHCO$_3$ solution and brine, dried over Na$_2$SO$_4$, filtered and evaporated. The crude product was purified by flash chromatography yielding 8.7g (67%) 2-[2-[[(2S,4R)-4-[(3R,5S)-5-[[(2-Methoxycarbonly-phenylcarbamoyl)-methyl]-methyl-carbamoyl]-1-(naphthalene-2-sulfonyl)-pyrrolidin-3-yldisulfanyl]-1-(naphthalene-2-sulfonyl)-pyrrolidine-2-carbonyl]-methyl-amino]-acetylamino]-benzoic acid methyl ester as a white amorphous, (Rf 0.2 EtOAc ), MS: 1098 (MNH$_4$+).

To 7.6 g (7.05 mmol) 2-[2-[[(2S,4R)-4-[(3R,5S)-5-[[(2-Methoxycarbonly-phenylcarbamoyl)-methyl]-methyl-carbamoyl]-1-(naphthalene-2-sulfonyl)-pyrrolidin-3-yldisulfanyl]-1-(naphthalene-2-sulfonyl)-pyrrolidine-2-carbonyl]-methyl-amino]-acetylamino]-benzoic acid methyl ester in 200 ml MeOH was added 1 ml 2M K$_2$CO$_3$ and 2.72 g (17.6 mmol, 1.25 eq) DTT. The solution was stirred at RT for 2 h, the solution was acidified with 1M aq KHSO$_4$ (pH 2) and the inorganic phase was extracted with EtOAc. The combined organic phases were washed with brine, dried over Na$_2$SO$_4$, filtered and evaporated. The crude product was titurated with Et$_2$O to give 6.95 g (91%) (2S,4R)-2-[2-[[4-Mercapto-1-(naphthalene-2-sulfonyl)-pyrrolidine-2-carbonyl]-methyl-amino]-acetylamino]-benzoic acid methyl ester as white solid, (Rf 0.5 EtOAc), MS: 559 (MNH$_4$+).

In a similar manner, the following compounds were prepared from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and 3-(2-Methylamino-acetylamino)-benzoic acid ethyl ester-hydrochloride, followed by disulfide cleavage according to 4.1.: (2R,4R)-3-[2-[[4-Mercapto-1-(naphthalene-2-sulfonyl)-pyrrolidine-2-carbonyl]-methyl-amino]-acetylamino]-benzoic acid ethyl ester as white amorphous, (Rf 0.2 hexane:EtOAc 4:1), MS: 573 (MNH$_4$+);

2-(Methyl-methylaminoacetyl-amino)-benzoic acid methyl ester-hydrochloride, followed by disulfide cleavage according to 4.1.: (2S,4R)-2-[[[[4-Mercapto-1-(naphthalene-2-sulfonyl)-pyrrolidine-2-carbonyl]-methyl-amino]-acetyl]-methyl-amino]-benzoic acid methyl ester as white solid, (Rf 0.3 EtOAc), MS: 556 (MH+);

3-(Methyl-methylaminoacetyl-amino)-benzoic acid ethyl ester-hydrochloride, followed by disulfide cleavage according to 4.1.: (2S,4R)-3-[[[[4-Mercapto-1-(naphthalene-2-sulfonyl)-pyrrolidine-2-carbonyl]-methyl-amino]-acetyl]-methyl-amino]-benzoic acid ethyl ester as white amorphous, (Rf 0.4 EtOAc), MS: 570 (MH+).

N-(4-Methoxymethyl-phenyl)-N-methyl-2-methylamino-acetamide, followed by disulfide cleavage according to 4.2.: (2S,4R)-4-Mercapto-1-(naphthalene-2-sulfonyl)-pyrrolidine-2-carboxylic acid [[(4-methoxymethyl-phenyl)-methyl]-methyl-amide as white solid, (Rf 0.4 CH$_2$Cl$_2$:MeOH:AcOH 9:1:0.1), MS: 542 (MH+).

From (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and N-[4-(tert-Butyl-dimethyl-silanyloxymethyl)-phenyl]-N-methyl-2-methylamino-acetamide according to 1.2 the intermediate (2S,4R)-4-[(3R,5S)-5-[[[[4-(tert-Butyl-dimethyl-silanyloxymethyl)-phenyl]-methyl-carbamoyl]-methyl]-methyl-carbamoyl]-1-(naphthalene-2-sulfonyl)-pyrrolidin-3-yldisulfanyl]-1-(naphthalene-2-sulfonyl)-pyrrolidine-2-carboxylic acid [[[4-(tert-butyl-dimethyl-silanyloxymethyl)-phenyl]-methyl-carbamoyl]-methyl]-methyl-amide as orange solid was prepared, (Rf 0.8 CH$_2$Cl$_2$:MeOH:AcOH 9:1:0.1), MS: 1298 (MNH$_4$+).

Further Modification

Under argon 820 mg (0.57 mmol) (2S,4R)-4-[(3R,5S)-5-[[[[4-(tert-Butyl-dimethyl-silanyloxymethyl)-phenyl]-methyl-carbamoyl]-methyl]-methyl-carbamoyl]-1-(naphthalene-2-sulfonyl)-pyrrolidin-3-yldisulfanyl]-1-(naphthalene-2-sulfonyl)-pyrrolidine-2-carboxylic acid [[[4-(tert-butyl-dimethyl-silanyloxymethyl)-phenyl]-methyl-carbamoyl]-methyl]-methyl-amide were dissolved in 9 ml acetonitrile: CH$_2$Cl$_2$ (2:1) and 502 μl HF (40% in H2O) were added slowly. The solution was stirred for 4.5 h, ice water and CH$_2$Cl$_2$ were added, followed by sat. Na$_2$CO$_3$ solution to adjust pH to 8–9. The layers were separated, the inorganic one was extracted with CH$_2$Cl$_2$ (2×), the combined organic layers were washed with water and dried over MgSO$_4$, filtered and evaporated. Column chromatography on silica gel with a gradient of CH$_2$Cl$_2$/MeOH (100:0-96:4) afforded 590 mg (98%) (2S,4R)-4-[(3R,5S)-5-[[[(4-Hydroxy-methyl-phenyl)-methyl-carbamoyl]-methyl]-methyl-carbamoyl]-1-(naphthalene-2-sulfonyl)-pyrrolidin-3-yldisulfanyl]-1-(naphthalene-2-sulfonyl)-pyrrolidine-2-carboxylic acid [[(4-hydroxymethyl-phenyl)-methyl-carbamoyl]-methyl]-methyl-amide as light yellow solid, (Rf 0.4 CH$_2$Cl$_2$:MeOH 9: 1), MS: 1070 (MNH$_4$+);

Under argon to a suspension of 100 mg (0.09 mmol) (2S,4R)-4-[(3R,5S)-5-[[[(4-Hydroxy-methyl-phenyl)-methyl-carbamoyl]-methyl]-methyl-carbamoyl]-1-(naphthalene-2-sulfonyl)-pyrrolidin-3-yldisulfanyl]-1-(naphthalene-2-sulfonyl)-pyrrolidine-2-carboxylic acid [[(4-hydroxymethyl-phenyl)-methyl-carbamoyl]-methyl]-methyl-amide and 50 μl (0.21 mmol, 2.2 eq) tert-Butyl 2,2,2-trichloroacetimidate were added 1 μl (0.01 mmol) triflic acid at 0° C.. The reaction was allowed to warm to RT and was stirred for 5 h. 27 μL (0.11 mmol, 1.2 eq) ) tert-Butyl 2,2,2-trichloroacetimidate were added, the reaction was stirred for 12 h at RT before further 27 μl (0.11 mmol, 1.2 eq) ) tert-Butyl 2,2,2-trichloroacetimidate, 2 ml cyclohexane and 2 ml of CCl$_4$ were added and stirred for additional 30 h. The solution was added to ice water, sat. aq. NaHCO$_3$ solution was added, the inorganic layer were extracted with CH$_2$Cl$_2$ (3×), the combined organic layers were washed with water and dried over MgSO$_4$, filtered and evaporated. The residue was dissolved in 3 ml CH$_2$Cl$_2$, cooled to 0° C., and filtered and concentrated. Column chromatography on silica gel with EtOAc afforded 48 mg (43%) (2S,4R)-4-[(3R,5S)-5-[[[[(4-tert-Butoxymethyl-phenyl)-methyl-carbamoyl]-methyl]-methyl-carbamoyl]-1-(naphthalene-2-sulfonyl)-pyrrolidin-3-yldisulfanyl]-1-(naphthalene-2-sulfonyl)-pyrrolidine-2-carboxylic acid [[(4-tert-butoxymethyl-phenyl)-methyl-carbamoyl]-methyl]-methyl-amide as off-white amorphous, (Rf 0.2 EtOAc:MeOH 98:2), which was subjected to disulfide cleavage according to 4.2. to give (2S,4R)-4-Mercapto-1-(naphthalene-2-sulfonyl)-pyrrolidine-2-carboxylic acid [[(4-tert-butoxymethyl-phenyl)-methyl-carbamoyl]-methyl]-methyl-amide as white amorphous, (Rf 0.35 CH$_2$Cl$_2$:MeOH 95:5), MS: 584 (MH+).

Disulfide cleavage of the intermediate (2S,4R)-4-[(3R,5S)-5-[[[(4-Hydroxy-methyl-phenyl)-methyl-carbamoyl]-methyl]-methyl-carbamoyl]-1-(naphthalene-2-sulfonyl)- pyrrolidin-3-yldisulfanyl]-1-(naphthalene-2-sulfonyl)-pyrrolidine-2-carboxylic acid [[(4-hydroxymethyl-phenyl)-methyl-carbamoyl]-methyl]-methyl-amide according to 4.2. yielded (2S,4R)-4-Mercapto-1-(naphthalene-2-sulfonyl)-pyrrolidine-2-carboxylic acid [[(4-hydroxymethyl-phenyl)-methyl-carbamoyl]-methyl]-methyl-amide as white solid, (Rf 0.3 $CH_2Cl_2$:MeOH:AcOH 9:1:0.1), MS: 528 (MH$^+$).

Example 19

Further Examples Starting from (2S,4R)-4-[(3R, 5S)-5-Carboxy-1-(naphthalene-2-sulfonyl)-pyrrolidin-3-yldisulfanyl]-1-(naphthalene-2-sulfonyl)-pyrrolidine-2-carboxylic acid The following acids were prepared from (2S,4R)-4-[(3R, 5S)-5-Carboxy-1-(naphthalene-2-sulfonyl)-pyrrolidin-3-yldisulfanyl]-1-(naphthalene-2-sulfonyl)-pyrrolidine-2-carboxylic acid and 2-(2-Methylamino-acetylamino)-benzoic acid methyl ester-hydrochloride according to 1.2., followed by 5.1. and 4.2.: (2S,4R)-2-[2-[[4-Mercapto-1-(naphthalene-2-sulfonyl)-pyrrolidine-2-carbonyl]-methyl-amino]-acetylamino]-benzoic acid as white solid, (Rf 0.4 $CH_2Cl_2$:MeOH:AcOH 9:1:0.1), MS: 526 (M-H)$^-$;

3-(2-Methylamino-acetylamino)-benzoic acid ethyl ester·hydrochloride according to 1.2., followed by 5.1. and 4.2.: (2S,4R)-3-[2-[[4-Mercapto-1-(naphthalene-2-sulfonyl)-pyrrolidine-2-carbonyl]-methyl-amino]-acetylamino]-benzoic acid as light yellow solid, (Rf 0.5 $CH_2Cl_2$:MeOH 4:1), MS: 545 (MNH$_4$+);

2-(Methyl-methylaminoacetyl-amino)-benzoic acid methyl ester-hydrochloride according to 1.2., followed by 5.1. and 4.2.: (2S,4R)-2-[[[[4-Mercapto-1-(naphthalene-2-sulfonyl)-pyrrolidine-2-carbonyl]-methyl-amino]-acetyl]-methyl-amino]-benzoic acid as light blue solid, (Rf 0.2 $CH_2Cl_2$:MeOH:AcOH 95:5:0.1), MS: 540 (M-H)$^-$;

3-(Methyl-methylaminoacetyl-amino)-benzoic acid ethyl ester-hydrochloride according to 1.2., followed by 5.1. and 4.2.: (2S,4R)-3-[[[[4-Mercapto-1-(naphthalene-2-sulfonyl)-pyrrolidine-2-carbonyl]-methyl-amino]-acetyl]-methyl-amino]-benzoic acid as white solid, (Rf 0.2 $CH_2Cl_2$:MeOH:AcOH 95:5:0.1), 540 (M-H)$^-$.

The following compounds were prepared from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and (S)-3-Amino-N-benzyl-N-methyl-succinamic acid tert-butyl ester.HCl, (S)-3-Amino-N-(4-isopropyl-phenyl)-succinamic acid tert-butyl ester, (S)-N-(4-Isopropyl-phenyl)-3-methylamino-succinamic acid tert-butyl ester, (S)-N-Benzyl-N-methyl-3-methylamino-succinamic acid tert-butyl ester, (S)-N-Benzyl-N-methyl-2-methylamino-propionamide, N-Benzyl-N-methyl-2-methylamino-acetamide, (S)-pyrrolidine-2-carboxylic acid methyl ester, 3-Cyclopropylamino-propionic acid ethyl ester, (R)-pyrrolidine-2-carboxylic acid benzyl ester, 1-Methylaminoacetyl-piperidine-4-carboxylic acid ethyl ester, 3-Methylamino-propionic acid ethyl ester, 3-Amino-propionic acid methyl ester, (S)-N-Benzyl-N-methyl-3-methylamino-succinamic acid tert-butyl ester·hydrochloride and 2-Aminopyridine according to 1.3., followed by disulfide cleavage according to 4.2.:

(S)-N-Benzyl-3-[[(2S,4R)-4-mercapto-1-(naphthalene-2-sulfonyl)-pyrrolidine-2-carbonyl]-amino]-N-methyl-succinamic acid tert-butyl ester as white solid, MS: 612 (MH$^+$);

(S)-N-(4-Isopropyl-phenyl)-3-[[(2S,4R)-4-mercapto-1-(naphthalene-2-sulfonyl)-pyrrolidine-2-carbonyl]-amino]-succinamic acid tert-butyl ester as light yellow solid, MS: 626 (MH$^+$);

(S)-N-(4-Isopropyl-phenyl)-3-[[(2S,4R)-4-mercapto-1-(naphthalene-2-sulfonyl)-pyrrolidine-2-carbonyl]-methyl-amino]-succinamic acid tert-butyl ester as white solid, MS: 638 (M-H)$^-$; (S)-N-Benzyl-3-[[(2S,4R)-4-mercapto-1-(naphthalene-2-sulfonyl)-pyrrolidine-2-carbonyl]-methyl-amino]-N-methyl-succinamic acid tert-butyl ester as white solid, MS: 626 (MH$^+$);

(2S,4R)-4-Mercapto-1-(naphthalene-2-sulfonyl)-pyrrolidine-2-carboxylic acid (S)-[1-(benzyl-methyl-carbamoyl)-ethyl]-methyl-amide as white solid, MS: 526 (MH$^+$);

(2S,4R)-4-Mercapto-1-(naphthalene-2-sulfonyl)-pyrrolidine-2-carboxylic acid [(benzyl-methyl-carbamoyl)-methyl]-methyl-amide as white solid, MS: 512 (MH$^+$);

(2S)-1-[(2S,4R)-4-Mercapto-1-(naphthalene-2-sulfonyl)-pyrrolidine-2-carbonyl]-pyrrolidine-2-carboxylic acid methyl ester as colorless oil, mp 80–82° C., MS: 449 (MH$^+$);

(2S,4R)-3-[Cyclopropyl-[4-mercapto-1-(naphthalene-2-sulfonyl)-pyrrolidine-2-carbonyl]-amino]-propionic acid ethyl ester as colorless oil, MS: 476 (M);

(R)-1-[(2S,4R)-4-Mercapto-1-(naphthalene-2-sulfonyl)-pyrrolidine-2-carbonyl]-pyrrolidine-2-carboxylic acid benzyl ester as white foam, MS: 525 (MH$^+$);

(2S,4R)-1-[[[4-Mercapto-1-(naphthalene-2-sulfonyl)-pyrrolidine-2-carbonyl]-methyl-amino]-acetyl]-piperidine-4-carboxylic acid ethyl ester as white solid, mp 65–66.5° C., MS: 548 (MH$^+$);

(2S,4R)-3-[[4-Mercapto-1-(naphthalene-2-sulfonyl)-pyrrolidine-2-carbonyl]-methyl-amino]-propionic acid ethyl ester as colorless oil, MS: 451 (MH$^+$);

(2S,4R)-3-[[4-Mercapto-1-(naphthalene-2-sulfonyl)-pyrrolidine-2-carbonyl]-amino]-propionic acid methyl ester as colorless oil, MS: 421 (M-H)$^-$;

(S)-N-Benzyl-3-[[(2S,4R)-4-mercapto-1-(naphthalene-2-sulfonyl)-pyrrolidine-2-carbonyl]-methyl-amino]-N-methyl-succinamic acid tert-butyl ester as white solid, MS: 626 (MH$^+$);

(2S,4R)-4-Mercapto-1-(naphthalene-2-sulfonyl)-pyrrolidine-2-carboxylic acid (pyridin-2-ylmethyl)-amide as white crystalline, MS: 428 (MH$^+$);

The following compounds were prepared from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and (S)-3-Amino-N-(4-isopropyl-phenyl)-succinamic acid tert-butyl ester, (S)-3-Amino-N-benzyl-N-methyl-succinamic acid tert-butyl ester.HCl, (S)-N-Benzyl-N-methyl-3-methylamino-succinamic acid tert-butyl ester according to 1.3., followed by t-butyl ester cleavage according to 5.3. and disulfide cleavage according to to 4.2.:

(S)-N-(4-Isopropyl-phenyl)-3-[[(2S,4R)-4-mercapto-1-(naphthalene-2-sulfonyl)-pyrrolidine-2-carbonyl]-amino]-succinamic acid as white solid, MS: 570 (MH$^+$);

(S)-N-Benzyl-3-[[(2S,4R)-4-mercapto-1-(naphthalene-2-sulfonyl)-pyrrolidine-2-carbonyl]-amino]-N-methyl-succinamic acid as white solid, MS: 554 (M-H)$^-$;

(3S)-N-Benzyl-3-[[(2S,4R] )-4-mercapto-1-(naphthalene-2-sulfonyl)-pyrrolidine-2-carbonyl]-methyl-amino]-N-methyl-succinamic acid as white solid, MS: 570 (MH$^+$);

The following compounds were prepared from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and 1-Methylaminoacetylpiperidine-4-carboxylic acid ethyl ester, (R)-pyrrolidine-2-carboxylic acid benzyl ester, 3-Methylamino-propionic acid ethyl ester, 3Cyclopropylamino-propionic acid ethyl ester and 3-Amino-propionic acid methyl ester according to 1.3., respectively, followed by disulfide cleavage according to 4.3.:

(2S,4R)-1-[[[4-Mercapto-1-(naphthalene-2-sulfonyl)-pyrrolidine-2-carbonyl]-methyl-amino]-acetyl]-piperidine-4-carboxylic acid as white solid, mp 105–107° C., MS: 520 (MH$^+$);

(2R)-1-[(2S,4R)-4-Mercapto-1-(naphthalene-2-sulfonyl)-pyrrolidine-2-carbonyl]-pyrrolidine-2-carboxylic acid as white solid, mp 240–241.5° C., MS: 435 (MH$^+$);

(2S,4R)-3-[[4-Mercapto-1-(naphthalene-2-sulfonyl)-pyrrolidine-2-carbonyl]-methyl-amino]-propionic acid as white solid, mp 160–162° C. 421 (M-H)$^-$;

(2S,4R)-3-[Cyclopropyl-[4-mercapto-1-(naphthalene-2-sulfonyl)-pyrrolidine-2-carbonyl]-amino]-propionic acid as white solid, MS: 447 (M-H)$^-$;

(2S,4R)-3-[[4-Mercapto-1-(naphthalene-2-sulfonyl)-pyrrolidine-2-carbonyl]-amino]-propionic acid as white solid, mp 88–89° C., MS: 407 (M-H)$^-$.

Example 20

Further Examples from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid To 300 mg (0.44 mmol) (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid in 25 ml CH$_2$Cl$_2$ were added 100 µl (0.89 mmol, 1 eq) 4-methyl morpholine, followed by 331 mg (1.1 mmol, 1.25 eq) TPTU and 115 µl (0.89 mmol, 1 eq) N-methylbenzyl amine. The solution was stirred at RT over night. The mixture was added to a 1M KHSO$_4$ solution, extracted with EtOAc and the organic phase was washed with 5% aq. NaHCO$_3$ solution and brine. The solution was dried over Na$_2$SO$_4$, filtered and evaporated, yielding 313 mg (81%) (2S,4R)-4-[(3R,5S)-5-(Benzyl-methyl-carbamoyl)-1-(naphthalene-2-sulfonyl)-pyrrolidin-3-yldisulfanyl]-1-(naphthalene-2-sulfonyl)-pyrrolidine-2-carboxylic acid benzyl-methyl-amide as colorless foam, which was subjected to disulfide cleavage according to general procedure 4.1. to give (2S,4R)-4-Mercapto-1-(naphthalene-2-sulfonyl)-pyrrolidine-2-carboxylic acid benzyl-methyl-amide as white solid, MS: 441 (MH$^+$).

Analogously the following compounds were prepared from (2S,4R)-4-[(3R,5S)-5-Carboxy-1-(naphthalene-2-sulfonyl)-pyrrolidin-3-yldisulfanyl]-1-(naphthalene-2-sulfonyl)-pyrrolidine-2-carboxylic acid and ethyl isonipecotate, ethyl 4-aminobenzoate, L-tryptophan methyl ester·hydrochloride, and 4-(3-Amino-propionylamino)-benzoic acid ethyl ester, respectively:

(2S,4R)-1-[4-Mercapto-1-(naphthalene-2-sulfonyl)-pyrrolidine-2-carbonyl]-piperidine-4-carboxylic acid ethyl ester as white solid, MS: 477 (MH$^+$);

(2S,4R)-4-[[4-Mercapto-1-(naphthalene-2-sulfonyl)-pyrrolidine-2-carbonyl]-amino]-benzoic acid ethyl ester as white solid, MS: 485 (MH$^+$);

(S)-3-(1H-Indol-3-yl)-2-[[(2S,4R)-4-mercapto-1-(naphthalene-2-sulfonyl)-pyrrolidine-2-carbonyl]-amino]-propionic acid methyl ester as white solid, MS: 538 (MH$^+$);

(2S,4R)-4-[3-[[4-Mercapto-1-(naphthalene-2-sulfonyl)-pyrrolidine-2-carbonyl]-amino]-propionylamino]-benzoic acid ethyl ester as white solid, MS: 556 (MH$^+$).

Ester cleavage for (2S,4R)-1-[4-Mercapto-1-(naphthalene-2-sulfonyl)-pyrrolidine-2-carbonyl]-piperidine-4-carboxylic acid ethyl ester and (S)-3-(1H-Indol-3-yl)-2-[[(2S,4R)-4-mercapto-1-(naphthalene-2-sulfonyl)-pyrrolidine-2-carbonyl]-amino]-propionic acid methyl ester according to general procedure 5.2. respectively gave:

(2S,4R)-1-[4-Mercapto-1-(naphthalene-2-sulfonyl)-pyrrolidine-2-carbonyl]-piperidine-4-carboxylic acid as white solid, MS: 449 (MH$^+$);

(S)-3-(1H-Indol-3-yl)-2-[[(2S,4R)-4-mercapto-1-(naphthalene-2-sulfonyl)-pyrrolidine-2-carbonyl]-amino]-propionic acid as white solid, MS: 522 (M-H)$^-$.

Example 21

Other disulfid-diacids modifications

Treatment of (2S,4R)-4-[(3R,5S)-5-carboxy-1-(4-tert-butyl-benzenesulfonyl)-pyrrolidin-3-yldisulfanyl]-1-(4-tert-butyl-benzenesulfonyl)-pyrrolidine-2-carboxylic acid with N-methyl benzylamine and ethyl-piperidine-4-carboxylate (1.2.),respectively, followed by disulfide cleavage according to general procedure 4.1. gave:

(2S,4R)-1-(4-tert-Butyl-benzenesulfonyl)-4-mercapto-pyrrolidine-2-carboxylic acid benzyl-methyl-amide as colorless oil, MS: 447 (MH$^+$);

(2S,4R)-1-[1-(4-tert-Butyl-benzenesulfonyl)-4-mercapto-pyrrolidine-2-carbonyl]-piperidine-4-carboxylic acid ethyl ester as colorless oil, MS: 483 (MH$^+$);

Treatment of (2S,4R)-4-[(3R,5S)-5-carboxy-1-(naphthalene-2-carbonyl)-pyrrolidin-3-yldisulfanyl]-1-(naphthalene-2-carbonyl)-pyrrolidine-2-carboxylic acid with N-methyl benzylamine and ethyl-piperidine-4-carboxylate (1.2.) respectively, followed by disulfide cleavage according to general procedure 4.1. gave: (2S,4R)-4-Mercapto-1-(naphthalene-2-carbonyl)-pyrrolidine-2-carboxylic acid benzyl-methyl-amide as colorless oil, MS: 405 (MH$^+$);

(2S,4R)-1-[4-Mercapto-1-(naphthalene-2-carbonyl)-pyrrolidine-2-carbonyl]-piperidine-4-carboxylic acid ethyl ester as colorless oil, MS: 441 (MH$^+$).

Example 22

Starting from AcS-acids 22.1. (2S,4R)-4-Acetylsulfanyl-1-(naphthalene-2-sulfonyl)-pyrrolidine-2-carboxylic acid as educt (a1) 150 mg (0.4 mmol) (2S,4R)-4-Acetylsulfanyl-1-(naphthalene-2-sulfonyl)-pyrrolidine-2-carboxylic acid in 10 ml CH$_2$Cl$_2$ were treated with 49 µl (0.43 mmol, 1.1 eq) 4-methyl morpholine, 142 mg (0.47 mmol, 1.2 eq) TPTU and 140 mg (0.59 mmol, 1.5 eq) 4-(methyl-methylaminoacetyl-amino)-benzoic acid methyl ester. The solution was stirred at RT over night. The mixture was concentrated and purified by flash chromatography yielding 233 mg (98%) (2S,4R)-4-[[[[4-Acetylsulfanyl-1-(naphthalene-2-sulfonyl)-pyrrolidine-2-carbonyl]-amino]-acetyl]-methyl-amino]-benzoic acid methyl ester as white foam, MS: 598 (MH$^+$).

(a2) According to general procedure 7.2. (2S,4R)-4-[[[4-Acetylsulfanyl-1-(naphthalene-2-sulfonyl)-pyrrolidine-2-carbonyl]-amino]-acetyl]-methyl-amino]-benzoic acid methyl ester was transferred to (2S,4R)-4-[[[[4-Mercapto-1-(naphthalene-2-sulfonyl)-pyrrolidine-2-carbonyl]-methyl-amino]-acetyl]-methyl-amino]-benzoic acid as white solid, MS: 542 (MH$^+$).

(a3) 80 mg (0.134 mmol) (2S,4R)-4-[[[[4-Acetylsulfanyl-1-(naphthalene-2-sulfonyl)-pyrrolidine-2-carbonyl]-amino]-acetyl]-methyl-amino]-benzoic acid methyl ester in 5 ml methanol were treated with 335 µl 0.6M (0.2 mmol) sodium methanolate in methanol at 0° C. for 1 h. The solution was poured on EtOAc/1M KHSO$_4$ and the inorganic phase was extracted with EtOAc, the organic phases were washed with brine, dried over Na$_2$SO$_4$ and were evaporated. Column chromatography with EtOAc yielded 70 mg (quant) (2S,4R)-4-[[[[4-Mercapto-1-(naphthalene-2-sulfonyl)-pyrrolidine-2-carbonyl]-methyl-amino]-acetyl]-methyl-amino]-benzoic acid methyl ester as white foam, MS: 556 (MH$^+$).

Analogously the following compounds were prepared from (2S,4R)-4-Acetylsulfanyl-1-(naphthalene-2-sulfonyl)-pyrrolidine-2-carboxylic acid and methyl-4-methylaminobenzoate, 4-(2-Amino-acetylamino)-benzoic acid ethyl ester, 4-(Aminoacetyl-methyl-amino)-benzoic acid methyl ester, 4-(2-Methylamino-acetylamino)-benzoic acid ethyl ester, ethyl-4aminobenzoate, 2,3,6-trifluorobenzylamine, respectively:

(b1) (2S,4R)-4-[[4-Acetylsulfanyl-1-(naphthalene-2-sulfonyl)-pyrrolidine-2-carbonyl]-methyl-amino]-benzoic acid methyl ester as white solid, MS: 527 (MH$^+$);

(b2) (2S,4R)-4-[[4-Mercapto-1-(naphthalene-2-sulfonyl)-pyrrolidine-2-carbonyl]-methyl-amino]-benzoic acid as white solid, MS: 471 (MH$^+$);

(b3) (2S,4R)-4-[[4-Mercapto-1-(naphthalene-2-sulfonyl)-pyrrolidine-2-carbonyl]-methyl-amino]-benzoic acid methyl ester as white solid, MS: 485 (MH$^+$);

(c1) (2S,4R)-4-[2-[[4-Acetylsulfanyl-1-(naphthalene-2-sulfonyl)-pyrrolidine-2-carbonyl]-amino]-acetylamino]-benzoic acid ethyl ester as white foam, MS: 584 (MH$^+$);

(c2) (2S,4R)-4-[2-[[4-Mercapto-1-(naphthalene-2-sulfonyl)-pyrrolidine-2-carbonyl]-amino]-acetylamino]-benzoic acid as white crystalline, MS: 514 (MH$^+$);

(c3) (2S,4R)-4-[2-[[4-Mercapto-1-(naphthalene-2-sulfonyl)-pyrrolidine-2-carbonyl]-amino]-acetylamino]-benzoic acid ethyl ester as white crystalline, MS: 542 (MH$^+$);

(d1) (2S,4R)-4-[[[[4-Acetylsulfanyl-1-(naphthalene-2-sulfonyl)-pyrrolidine-2-carbonyl]-amino]-acetyl]-methyl-amino]-benzoic acid methyl ester as white foam, MS: 584 (MH$^+$);

(d2) (2S,4R)-4-[[[[4-Mercapto-1-(naphthalene-2-sulfonyl)-pyrrolidine-2-carbonyl]-amino]-acetyl]-methyl-amino]-benzoic acid as white foam, MS: 526 (M-H)$^-$;

(d3) (2S,4R)-4-[[[[4-Mercapto-1-(naphthalene-2-sulfonyl)-pyrrolidine-2-carbonyl]-amino]-acetyl]-methyl-amino]-benzoic acid methyl ester as white crystalline, MS: 542 (MH$^+$);

(e1) (2S,4R)-4-[2-[[4-Acetylsulfanyl-1-(naphthalene-2-sulfonyl)-pyrrolidine-2-carbonyl]-amino]-acetylamino]-benzoic acid ethyl ester as white solid, MS: 598 (MH$^+$);

(e2) (2S,4R)-4-[2-[[4-Mercapto-1-(naphthalene-2-sulfonyl)-pyrrolidine-2-carbonyl]-methyl-amino]-acetylamino]-benzoic acid as white foam, MS: 528 (MH$^+$);

(e3) (2S,4R)-4-[2-[[4-Mercapto-1-(naphthalene-2-sulfonyl)-pyrrolidine-2-carbonyl]-methyl-amino]-acetylamino]-benzoic acid ethyl ester as white solid, MS: 556 (MH$^+$).

(f2) (2S,4R)-4-[[4-Mercapto-1-(naphthalene-2-sulfonyl)-pyrrolidine-2-carbonyl]-amino]-benzoic acid as white solid, MS: 457 (MH$^+$).

(f3) (2S,4R)-4-[[4-Mercapto-1-(naphthalene-2-sulfonyl)-pyrrolidine-2-carbonyl]-amino]-benzoic acid ethyl ester as white solid, MS: 485 (MH$^+$).

(g1) Thioacetic acid (3R,5S)-S-[1-(naphthalene-2-sulfonyl)-5-(2,3,6-trifluoro-benzylcarbamoyl)-pyrrolidin-3-yl] ester, MS: 523 (MH$^+$);

(g3) (2S,4R)-4-Mercapto-1-(naphthalene-2-sulfonyl)-pyrrolidine-2-carboxylic acid 2,3,6-trifluoro-benzylamide as colorless oil, MS: 481 (MH$^+$).

Further Examples:

(2S,4R)-4-Acetylsulfanyl-1-(naphthalene-2-sulfonyl)-pyrrolidine-2-carboxylic acid with 3-Amino-N-ethylpiperidine according to 1.2. followed by deprotection according to 7.1. gave 1:1 Mixture of (2S,4R)-4-mercapto-1-(naphthalene-2-sulfonyl)-pyrrolidine-2-carboxylic acid (R)- and (S)-(1-ethyl-piperidin-3-yl)-amide as white solid, MS: 448 (MH$^+$).

To 200 mg (0.52 mmol) (2S,4R)-4-Acetylsulfanyl-1-(naphthalene-2-sulfonyl)-pyrrolidine-2-carboxylic acid in 10 ml toluene and 4 ml THF were added 226 µl (2.6 mmol, 5eq) oxalyl chloride and the solution was stirred at RT for 2 h, and was concentrated. The residue was dissolved in 8 ml THF, and the solution was added at 0° C. to a suspension of 180 mg (1.19 mmol, 2.2 eq) 4-methylamino benzoic acid and 360 mg (2.6 mmol, 5eq) K$_2$CO$_3$ in 8 ml THF. After 2.5 h the solution was acidified by 1M KHSO$_4$ and extracted with EtOAc, the organic phase was washed with brine and dried over Na$_2$SO$_4$. Column chromatography yielded 91 mg (35%) (2S,4R)-4-[[4-Acetylsulfanyl-1-(naphthalene-2-sulfonyl)-pyrrolidine-2-carbonyl]-methyl-amino]-benzoic acid as white solid, MS: 513 (MH$^+$).

22.2 Starting from from (2S,4R)-4-Acetylsulfanyl-pyrrolidine-1,2-dicarboxylic acid 1-benzyl ester Analogously the following compounds were prepared according to 1.2. from (2S,4R)-4-Acetylsulfanyl-pyrrolidine-1,2-dicarboxylic acid 1-benzyl ester and ethyl-4-aminobenzoate, L-leucine ethylester.HCl, L-tryptophan methylester.HCl, L-valine methylester-HCl, L-tyrosine methylester-HCl, ethyl isonipecotate, respectively, followed by thioester cleavage according to 7.2.:

(2S,4R)-2-(4-Carboxy-phenylcarbamoyl)-4-mercapto-pyrrolidine-1-carboxylic acid benzyl ester as white solid, MS: 399 (M-H)$^-$;

(2S,4R)-2-[(S)-1-Carboxy-3-methyl-butylcarbamoyl]-4-mercapto-pyrrolidine-1-carboxylic acid benzyl ester as colorless amorphous, MS: 395 (MH$^+$);

(2S,4R)-2-[(S)-11-Carboxy-2-(1H-indol-2-yl)-ethylcarbamoyl]-4-mercapto-pyrrolidine-1-carboxylic acid benzyl ester as white solid, MS: 468 (MH$^+$);

(2S,4R)-2-[(S)-1-Carboxy-2-methyl-propylcarbamoyl]-4-mercapto-pyrrolidine-1-carboxylic acid benzyl ester as white solid, MS: 381 (MH$^+$);

(2S,4R)-2-[(S)-1-Carboxy-2-(4-hydroxy-phenyl)-ethylcarbamoyl]-4-mercapto-pyrrolidine-1-carboxylic acid benzyl ester as white solid, MS: 445 (MH$^+$);

(2S,4R)-1-(1-Benzyloxycarbonyl-4-mercapto-pyrrolidine-2-carbonyl)-piperidine-4-carboxylic acid as colorless amorphous, MS: 359(M-SH);

Analogously the following compounds were prepared according to 1.2. from (2S,4R)-4-Acetylsulfanyl-pyrrolidine-1,2-dicarboxylic acid 1-benzyl ester and piperidine, 4-amino-1-benzylpiperidine, 2-amino-1,3-propandiol, N-benzylmethylamine, 3-aminopropionitrile, respectively, followed by thioester cleavage according to 7.1.:

(2S,4R)-4-Mercapto-2-(piperidine-1-carbonyl)-pyrrolidine-1-carboxylic acid benzyl ester as colorless amorphous, MS: 349 (MH$^+$);

(2S,4R)-2-(1-Benzyl-piperidin-4-ylcarbamoyl)-4-mercapto-pyrrolidine-1-carboxylic acid benzyl ester as colorless amorphous, MS: 454 (MH$^+$);

(2S,4R)-2-(2-Hydroxy-1-hydroxymethyl-ethylcarbamoyl)-4-mercapto-pyrrolidine-1-carboxylic acid benzyl ester as colorless amorphous, MS: 355 (MH$^+$);

(2S,4R)-2-(Benzyl-methyl-carbamoyl)-4-mercapto-pyrrolidine-1-carboxylic acid benzyl ester as colorless amorphous, MS: 351 (M-SH);

(2S,4R)-2-(2-Cyano-ethylcarbamoyl)-4-mercapto-pyrrolidine-1-carboxylic acid benzyl ester as colorless amorphous, MS: 334 (MH$^+$);

Analogously the following compounds were prepared according to 1.2. from (2S,4R)-4-Acetylsulfanyl-pyrrolidine-1,2-dicarboxylic acid 1-benzyl ester
and ethyl-4-aminobenzoate, L-tryptophan methylester.HCl, L-valine methylester.HCl, L-leucin ethylester-HCl, L-tyrosine methylester-HCl, ethyl isonipecotate, respectively, followed by thioester cleavage according to 7.3.:

(2S,4R)-2-(4-Ethoxycarbonyl-phenylcarbamoyl)-4-mercapto-pyrrolidine-1-carboxylic acid benzyl ester as white solid, MS: 429 (MH$^+$);

(2S,4R)-2-[(S)-2-(1H-Indol-2-yl)-1-methoxycarbonyl-ethylcarbamoyl]-4-mercapto-pyrrolidine-1-carboxylic acid benzyl ester as white solid, MS: 482 (MH$^+$);

(2S,4R)-4-Mercapto-2-[(S)-1-methoxycarbonyl-2-methyl-propylcarbamoyl]-pyrrolidine-1-carboxylic acid benzyl ester as colorless amorphous, MS: 395 (MH$^+$);

(2S,4R)-2-[(S)-1-Ethoxycarbonyl-3-methyl-butylcarbamoyl]-4-mercapto-pyrrolidine-1-carboxylic acid benzyl ester as colorless amorphous, MS: 423 (MH$^+$);

(2S,4R)-2-[(S)-2-(4-Hydroxy-phenyl)-1-methoxycarbonyl-ethylcarbamoyl]-4-mercapto-pyrrolidine-1-carboxylic acid benzyl ester as white solid, MS: 459 (MH$^+$);

(2S,4R)-1-(1-Benzyloxycarbonyl-4-mercapto-pyrrolidine-2-carbonyl)-piperidine-4-carboxylic acid ethyl ester as colorless amorphous, MS: 387(M-SH).

(2S,4R)-4-Acetylsulfanyl-2-[[[(4-methoxycarbonyl-phenyl)-methyl-carbamoyl]-methyl]-methyl-carbamoyl]-pyrrolidine-1-carboxylic acid tert-butyl ester- modification of the residue at the pyrrolidine-N From (2S,4R)-4-Acetylsulfanyl-pyrrolidine-1,2-dicarboxylic acid 1-tert-butyl ester and 4-(methyl-methylaminoacetyl-amino)-benzoic acid methyl ester was prepared according to general procedure 1.2. (2S,4R)-4-Acetylsulfanyl-2-[[[(4-methoxycarbonyl-phenyl)-methyl-carbamoyl]-methyl]-methyl-carbamoyl]-pyrrolidine-1-carboxylic acid tert-butyl ester as white solid.

2.92 g (5.7 mmol) (2S,4R)-4-Acetylsulfanyl-2-[[[(4-methoxycarbonyl-phenyl)-methyl-carbamoyl]-methyl]-methyl-carbamoyl]-pyrrolidine-1-carboxylic acid tert-butyl ester in 60 ml CH$_2$Cl$_2$ were treated with 15 ml TFA at 0° C. until no starting material could be detected. The solution was concentrated, dissolved in toluene and evaporated 3 times yielding 2.7 g (93%) (2S,4R)-4-[[[(4-Acetylsulfanyl-pyrrolidine-2-carbonyl]-methyl-amino]-acetyl]-methyl-amino]-benzoic acid methyl ester.trifluoro-acetate salt as brown foam, MS 408 (MH$^+$).

To 179 mg (0.71 mmol, 1.5 eq) Biphenyl sulfonyl chloride in 3 ml CH$_2$Cl$_2$ were added 248 mg (0.47 mmol) (2S,4R)-4-[[[(4-Acetylsulfanyl-pyrrolidine-2-carbonyl)-methyl-amino]-acetyl]-methyl-amino]-benzoic acid methyl ester trifluoro-acetate salt in 1 ml CH$_2$Cl$_2$, followed by 83 μl (0.75 mmol,1.6 eq) NMM and 58 mg (0.047 mmol, 0.1 eq) DMAP. The reaction was shaken for 30 min until no starting material could be detected. The organic phase was extracted with 1M KHSO$_4$, brine and dried over Na$_2$SO$_4$. Column chromatography with EtOAc yielded 134 mg (46%) (2S,4R)-4-[[[[4-Acetylsulfanyl-1-(biphenyl-4-sulfonyl)-pyrrolidine-2-carbonyl]-methyl-amino]-acetyl]-methyl-amino]-benzoic acid methyl ester as white foam, MS: 624 (MH$^+$);

Analogously the following compounds were prepared replacing biphenylsulfonyl chloride against trans-beta-styrenesulfonyl chloride, 2-(1-naphthyl)ethane sulfonyl chloride, 8-quinoline sulfonylchoride, 1-naphthyl sulfonyl chloride, 2-trifluoromethylsulfonyl chloride, alpha-toluenesulfonyl chloride, 4-nitrobenzene sulfonylchloride, 4-fluorobenzenesulfonyl chloride, 2-thiophenesulfonyl chloride, benzenesulfonyl chloride:

(E)-(2S,4R)-4-[[[[4-Acetylsulfanyl-1-(2-phenyl-ethenesulfonyl)-pyrrolidine-2-carbonyl]-methyl-amino]-acetyl]-methyl-amino]-benzoic acid methyl ester as beige foam, MS: 574 (MH$^+$);

(2S,4R)-4-[[[[4-Acetylsulfanyl-1-(2-naphthalen-1-yl-ethanesulfonyl)-pyrrolidine-2-carbonyl]-methyl-amino]-acetyl]-methyl-amino]-benzoic acid methyl ester as white foam, MS: 626 (MH$^+$);

(2S,4R)-4-[[[[4-Acetylsulfanyl-1-(quinoline-8-sulfonyl)-pyrrolidine-2-carbonyl]-methyl-amino]-acetyl]-methyl-amino]-benzoic acid methyl ester as white foam, MS: 599 (MH$^+$);

(2S,4R)-4-[[[[4-Acetylsulfanyl-1-(naphthalene-1-sulfonyl)-pyrrolidine-2-carbonyl]-methyl-amino]-acetyl]-methyl-amino]-benzoic acid methyl ester as white foam, MS: 598 (MH$^+$);

(2S,4R)-4-[[[[4-Acetylsulfanyl-1-(2-trifluoromethyl-benzenesulfonyl)-pyrrolidine-2-carbonyl]-methyl-amino]-acetyl]-methyl-amino]-benzoic acid methyl ester as white foam, MS: 616 (MH$^+$);

(2S,4R)-4-[[(4-Acetylsulfanyl-1-phenylmethanesulfonyl-pyrrolidine-2-carbonyl)-methyl-amino]-acetyl]-methyl-amino]-benzoic acid methyl ester as white foam, MS: 562 (MH$^+$);

(2S,4R)-4-[[[[4-Acetylsulfanyl-1-(4-fluoro-benzenesulfonyl)-pyrrolidine-2-carbonyl]-methyl-amino]-acetyl]-methyl-amino]-benzoic acid methyl ester as white foam, MS: 566 (MH$^+$);

(2S,4R)-4-[[[[4-Acetylsulfanyl-1-(thiophene-2-sulfonyl)-pyrrolidine-2-carbonyl]-methyl-amino]-acetyl]-methyl-amino]-benzoic acid methyl ester as white foam, MS: 554 (MH$^+$);

(2S,4R)-4-[[[(4-Acetylsulfanyl-1-benzenesulfonyl-pyrrolidine-2-carbonyl)-methyl-amino]-acetyl]-methyl-amino]-benzoic acid methyl ester as white foam, MS: 548 (MH$^+$);

(2S,4R)-4-[[[[4-Acetylsulfanyl-1-(4-nitro-benzenesulfonyl)-pyrrolidine-2-carbonyl]-methyl-amino]-acetyl]-methyl-amino]-benzoic acid methyl ester as beige foam, MS: 593 (MH$^+$);

To 106 mg (0.17 mmol) (2S,4R)-4-[[[[4-Acetylsulfanyl-1-(biphenyl-4-sulfonyl)-pyrrolidine-2-carbonyl]-methyl-amino]-acetyl]-methyl-amino]-benzoic acid methyl ester in 10 ml THF were added 10 ml 0.1 M LiOH at 0° C. and the solution was stirred at RT for 2 h, poured on 2 ml 1M KHSO$_4$ and extracted with EtOAc. The combined organic layers were washed with brine and were dried with Na$_2$SO$_4$. The residue was titrurated with hexane to give 67 mg (69%) (2S,4R)-4-[[[[1-(Biphenyl-4-sulfonyl)-4-mercapto-pyrrolidine-2-carbonyl]-methyl-amino]-acetyl]-methyl-amino]-benzoic acid as white solid, MS: 568 (MH$^+$).

Analogously the following compounds were prepared:
From (2S,4R)-4-[[[[4-Acetylsulfanyl-1-(2-naphthalen-1-yl-ethanesulfonyl)-pyrrolidine-2-carbonyl]-methyl-amino]-acetyl]-methyl-amino]-benzoic acid methyl ester: (2S,4R)-4-[[[[4-Mercapto-1-(2-naphthalen-1-yl-ethanesulfonyl)-pyrrolidine-2-carbonyl]-methyl-amino]-acetyl]-methyl-amino]-benzoic acid as white solid, MS: 570 (MH⁺);
From (2S,4R)-4-[[[[4-Acetylsulfanyl-1-(quinoline-8-sulfonyl)-pyrrolidine-2-carbonyl]-methyl-amino]-acetyl]-methyl-amino]-benzoic acid methyl ester: (2S,4R)-4-[[[[4-Mercapto-1-(quinoline-8-sulfonyl)-pyrrolidine-2-carbonyl]-methyl-amino]-acetyl]-methyl-amino]-benzoic acid as white solid, MS: 543 (MH⁺);
From (2S,4R)-4-[[[[4-Acetylsulfanyl-1-(naphthalene-1-sulfonyl)-pyrrolidine-2-carbonyl]-methyl-amino]-acetyl]-methyl-amino]-benzoic acid methyl ester: (2S,4R)-4-[[[[4-Mercapto-1-(naphthalene-1-sulfonyl)-pyrrolidine-2-carbonyl]-methyl-amino]-acetyl]-methyl-amino]-benzoic acid as white solid, MS: 542 (MH⁺);
From (2S,4R)-4-[[[[4-Acetylsulfanyl-1-(2-trifluoromethyl-benzenesulfonyl)-pyrrolidine-2-carbonyl]-methyl-amino]-acetyl]-methyl-amino]-benzoic acid methyl ester: (2S,4R)-4-[[[[4-Mercapto-1-(2-trifluoromethyl-benzenesulfonyl)-pyrrolidine-2-carbonyl]-methyl-amino]-acetyl]-methyl-amino]-benzoic acid as white solid, MS: 560 (MH⁺);
From (2S,4R)-4-[[[(4-Acetylsulfanyl-1-phenylmethanesulfonyl-pyrrolidine-2-carbonyl)-methyl-amino]-acetyl]-methyl-amino]-benzoic acid methyl ester: (2S,4R)-4-[[[(4-Mercapto-1-phenylmethanesulfonyl-pyrrolidine-2-carbonyl)-methyl-amino]-acetyl]-methyl-amino]-benzoic acid as white solid, MS: 506 (MH⁺);
From (2S,4R)-4-[[[[4-Acetylsulfanyl-1-(4-fluoro-benzenesulfonyl)-pyrrolidine-2-carbonyl]-methyl-amino]-acetyl]-methyl-amino]-benzoic acid methyl ester: (2S,4R)-4-[[[[1-(4-Fluoro-benzenesulfonyl)-4-mercapto-pyrrolidine-2-carbonyl]-methyl-amino]-acetyl]-methyl-amino]-benzoic acid as white solid, MS: 510 (MH⁺);
From (2S,4R)-4-[[[[4-Acetylsulfanyl-1-(thiophene-2-sulfonyl)-pyrrolidine-2-carbonyl]-methyl-amino]-acetyl]-methyl-amino]-benzoic acid methyl ester: (2S,4R)-4-[[[[4-Mercapto-1-(thiophene-2-sulfonyl)-pyrrolidine-2-carbonyl]-methyl-amino]-acetyl]-methyl-amino]-benzoic acid as white solid, MS: 498 (MH⁺);
From (2S,4R)-4-[[[(4-Acetylsulfanyl-1-benzenesulfonyl-pyrrolidine-2-carbonyl)-methyl-amino]-acetyl]-methyl-amino]-benzoic acid methyl ester: (2S,4R)-4-[[(1-Benzenesulfonyl-4-mercapto-pyrrolidine-2-carbonyl)-methyl-amino]-acetyl]-methyl-amino]-benzoic acid as white solid, MS: 490 (M-H)⁻.

85 mg (0.142 mmol) (2S,4R)-4-[[[[4-Acetylsulfanyl-1-(naphthalene-1-sulfonyl)-pyrrolidine-2-carbonyl]-methyl-amino]-acetyl]-methyl-amino]-benzoic acid methyl ester in 3 ml MeOH were treated with 0.35 ml 0.6 M (0.21 mmol) NaOMe in MeOH at 0° C. for 1 h, the solution was poured on 1M KHSO₄ and extracted with EtOAc. The organic phase was washed with brine and dried over Na₂SO₄ and evaporated. The residue was titurated with hexane yielding 55 mg (60%) (2S,4R)-4-[[[[4-Mercapto-1-(naphthalene-1-sulfonyl)-pyrrolidine-2-carbonyl]-methyl-amino]-acetyl]-methyl-amino]-benzoic acid methyl ester as white solid, MS: 556 (MH⁺).

Analogously the following compounds were prepared:
From (E)-(2S,4R)-4-[[[[4-Acetylsulfanyl-1-(2-phenyl-ethenesulfonyl)-pyrrolidine-2-carbonyl]-methyl-amino]-acetyl]-methyl-amino]-benzoic acid methyl ester: (E)-(2S,4R)-4-[[[[4-Mercapto-1-(2-phenyl-ethenesulfonyl)-pyrrolidine-2-carbonyl]-methyl-amino]-acetyl]-methyl-amino]-benzoic acid methyl ester as white solid, MS: 532 (MH⁺);
From (2S,4R)-4-[[[[4-Acetylsulfanyl-1-(quinoline-8-sulfonyl)-pyrrolidine-2-carbonyl]-methyl-amino]-acetyl]-methyl-amino]-benzoic acid methyl ester: (2S,4R)-4-[[[[4-Mercapto-1-(quinoline-8-sulfonyl)-pyrrolidine-2-carbonyl]-methyl-amino]-acetyl]-methyl-amino]-benzoic acid methyl ester as white solid, MS: 557 (MH⁺);
From (2S,4R)-4-[[[[4-Acetylsulfanyl-1-(2-trifluoromethyl-benzenesulfonyl)-pyrrolidine-2-carbonyl]-methyl-amino]-acetyl]-methyl-amino]-benzoic acid methyl ester: (2S,4R)-4-[[[[4-Mercapto-1-(2-trifluoromethyl-benzenesulfonyl)-pyrrolidine-2-carbonyl]-methyl-amino]-acetyl]-methyl-amino]-benzoic acid methyl ester as white solid, MS: 574 (MH⁺);
From (2S,4R)-4-[[[[4-Acetylsulfanyl-1-(thiophene-2-sulfonyl)-pyrrolidine-2-carbonyl]-methyl-amino]-acetyl]-methyl-amino]-benzoic acid methyl ester: (2S,4R)-4-[[[[4-Mercapto-1-(thiophene-2-sulfonyl)-pyrrolidine-2-carbonyl]-methyl-amino]-acetyl]-methyl-amino]-benzoic acid methyl ester as white solid, MS: 512 (MH⁺);
From (2S,4R)-4-[[[(4-Acetylsulfanyl-1-benzenesulfonyl-pyrrolidine-2-carbonyl)-methyl-amino]-acetyl]-methyl-amino]-benzoic acid methyl ester: (2S,4R)-4-[[[(1-Benzenesulfonyl-4-mercapto-pyrrolidine-2-carbonyl)-methyl-amino]-acetyl]-methyl-amino]-benzoic acid methyl ester as white foam, MS: 506 (MH⁺).

Example 23

Preparation of Amides via Parallel Synthesis 23.1. Preparation of the Intermediate A solution of 14.82 g (29.2 mmol) (2S,4R)-4-Tritylsulfanyl-pyrrolidine-1,2-dicarboxylic acid 1-tert-butyl ester and 4.13 ml (32.1 mmol) N-benzylmethylamine in 300 ml THF was treated at 0° C. with 6.71 g (35.02 mmol) and 0.4 g (2.92 mmol) HOBT. The reaction was poured into aqueous 10% KHSO₄/EtOAc (3×). The organic phases were washed with aqueous saturated NaHCO₃ and 10% NaCl solution and dried over Na₂SO₄ to give after purification by flash-chromatography on silicagel (Hexane/EtOAc 9:1 to 1:1) 9.68 g (56%) of (2S,4R)-2-(Benzyl-methyl-carbamoyl)-4-tritylsulfanyl-pyrrolidine-1-carboxylic acid tert-butyl ester, MS: 593 (MH⁺).

19176 B73: A solution of 9.68 g (16.33 mmol) (2S,4R)-2-(Benzyl-methyl-carbamoyl)-4-tritylsulfanyl-pyrrolidine-1-carboxylic acid tert-butyl ester in 33 ml CH₂Cl₂ was treated at −20° C. with 36 ml TFA, warmed up to RT during 5.5h and kept over night at 0° C.. The reaction was evaporated and treated with aqueous saturated NaHCO₃ solution/EtOAc (3×), the organic phase was dried (Na₂SO₄) and evaporated to give 7.59 g (95%) (2S,4R)-4-Tritylsulfanyl-pyrrolidine-2-carboxylic acid benzyl-methyl-amide, MS: 493 (MH⁺).

23.2: N-Optimisation, General Procedure for the Synthesis of

Carbamate:

A solution of 0.22 mmol (2S,4R)-4-Tritylsulfanyl-pyrrolidine-2-carboxylic acid benzyl-methyl-amide in 1.7 ml dioxane was treated with 1.2 eq N-ethyldiisopropylamine and 1.2 eq chloroformate. After 16h at RT the reaction was filtered, washed with dioxane and purified by preparative HPLC (RP-16, $CH_3CN/H_2O$, UV 230 nm).

Trityl-deprotection (9.3.) gave the free thiol.

Sulfonamide:

A solution of 0.32 mmol (2S,4R)-4-Tritylsulfanyl-pyrrolidine-2-carboxylic acid benzyl-methyl-amide, 1.2 eq N-ethyldiisopropylamine and a catalytic amount of DMAP in 2 ml dichloroethane was added to 1.2 eq sulfonylchloride. After a night, the reaction was evaporated, the residue redissolve in DMF and purified by preparative HPLC (RP-16, $CH_3CN/H_2O$, UV 230 nm).

Trityl-deprotection (9.3.) gave the free thiol.

Urea:

A solution of 0.11 mmol (2S,4R)-4-Tritylsulfanyl-pyrrolidine-2-carboxylic acid benzyl-methyl-amide in 0.5 ml dioxane was treated with 0.21 mmol of the appropriate isocyanate, the reaction was kept 30 min at RT and purified by prep HPLC (RP18, $CH_3CN/H_2O$, UV 230 nm).

Trityl-deprotection (9.3.) gave the free thiol.

Amide:

0.25 mmol (2S,4R)-4-Tritylsulfanyl-pyrrolidine-2-carboxylic acid benzyl-methyl-amide, 1.5 equivalents of an acid and a catalytic amount of DMAP in 1 ml dioxane were treated with 1.5 equivalents EDCI in 1 ml $CH_2Cl_2$. The reaction was stirred over night, evaporated and purified by prep HPLC (RP18, $CH_3CN/H_2O$, UV 230 nm).

Trityl-deprotection (9.3.) gave the free thiol.

The compounds according to Table 3, 4, 5 and 6 were prepared:

TABLE 3

Amides
By reaction of (2S,4R)-4-Tritylsulfanyl-pyrrolidine-2-carboxylic acid benzyl-methyl-amide with the 2. educt:

| NAME | 2. Educt | MS | |
|---|---|---|---|
| (2S,4R)-1-Benzoyl-4-mercapto-pyrrolidine-2-carboxylic acid benzyl-methyl-amide | BENZOIC ACID | 355 | M + H + |
| (2S,4R)-4-Mercapto-1-phenylacetyl-pyrrolidine-2-carboxylic acid benzyl-methyl-amide | PHENYLACETIC ACID | 369 | M + H + |
| (2S,4R)-1-(Biphenyl-4-carbonyl)-4-mercapto-pyrrolidine-2-carboxylic acid benzyl-methyl-amide | 4-BIPHENYL-CARBOXYLIC ACID | 431 | M + H + |
| (2S,4R)-1-(Biphenyl-4-yl-acetyl)-4-mercapto-pyrrolidine-2-carboxylic acid benzyl-methyl-amide | 4-BIPHENYL-ACETIC ACID | 445 | M + H + |
| (2S,4R)-1-[(1H-Indol-3-yl)-acetyl]-4-mercapto-pyrrolidine-2-carboxylic acid benzyl-methyl-amide | INDOLE-3-ACETIC ACID | 408 | M + H + |

TABLE 4

Carbamates
By reaction of (2S,4R)-4-Tritylsulfanyl-pyrrolidine-2-carboxylic acid benzyl-methyl-amide with the 2. educt:

| NAME | 2. Educt | MS | |
|---|---|---|---|
| (2S,4R)-2-(Benzyl-methyl-carbamoyl)-4-mercapto-pyrrolidine-1-carboxylic acid benzyl ester | Benzylchloroformate | 385 | M + H + |
| (2S,4R)-2-(Benzyl-methyl-carbamoyl)-4-mercapto-pyrrolidine-1-carboxylic acid isopropyl ester | Isopropylchloroformate | 337 | M + H + |
| (2S,4R)-2-(Benzyl-methyl-carbamoyl)-4-mercapto-pyrrolidine-1-carboxylic acid phenyl ester | Phenylchloroformate | 371 | M + H + |
| (2S,4R)-2-(Benzyl-methyl-carbamoyl)-4-mercapto-pyrrolidine-1-carboxylic acid 2-chloro-ethyl ester | 2-chloroethyl-chloroformate | 357 | M + H + |
| (2S,4R)-2-(Benzyl-methyl-carbamoyl)-4-mercapto-pyrrolidine-1-carboxylic acid naphthalen-2-yl ester | Chloroformic acid 2-naphthylester | 421 | M + H + |
| (2S,4R)-2-(Benzyl-methyl-carbamoyl)-4-mercapto-pyrrolidine-1-carboxylic acid pentyl ester | Chloroformic acid N-amyl ester | 365 | M + H + |
| (2S,4R)-2-(Benzyl-methyl-carbamoyl)-4-mercapto-pyrrolidine-1-carboxylic acid isobutyl ester | ISOBUTYL CHLOROFORMATE | 351 | M + H + |
| (2S,4R)-2-(Benzyl-methyl-carbamoyl)-4-mercapto-pyrrolidine-1-carboxylic acid methyl ester | METHYL CHLOROFORMATE | 309 | M + H + |

TABLE 5

Sulfonamides
By reaction of (2S,4R)-4-Tritylsulfanyl-pyrrolidine-2-carboxylic acid benzyl-methyl-amide with the 2. educt:

| NAME | 2. Educt | MS | |
|---|---|---|---|
| (2S,4R)-4-Mercapto-1-(naphthalene-1-sulfonyl)-pyrrolidine-2-carboxylic acid benzyl-methyl-amide | 1-NAPHTHALENE-SULFONYL CHLORIDE | 441 | M + H + |
| (2S,4R)-1-Benzenesulfonyl-4-mercapto-pyrrolidine-2-carboxylic acid benzyl-methyl-amide | BENZENESULFONYL CHLORIDE | 391 | M + H + |
| (2S,4R)-4-Mercapto-1-(thiophene-2-sulfonyl)-pyrrolidine-2-carboxylic acid benzyl-methyl-amide | THIOPHENE-2-SULFONYL CHLORIDE | 397 | M + H + |
| (2S,4R)-4-Mercapto-1-(2-naphthalen-1-yl-ethanesulfonyl)-pyrrolidine-2-carboxylic acid benzyl-methyl-amide | 2-(1-NAPHTHYL)-ETHANESULFONYL CHLORIDE | 469 | M + H + |
| (2S,4R)-1-(4-Acetylamino-benzenesulfonyl)-4-mercapto-pyrrolidine-2-carboxylic acid benzyl-methyl-amide | 4-ACETAMIDO-BENZENESUL-FONYL CHLORIDE | 448 | M + H + |
| (2S,4R)-4-Mercapto-1-(2-phenyl-ethenesulfonyl)-pyrrolidine-2-carboxylic acid benzyl-methyl-amide | TRANS-BETA-STYRENESUL-FONYL CHLORIDE | 417 | M + H + |
| (2S,4R)-5-[2-(Benzyl-methyl-carbamoyl)-4-mercapto-pyrrolidine-1-sulfonyl]-2-ethoxy-benzoic acid | 5-Chlorosulfonyl-2-ethoxy-benzoic acid* | 479 | M + H + |

5-Chlorosulfonyl-2-ethoxy-benzoic acid: Dunn, Peter James; Wood, Albert Shaw. Process for preparation of Sildenafil by cyclization. Eur. Pat. Appl. EP 812845 A1

TABLE 6

Ureas
By reaction of (2S,4R)-4-Tritylsulfanyl-pyrrolidine-2-carboxylic acid benzyl-methyl-amide with the 2. educt:

| NAME | 2. Educt | MS | |
|---|---|---|---|
| (2S,4R)-4-Mercapto-pyrrolidine-1,2-dicarboxylic acid 2-(benzyl-methyl-amide) 1-[(2-fluoro-phenyl)-amide] | 2-FLUOROPHENYL ISOCYANATE | 388 | M + H + |
| (2S,4R)-4-Mercapto-pyrrolidine-1,2-dicarboxylic acid 2-(benzyl-methyl-amide) 1-naphthalen-2-ylamide | 2-NAPHTHYL ISOCYANATE | 420 | M + H + |
| (2S,4R)-4-Mercapto-pyrrolidine-1,2-dicarboxylic acid 2-(benzyl-methyl-amide) 1-naphthalen-1-ylamide | 1-NAPHTHYL ISOCYANATE | 420 | M + H + |
| (2S,4R)-4-Mercapto-pyrrolidine-1,2-dicarboxylic acid 2-(benzyl-methyl-amide) 1-(phenethyl-amide) | PHENETHYL ISOCYANATE | 398 | M + H + |
| (2S,4R)-4-Mercapto-pyrrolidine-1,2-dicarboxylic acid 2-(benzyl-methyl-amide) 1-phenylamide | PHENYL ISOCYANATE | 370 | M + H + |

23.3. A)-thioac, amid formation followed by $R^3SO2Cl$ or $R^3COCl$ treatment 4.0 g (17.3 mmol) N-BOC-L-hydroxy-proline in 150 ml $CH_2Cl_2$ were treated with 1.71 ml (17.3 mmol) piperidine, 1.9 ml (17.2 mmol) NMM and 6.16 g (20.7 mmol) TPTU at RT over night. The mixture was washed with 1M $KHSO_4$, water, 5% aq. $NaHCO_3$ solution, water and brine, dried over $Na_2SO_4$ and was concentrated. Column chromatography yielded 3.87 g (75%) (2S,4R)-4-Hydroxy-2-(piperidin-1-ylcarbonyl)-pyrrolidine-1-carboxylic acid tert-butyl ester as white solid, MS: 298 (M).

4.7 g (15.7 mmol) (2S,4R)-4-Hydroxy-2-(piperidin-1-ylcarbonyl)-pyrrolidine-1-carboxylic acid tert-butyl ester in 300 ml $CH_2Cl_2$ were treated with 4.5 g (23.6 mmol, 1.5 eq) p-toluene sulfonylchloride in the presence of 2.88 g (23.6 mmol, 1.5 eq) DMAP at RT for 48 h. The solution was washed with 1M $KHSO_4$, water, 5% aq. $NaHCO_3$ solution, water and brine, dried over $Na_2SO_4$ and was concentrated. Flash chromatography yielded 6.42 g (90%) (2S,4R)-2-(Piperidine-1-carbonyl)-4-(toluene-4-sulfonyloxy)-pyrrolidine-1-carboxylic acid tert-butyl ester as white foam.

6.39 g (14.12 mmol) (2S,4R)-2-(Piperidine-1-carbonyl)-4-(toluene-4-sulfonyloxy)-pyrrolidine-1-carboxylic acid tert-butyl ester in 50 ml DMF were treated with 2.42 g (21.18 mmol, 1.5 eq) potassium thioacetate at 100° C. for 4 h. The solution was concentrated in vacuo and the residue was dissolved in EtOAc, $NaHCO_3$ solution, the phases were separated and the inorganic layer was extracted with EtOAc. The combined organic phases were washed with water and brine, dried over $Na_2SO_4$. Column chromatography gave 3.59 g (71%) (2S,4S)-4-Acetylsulfanyl-2-(piperidine-1-carbonyl)-pyrrolidine-1-carboxylic acid tert-butyl ester as light pink solid.

1.27 g (3.56 mmol) (2S,4S)-4-Acetylsulfanyl-2-(piperidine-1-carbonyl)-pyrrolidine-1-carboxylic acid tert-butyl ester in 6 ml $CH_2Cl_2$ were treated with 3 ml TFA at 0° C. for 10 min and 20 min at RT. The solution was poured on a sat. solution of $NaHCO_3$ and was extracted with $CH_2Cl_2$, washed with water and brine, dried over $Na_2SO_4$ giving 910 mg crude product (3S,5S)-Thioacetic acid S-[5-(piperidine-1-carbonyl)-pyrrolidin-3-yl] ester which was subjected to the following reaction without further purification.

300 mg (1.17 mmol) (3S,5S)-Thioacetic acid S-[5-(piperidine-1-carbonyl)-pyrrolidin-3-yl] ester in 25 ml $CH_2Cl_2$ were treated with 398 mg (1.75 mmol, 1.5 eq) 2-naphthalene sulfonylchloride in the presence of 214 mg (1.75 mmol, 1.5 eq) DMAP at RT for 1.5 h. The solution was added to 1M $KHSO_4$, the phases were separated and the inorganic extracted with $CH_2Cl_2$, the combined organic phases were washed with 1M $KHSO_4$, water and brine, dried over $Na_2SO_4$ and were concentrated. Flash chromatography yielded 280 mg (54%) (3S,5S)-Thioacetic acid S-[1-(naphthalene-2-sulfonyl)-5-(piperidine-1-carbonyl)-pyrrolidin-3-yl] ester as white crystals.

148 mg (0.33 mmol) (3S,5S)-Thioacetic acid S-[1-(naphthalene-2-sulfonyl)-5-(piperidine-1-carbonyl)-pyrrolidin-3-yl] ester in 9 ml THF were treated with 9 ml 0.1M LiOH for 30 min at 0° C. and 1h at RT. The solution was extracted with ether, the inorganic phase was acidified with 1M $KHSO_4$ and extracted with EtOAc. The EtOAc phase was washed with brine and dried over $Na_2SO_4$, trituration with hexane gave 99 mg (74%) (2S,4S)-[4-Mercapto-1-(naphthalene-2-sulfonyl)-pyrrolidin-2-yl]-piperidin-1-yl-methanone as white solid, MS: 405 ($MH^+$).

Analogously, the following compounds were prepared from (3S,5S)-Thioacetic acid S-[5-(piperidine-1-carbonyl)-pyrrolidin-3-yl] ester and 4-tert-butyl-benzenesulfonyl chloride, 4-methoxy-benzenesulfonyl chloride, 4-n-butoxybenzene sulfonyl chloride, phenylmethane sulfonyl chloride (2.1.), p-anisoylchloride and 4-tert-butyl benzoylchloride (2.2):
- (2S,4S)-[1-(4-tert-Butyl-benzenesulfonyl)-4-mercapto-pyrrolidin-2-yl]-piperidin-1-yl-methanone as white solid, MS: 411 ($MH^+$);
- (2S,4S)-[4-Mercapto-1-(4-methoxy-benzenesulfonyl)-pyrrolidin-2-yl]-piperidin-1-yl-methanone as white solid, MS: 385 ($MH^+$);
- (2S,4S)-[1-(4-Butoxy-benzenesulfonyl)-4-mercapto-pyrrolidin-2-yl]-piperidin-1-yl-methanone as white solid, MS: 427 ($MH^+$);
- (2S,4S)-(4-Mercapto-1-phenylmethanesulfonyl-pyrrolidin-2-yl)-piperidin-1-yl-methanone as yellow sirup, MS: 369 ($MH^+$);
- (2S,4S)-[4-Mercapto-2-(piperidine-1-carbonyl)-pyrrolidin-1-yl]-(4-methoxy-phenyl)-methanone as colourless syrup, MS: 349 ($MH^+$);
- (2S,4S)-(4-tert-Butyl-phenyl)-[4-mercapto-2-(piperidine-1-carbonyl)-pyrrolidin-1-yl]-methanone as white solid, MS: 375 ($MH^+$);

23.4. B)-thioac, amid formation followed by $R^3SO2Cl$ or $R^3COCl$ treatment

Analogously, the following intermediate was prepared from N-BOC-L-hydroxy-proline and N-methylbenzylamine, followed by S-acetyl introduction and Boc-cleavage to give (3S,5S)-Thioacetic acid S-[5-(benzyl-methyl-carbamoyl)-pyrrolidin-3-yl] ester.

Treatment of (3S,5S)-Thioacetic acid S-[5-(benzyl-methyl-carbamoyl)-pyrrolidin-3-yl] ester according to the examples mentioned above with 4-methoxybenzenesulfonyl chloride, 2-naphthylsulfonyl chloride, 4-tert-butyl-benzenesulfonyl chloride, 4-n-butoxybenzene sulfonyl chloride, phenylmethane sulfonyl chloride (2.1.), p-anisoylchloride, tert. butyl benzoylchloride (2.2.) followed by S-acetyl cleavage (7.1.) gave:
- (2S,4S)-4-Mercapto-1-(4-methoxy-benzenesulfonyl)-pyrrolidine-2-carboxylic acid benzyl-methyl-amide as white solid, MS: 421 ($MH^+$);
- (2S,4S)-4-Mercapto-1-(naphthalene-2-sulfonyl)-pyrrolidine-2-carboxylic acid benzyl-methyl-amide as white solid, MS: 441 ($MH^+$);
- (2S,4S)-1-(4-tert-Butyl-benzenesulfonyl)-4-mercapto-pyrrolidine-2-carboxylic acid benzyl-methyl-amide as white solid, MS: 447 ($MH^+$);
- (2S,4S)-1-(4-Butoxy-benzenesulfonyl)-4-mercapto-pyrrolidine-2-carboxylic acid benzyl-methyl-amide as white soliod, MS: 463 ($MH^+$);
- (2S,4S)-4-Mercapto-1-phenylmethanesulfonyl-pyrrolidine-2-carboxylic acid benzyl-methyl-amide as colourless sirup, MS: 405 ($MH^+$);
- (2S,4S)-4-Mercapto-1-(4-methoxy-benzoyl)-pyrrolidine-2-carboxylic acid benzyl-methyl-amide as colourless syrup, MS: 385 ($MH^+$);
- (2S,4S)-1-(4-tert-Butyl-benzoyl)-4-mercapto-pyrrolidine-2-carboxylic acid benzyl-methyl-amide as colourless syrup, MS: 411 ($MH^+$).

23.5. D-4-mercapto pyrrolidine derivatives

Analogously to example 2 or 4 from (2R,4R)-4-Hydroxy-pyrrolidine-1,2-dicarboxylic acid 1-tert-butyl ester 2-methyl ester was prepared (2R,4S)-4-Acetylsulfanyl-pyrrolidine-1,2-dicarboxylic acid 1-tert-butyl ester 2-methyl ester as brown oil, MS: 304 ($MH^+$).

Analogously, to the disulfiddiacid formation described in the section 'disulfidacids' (example 3) the following compound was prepared from (2R,4S)-4-Acetylsulfanyl-pyrrolidine-1,2-dicarboxylic acid 1-tert-butyl ester 2-methyl ester: (2R,2'R,4S,4S')-4,4'-Disulfanediyl-bis-pyrrolidine-1,2-dicarboxylic acid 1,1'-di-tert-butyl ester as light yellow solid.

(2R,2'R,4S,4S')-4,4'-Disulfanediyl-bis-pyrrolidine-1,2-dicarboxylic acid 1,1'-di-tert-butyl ester was treated with benzyl methyl amine according to 1.2., followed by treatment with TFA according to 3.1., methan sulfonyl chloride according to 2.1. and disulfid cleavage according to 4.1. to give: (2R,4S)-4-Mercapto-1-methanesulfonyl-pyrrolidine-2-carboxylic acid benzyl-methyl-amide as light grey oil, MS: 329 ($MH^+$);
(2R,2'R,4S,4S')-4,4'-Disulfanediyl-bis-pyrrolidine-1,2-dicarboxylic acid 1,1'-di-tert-butyl ester was treated with benzyl methyl amine according to 1.2., followed by treatment with TFA 3.1., 2-naphthyl isocyanate according to 2.3. and disulfid cleavage according to 4.1. to give: (2R,4S)-4-Mercapto-pyrrolidine-1,2-dicarboxylic acid 2-(benzyl-methyl-amide) 1-naphthalen-2-ylamide as light yellow solid, MS: 420 ($MH^+$).

To a suspension of 6.7 ml (103.3 mmol) methanesulfonic acid, 14.4 ml (103.3 mmol) triethylamine and 28.8 g (107.6 mmol) triphenylphosphine in 280 ml toluene was added a suspension of 21.12 g (86.12 mmol) (2R,4R)-4-Hydroxy-pyrrolidine-1,2-dicarboxylic acid 1-tert-butyl ester 2-methyl ester [prepared according to "Synthesis of macrocyclic dilactones by cyclization of sulfonium salts". T. Nakamura, H. Matsuyama, N. Kamigata, M. Iyoda, J. Org. Chem. (1992), 57(14), 3783–9] in 180 ml toluene. After adding 21.6 ml (112 mmol) of diisopropyl azodicaboxylate (exothermic!) the solution was heated for 2.5 h at 80° C. and was stirred at RT for 1 day. 300 ml water was added at RT and extracted with ethylacetate (3×300 ml). The organic phase was washed with aqueous 1M $KHSO_4$ (2×100 ml), brine (2×150 ml), dried over $Na_2SO_4$ and evaporated to give 27.85 g (2R,4S)-4-Methanesulfonyloxy-pyrrolidine-1,2-dicarboxylic acid 1-tert-butyl ester as crude product which was dissolved in THF and treated with LiOH according to 5.2.to give (2R,4S)-4-Methanesulfonyloxy-pyrrolidine-1,2-dicarboxylic acid 1-tert-butyl ester.

Prepared from (2R,4S)-4-Methanesulfonyloxy-pyrrolidine-1,2-dicarboxylic acid 1-tert-butyl ester by treatment with N-methyl benzylamine according to 1.2. followed by treatment with triphenylmethane thiol/potassium thioacetate (See example 2, 'Preparation of esters via mesylate') to give:
(2R,4R)-2-(Benzyl-methyl-carbamoyl)-4-tritylsulfanyl-pyrrolidine-1-carboxylic acid tert-butyl ester as light yellow crystalline, MS: 593 ($MH^+$).

From (2R,4R)-2-(Benzyl-methyl-carbamoyl)-4-tritylsulfanyl-pyrrolidine-1-carboxylic acid tert-butyl ester the following compounds were prepared by BOC-cleavage in the presence of Trityl (3.2.), followed by treatment with 2-naphthyl sulfonylchloride, 4-biphenyl sulfonylchloride, isopropylsulfonylchloride, methane sulfonylchloride and 5-Chlorosulfonyl-2-ethoxy-benzoic acid according to 2.1., respectively, followed by trityl cleavage (9.1.):
(2R,4R)-4-Mercapto-1-(naphthalene-2-sulfonyl)-pyrrolidine-2-carboxylic acid benzyl-methyl-amide as white solid, MS: 441 ($MH^+$);
(2R,4R)-1-(Biphenyl-4-sulfonyl)-4-mercapto-pyrrolidine-2-carboxylic acid benzyl-methyl-amide as white solid, MS: 467 ($MH^+$);
(2R,4R)-4-Mercapto-1-(propane-2-sulfonyl)-pyrrolidine-2-carboxylic acid benzyl-methyl-amide as light brown oil, MS: 357 ($MH^+$);
(2R,4R)-4-Mercapto-1-methanesulfonyl-pyrrolidine-2-carboxylic acid benzyl-methyl-amide as white solid, MS: 329 ($MH^+$);
(2R,4R)-5-[2-(Benzyl-methyl-carbamoyl)-4-mercapto-pyrrolidine-1-sulfonyl]-2-ethoxy-benzoic acid as white solid, MS: 479 ($MH^+$).

From (2R,4R)-2-(Benzyl-methyl-carbamoyl)-4-tritylsulfanyl-pyrrolidine-1-carboxylic acid tert-butyl ester the following compounds were prepared by BOC-cleavage in the presence of Trityl (3.2.), followed by treatment with acetyl chloride, phenylacetyl chloride (2.2.), respectively, followed by trityl cleavage (9.1.):
(2R,4R)-1-Acetyl-4-mercapto-pyrrolidine-2-carboxylic acid benzyl-methyl-amide as light brown oil, MS: 293 ($MH^+$);
(2R,4R)-4-Mercapto-1-phenylacetyl-pyrrolidine-2-carboxylic acid benzyl-methyl-amide as light yellow oil, MS: 369 ($MH^+$).

From (2R,4R)-2-(Benzyl-methyl-carbamoyl)-4-tritylsulfanyl-pyrrolidine-1-carboxylic acid tert-butyl ester the following compounds were prepared by BOC-cleavage in the presence of Trityl (3.2.), followed by treatment 2-naphthylisocyante, ethylisocyanate (2.3.), respectively, followed by trityl cleavage (9.1.):
(2R,4R)-4-Mercapto-pyrrolidine-1,2-dicarboxylic acid 2-(benzyl-methyl-amide) 1-naphthalen-2-ylamide as off-white solid, MS: 420 ($MH^+$).
(2R,4R)-4-Mercapto-pyrrolidine-1,2-dicarboxylic acid 2-(benzyl-methyl-amide) 1-ethylamide as colorless oil, MS: 322 ($MH^+$).

23.6. Extended Products (amides)

To 75 mg (0.154 mmol, 1 eq) (2R,4R)-3-[4-(4-Methoxy-benzylsulfanyl)-1-(naphthalene-2-sulfonyl)-pyrrolidin-2-yl]-propionic acid in 0.86 ml THF 24 µl (0.185 mmol, 1.2 eq) benzyl methylamine were added, the solution was cooled to 0° C. and 71 mg (0.371 mmol, 2.4 eq) EDCI and 21 mg (0.151 mmol, 1.2 eq) HOBT were added. The mixture was stirred at RT over night, diluted with EtOAc and washed with 10% $KHSO_4$, sat $NaHCO_3$ solution and brine, dried over $Na_2SO_4$ and evaporated, yielding 131 mg (50%) (2R, 4R)-N-Benzyl-3-[4-(4-methoxy-benzylsulfanyl)-1-(naphthalene-2-sulfonyl)-pyrrolidin-2-yl]-N-methyl-propionamide as brown gum, which was subjected to deprotection without further purification.

To 131 mg (0.23 mmol) (2R,4R)-N-Benzyl-3-[4-(4-methoxy-benzylsulfanyl)-1-(naphthalene-2-sulfonyl)-pyrrolidin-2-yl]-N-methyl-propionamide in 8 ml TFA were added 0.37 ml (2.3 mmol, 10 eq) triethyl silane at 0° C. and the solution was stirred for 60 min at 80° C., evaporated, twice suspended in toluene and evaporated. The crude product was purified with prep. HPLC using a RPC18 column yielding 17 mg (2R,4R)-N-Benzyl-3-[4-mercapto-1-(naphthalene-2-sulfonyl)-pyrrolidin-2-yl]-N-methyl-propionamide as light yellow gum, MS: 469 ($MH^+$).

Analogously the following amides were prepared:
from (2R,4R)-3-[4-(4-Methoxy-benzylsulfanyl)-1-(naphthalene-2-sulfonyl)-pyrrolidin-2-yl]-propionic acid and benzylamine, benzyl methylamine, phenylamine, 2-Fluoro-benzyl amine, Isopropylamine, Phenethylamine, 2,3,6-trifluoro-benzylamine, 2,4,5-trifluoro-benzylamine, followed by deprotection
(2R,4R)-N-Benzyl-3-[4-mercapto-1-(naphthalene-2-sulfonyl)-pyrrolidin-2-yl]-propionamide, MS: 455 ($MH^+$);
(2R,4R)-3-[4-Mercapto-1-(naphthalene-2-sulfonyl)-pyrrolidin-2-yl]-N-phenyl-propionamide as yellow gum, MS: 441 ($MH^+$);
(2R,4R)-N-(2-Fluoro-benzyl)-3-[4-mercapto-1-(naphthalene-2-sulfonyl)-pyrrolidin-2-yl]-propionamide as light brown gum, MS: 473 ($MH^+$);
(2R,4R)-N-Isopropyl-3-[4-mercapto-1-(naphthalene-2-sulfonyl)-pyrrolidin-2-yl]-propionamide as light brown gum, MS: 407 ($MH^+$);
(2R,4R)-3-[4-Mercapto-1-(naphthalene-2-sulfonyl)-pyrrolidin-2-yl]-N-phenethyl-propionamide as light brown gum, MS: 469 ($MH^+$);
(2R,4R)-3-[4-Mercapto-1-(naphthalene-2-sulfonyl)-pyrrolidin-2-yl]-N-(2,3,6-trifluoro-benzyl)-propionamide as light brown gum, MS: 509 ($MH^+$);
(2R,4R)-3-[4-Mercapto-1-(naphthalene-2-sulfonyl)-pyrrolidin-2-yl]-N-(2,4,5-trifluoro-benzyl)-propionamide as brown gum, MS: 509 ($MH^+$).

from (2R,4R)-3-[1-Methanesulfonyl-4-(4-methoxy-benzylsulfanyl)-pyrrolidin-2-yl]-propionic acid and benzyl methylamine, followed by deprotection (2R,4R)-(N-Benzyl-3-(4-mercapto-1-methanesulfonyl-pyrrolidin-2-yl)-N-methyl-propionamide, MS: 457 ($MH^+$);

from (2R,4R)-[1-(Naphthalene-2-sulfonyl)-4-tritylsulfanyl-pyrrolidin-2-yl]-acetic acid and benzyl methylamine, benzylamine, 2,5-Difluorbenzylamine followed by deprotection, respectively:
(2R,4R)-N-Benzyl-2-[4-mercapto-1-(naphthalene-2-sulfonyl)-pyrrolidin-2-yl]-N-methyl-acetamide white solid, MS: 455 ($MH^+$).
(2R,4R)-N-Benzyl-2-[4-mercapto-1-(naphthalene-2-sulfonyl)-pyrrolidin-2-yl]-acetamide white crystalline, MS: 441 ($MH^+$).
(2R,4R)-N-(2,5-Difluoro-benzyl)-2-[4-mercapto-1-(naphthalene-2-sulfonyl)-pyrrolidin-2- yl]-acetamide white crystalline, MS: 477($MH^+$).

Example 24

Ketones and Alcohols 24.1. Ketones and Alcohols: a) in Solution Preparation of Weinreb compounds:

Under argon 6.6 g (67.4 mmol, 5.3 eq) N,O-Dimethylhydroxylamine.hydrochloride were dissolved in 100 ml toluene, treated with 32 ml (63.5 mmol, 5 eq) trimethyl aluminium at 0° C., and were stirred for 1.5 h at RT. To this solution 6.0 g (12.72 mmol, 1.0 eq) (2S,4R)-4-(4-Methoxy-benzylsulfanyl)-1-(naphthalene-2-sulfonyl)-pyrrolidine-2-carboxylic acid methyl ester in 250 ml toluene were added via a cannula, the reaction was stirred at 45° C. over night, and was added to 2M HCl at 0° C., the layers were separated, the inorganic one extracted with EtOAc, the combined organic layers were washed with brine, dried over $Na_2SO_4$, filtered and evaporated. Purification with flash chromatography on silica gel with hexane:EtOAc 2:1 yielded 3.09 g (49%) (2S,4R)-4-(4-Methoxy-benzylsulfanyl)-1-(naphthalene-2-sulfonyl)-pyrrolidine-2-carboxylic acid methoxy-methyl-amide as colorless solid, (Rf 0.2 hexane:EtOAcl:2), mp 101–102° C., MS: 501

According to general procedure 1.2. from (2S,4R)-4-(4-Methoxy-benzylsulfanyl)-1-(naphthalene-2-sulfonyl)-pyrrolidine-2-carboxylic acid and N-Methoxy-N-methyl-2-methylamino-acetamide.TFA [previously prepared from [(Methoxy-methyl-carbamoyl)-methyl]-methyl-carbamic acid tert-butyl ester* according to 3.1., * D. Jukic, M. Mayer, P. Schmitt, G. Drapeau, D. Regoli, R. Michelot, Synthesis and biological activities of neurokinin pseudopeptide analogs containing a reduced peptide bond. Eur. J. Med. Chem. (1991), 26(9), 921–8.]was prepared (2S,4R)-4-(4-Methoxy-benzylsulfanyl)-1-(naphthalene-2-sulfonyl)-pyrrolidine-2-carboxylic acid [(methoxy-methyl-carbamoyl)-methyl]-methyl-amide as colorless gum, MS: 572 (MH$^+$).

Following the general method 1.3., (2S,4R)-4-Tritylsulfanyl-pyrrolidine-1,2-dicarboxylic acid 1-tert-butyl ester and N,O-dimethylhydroxylamine-hydrochloride/N-methylmorpholine gave (2S,4R)-2-(Methoxy-methyl-carbamoyl)-4-tritylsulfanyl-pyrrolidine-1-carboxylic acid tert-butyl ester, MS: 533 (MH$^+$).

BOC-deprotection (3.2.) gave (2S,4R)-4-Tritylsulfanyl-pyrrolidine-2-carboxylic acid methoxy-methyl-amide, MS: 433 (MH$^+$).

A solution of 17.3 g (40 mmol) (2S,4R)-4-Tritylsulfanyl-pyrrolidine-2-carboxylic acid methoxy-methyl-amide in 120 ml THF was treated at 0° C. with 4 ml (50 mmol) pyridine and 5.59 ml (42 mmol) butylchloroformate. The reaction was warmed up to RT over night, evaporated and partitioned between aqueous 10% $KHSO_4/Et_2O$ (3×). The organic phases were washed with aqueous saturated $NaHCO_3$, 10% NaCl and dried over $Na_2SO_4$. Purification by flash-chromatography on silicagel (Hexane/EtOAc 4:1) gave 20.4 g (96%) of (2S,4R)-2-(Methoxy-methyl-carbamoyl)-4-tritylsulfanyl-pyrrolidine-1-carboxylic acid butyl ester, MS: 533 (MH$^+$).

Preparation of Starting Material, Aldehyde:

57 ml (57 mmol, 1.2 M soltion in toluene) of diisobutylaluminium hydride (DIBAH) was added during 40 min to a cold solution (-78° C.) of 6 g (22.7 mmol) (2S,4S)-4-Chloro-pyrrolidine-1,2-dicarboxylic acid 1-tert-butyl ester 2-methyl ester in 180 ml THF. The reaction was stirred for 2 h at –78° C. and quenched with a suspension of 23 g silica gel/23 g $MgSO_4.7H_2O$ in 70 ml aqueous 10% $KHSO_4$. The suspension was stirred for 15 min at room temperature, filtered and washed with THF. After evaporation of the THF, the residue was taken up in $CH_2Cl_2$, dried over $Na_2SO_4$ and evaporated to give 5.88 g crude (2S,4S)-4-Chloro-2-formyl-pyrrolidine-1-carboxylic acid tert-butyl ester. Preparation of ketones and alcohols:

To 0.38 ml (3 mmol) 4-bromo anisole in 8 ml THF were added 1.8 ml (2.9 mmol, 1.6 M in hexane) n-butyl lithium at –78° C. and the reaction mixture was stirred at that temperature for 1.5 h before a solution of 300 mg (0.6 mmol) prepared (2S,4R)-4-(4-Methoxy-benzylsulfanyl)-1-(naphthalene-2-sulfonyl)-pyrrolidine-2-carboxylic acid [(methoxy-methyl-carbamoyl)-methyl]-methyl-amide in 10 ml THF were added. The reaction was stirred at –78° C. for 3.5 h, sat. aq. $NH_4Cl$ solution was added and slowly warmed to RT.

The solution was acidified by further addition of 1M $KHSO_4$, and the aqueous solution was extracted with EtOAc, the organic layer was washed with brine, and dried over $Na_2SO_4$. Column chromatography yielded 140 mg (43%) (2S,4R)-[4-(4-methoxy-benzylsulfanyl)-1-(naphthalene-2-sulfonyl)-pyrrolidin-2-yl]-(4-methoxy-phenyl)-methanone as white solid.

140 mg (0.26 mmol) (2S,4R)-[4-(4-methoxy-benzylsulfanyl)-1-(naphthalene-2-sulfonyl)-pyrrolidin-2-yl]-(4-methoxy-phenyl)-methanone in 2 ml TFA were treated with 0.45 ml (6 mmol) trimethylsilyl chloride and 0.3 ml (6 mmol) DMSO for 2 h at RT, added to a sat. solution of $Na_2CO_3$ and extracted with EtOAc, washed with brine and dried. The crude product was dissolved in 6 ml acetonitrile, a sat. solution of $K_2CO_3$ in MeOH and 100 mg (0.65 mmol) DTT were added. The solution was stirred at RT for 1.5 h, the solution was acidified with 1M aq $KHSO_4$ and the inorganic phase was extracted with EtOAc. The combined organic phases were washed with brine, dried over $Na_2SO_4$, filtered and evaporated. Flash chromatography yielded 89.5 mg (81%) (2S,4R)-[4-Mercapto-1-(naphthalene-2-sulfonyl)-pyrrolidin-2-yl]-(4-methoxy-phenyl)-methanone as light yellow solid, MS: 292 (M-$C_5H_9O)^+$, 135 ($C_5H_9O)^+$.

Analogously the following compounds were prepared from prepared (2S,4R)-4-(4-Methoxy-benzylsulfanyl)-1-(naphthalene-2-sulfonyl)-pyrrolidine-2-carboxylic acid [(methoxy-methyl-carbamoyl)-methyl]-methyl-amide and isobutylmagnesium bromide, phenyl lithium (prepared from bromo-benzene and n-butyllithium) and methylmagnesium bromide, respectively, followed by PMB-thioether cleavage according to the example described above:

(2S,4R)-1-[4-Mercapto-1-(naphthalene-2-sulfonyl)-pyrrolidin-2-yl]-3-methyl-butan-1-one as colorless oil, MS: 292 (M-$C_8H_7O_2)^+$, 135 ($C_8H_7O_2)^+$·

(2S,4R)-[4-Mercapto-1-(naphthalene-2-sulfonyl)-pyrrolidin-2-yl]-phenyl-methanone as white solid, MS: 398 (MH$^+$);

(2S,4R)-1-[4-Mercapto-1-(naphthalene-2-sulfonyl)-pyrrolidin-2-yl]-ethanone as colorless solid, MS: 292 (M-$C_2H_3O)^+$, 43 ($C_2H_3O)^+$·

Analogously, the following compounds were prepared from (2S,4R)-4-(4-Methoxy-benzylsulfanyl)-1-(naphthalene-2-sulfonyl)-pyrrolidine-2-carboxylic acid [(methoxy-methyl-carbamoyl)-methyl]-methyl-amide and phenyl lithium (prepared from bromo benzene and n-butyl lithium) and isopropylmethyl magnesium bromide, respectively, followed by PMB-thioether cleavage according to the example described above:

(2S,4R)-4-Mercapto-1-(naphthalene-2-sulfonyl)-pyrrolidine-2-carboxylic acid methyl-(2-oxo-2-phenyl-ethyl)-amide as light brown oil, MS: 469 (MH$^+$);

(2S,4R)-4-Mercapto-1-(naphthalene-2-sulfonyl)-pyrrolidine-2-carboxylic acid methyl-(4-methyl-2-oxo-pentyl)-amide as yellow oil, MS: 449 (MH$^+$).

A solution of 7.69 ml (70 mmol) phenylacetylen in 140 ml THF was treated at −25° C. with 43.8 ml (70 mol) n-butyllithium (1.6 M in hexane). The reaction was warmed up to −10° C. for 1 h. A solution of 7.46 g (14 mmol) (2S,4R)-2-(Methoxy-methyl-carbamoyl)-4-tritylsulfanyl-pyrrolidine-1-carboxylic acid butyl ester in 110 ml THF was then added. After 20 min the reaction was neutralized with 190 ml of an aqueous 10% KHSO$_4$ solution. The mixture was extracted with aqueous 10% KHSO$_4$/Et$_2$O (3×). The organic phases were washed with aqueous saturated 10% NaCl, dried over Na$_2$SO$_4$, evaporated and purified by flash-chromatography on silicagel (Hexane/EtOAc 9:1) to give 6.54 g (81%) of (2S,4R)-2-(3-Phenyl-propynoyl)-4-tritylsulfanyl-pyrrolidine-1-carboxylic acid butyl ester, MS: 574 (MH$^+$).

According to general procedure 9.2. (2S,4R)-2-(3-Phenyl-propynoyl)-4-tritylsulfanyl-pyrrolidine-1-carboxylic acid butyl ester gave (2S,4R)-4-Mercapto-2-(3-phenyl-propynoyl)-pyrrolidine-1-carboxylic acid butyl ester, MS: 332 (MH$^+$).

Analogously, the following compound was prepared from (2S,4R)-4-(4-Methoxy-benzylsulfanyl)-1-(naphthalene-2-sulfonyl)-pyrrolidine-2-carboxylic acid [(methoxy-methyl-carbamoyl)-methyl]-methyl-amide and methylmagnesium bromide to give (2S,4R)-1-[4-(4-Methoxy-benzylsulfanyl)-1-(naphthalene-2-sulfonyl)-pyrrolidin-2-yl]-ethanone as colorless gum, MS: 456 (MH$^+$).

170 mg (0.37 mmol) (2S,4R)-1-[4-(4-Methoxy-benzylsulfanyl)-1-(naphthalene-2-sulfonyl)-pyrrolidin-2-yl]-ethanone in 10 ml TFA were treated with 0.75 ml (4.67 mmol, 12.56 eq) at 80° C. for 10 min. The solution was concentrated and treated a second time with 10 ml TFA and 0.75 ml (4.67 mmol, 12.56 eq) at 80° C. for 8 min. The solution was concentrated and the residue purified by flash chromatography yielding 63 mg (51%) (R) and (S)-1-[(2S,4R)-4-Mercapto-1-(naphthalene-2-sulfonyl)-pyrrolidin-2-yl]-ethanol as colorless oil, MS: 338 (MH$^+$).

According to general procedure 9.1. (45 min RT) (2S,4R)-2-(3-Phenyl-propynoyl)-4-tritylsulfanyl-pyrrolidine-1-carboxylic acid butyl ester gave after flash silicagel purification (hexane/EtOAc 9:1) (2S,4R)-2-((S) or (R)-1-Hydroxy-3-phenyl-prop-2-ynyl)-4-mercapto-pyrrolidine-1-carboxylic acid butyl ester, MS: 334 (MH$^+$)
and
(2S,4R)-2-((R) or (S)-1-Hydroxy-3-phenyl-prop-2-ynyl)-4-mercapto-pyrrolidine-1-carboxylic acid butyl ester, MS: 334 (MH$^+$).

Synthesis via Aldehyde:

A solution of 6.9 ml (62.9 mmol) phenylacetylen in 120 ml THF was treated at −25° C. with 39.3 ml (62.9 mol) n-butyllithium (1.6M in hexane). The reaction was kept at −25° C. for 20 min, then dropped to a solution of 2.94 g (12.6 mmol) crude (2S,4S)-4-Chloro-2-formyl-pyrrolidine-1-carboxylic acid tert-butyl ester in 100 ml THF which was cooled to −25° C. After 45 min the reaction was neutralized with 100 ml of an aqueous 10% KHSO$_4$ solution. The mixture was extracted with aqueous 10% KHSO$_4$/Et$_2$O (3×). The organic phases were washed with aqueous saturated 10% NaCl, dried (Na$_2$SO$_4$), evaporated and purified by flash-chromatography on silicagel (toluene/acetonitrile 195:5 to 9:1) to give 0.58 g (14%) of (2S,4S)-4-Chloro-2-((R) or (S)-1-hydroxy-3-phenyl-prop-2-ynyl)-pyrrolidine-1-carboxylic acid tert-butyl ester, MS: 336 (MH$^+$)
and
0.67 g (16%) of (2S,4S)-4-Chloro-2-((S) or (R)-1-hydroxy-3-phenyl-prop-2-ynyl)-pyrrolidine-1-carboxylic acid tert-butyl ester, MS: 336 (MH$^+$).

Hydrogenation of the Triple Bond:

A 1:1 mixture of 0.2 g (0.61 mmol) (2S,4S)-4-Chloro-2-((R) or (S)-1-hydroxy-3-phenyl-prop-2-ynyl)-pyrrolidine-1-carboxylic acid tert-butyl ester and (2S,4S)-4-Chloro-2-((S) or (R)-1-hydroxy-3-phenyl-prop-2-ynyl)-pyrrolidine-1-carboxylic acid tert-butyl ester and 20 mg Pd/C (10%) in 12 ml MeOH were hydrogenated (1 atm) over night. After filtration (celite) a 1:1 mixture of crude (2S,4S)-4-Chloro-2-((R) or (S) 1-hydroxy-3-phenyl-propyl)-pyrrolidine-1-carboxylic acid tert-butyl ester and (2S,4S)-4-Chloro-2-((S) or (R)1-hydroxy-3-phenyl-propyl)-pyrrolidine-1-carboxylic acid tert-butyl ester was received.

To a 1:1 mixture of 0.4 g (1.19 mmol) (2S,4S)-4-Chloro-2-((R) or (S)-1-hydroxy-3-phenyl-prop-2-ynyl)-pyrrolidine-1-carboxylic acid tert-butyl ester and (2S,4S)-4-Chloro-2-((S) or (R)-1-hydroxy-3-phenyl-prop-2-ynyl)-pyrrolidine-1-carboxylic acid tert-butyl ester in 12 ml DMF were added 0.2 g (1.79 mmol, 1.5 eq) potassium thioacetate and heated to 100° C. for 2.5 h. The mixture was concentrated under vacuum and the residue was purified by flash-chromatography on silicagel (hexane/EtOAc 9:1) to give 0.12 g (27%) of (2S,4R)-4-Acetylsulfanyl-2-((S) or (R)-1-hydroxy-3-phenyl-prop-2-ynyl)-pyrrolidine-1-carboxylic acid tert-butyl ester, MS: 376 (MH$^+$)
and
0.13 g (28%) of (2S,4R)-4-Acetylsulfanyl-2-[(R)- or -[(S)-1-hydroxy-3-phenyl-prop-2-ynyl)]-pyrrolidine-1-carboxylic acid tert-butyl ester, MS: 376 (MH$^+$).

In analogy to above, the crude 1:1 mixture of (2S,4S)-4-Chloro-2-((R) or (S) 1-hydroxy-3-phenyl-propyl)-pyrrolidine-1-carboxylic acid tert-butyl ester and (2S,4S)-4-Chloro-2-((S) or (R) 1-hydroxy-3-phenyl-propyl)-pyrrolidine-1-carboxylic acid tert-butyl ester gave after flash-chromatography on silicagel (CH$_2$Cl$_2$/EtOAc 99:1 to 95:1) 30% of (2S,4R)-4-Acetylsulfanyl-2-((S) or (R)-1-hydroxy-3-phenyl-propyl)-pyrrolidine-1-carboxylic acid tert-butyl ester, MS: 380 (MH$^+$)
and
20% of (2S,4R)-4-Acetylsulfanyl-2-((R) or (S)-1-hydroxy-3-phenyl-propyl)-pyrrolidine-1-carboxylic acid tert-butyl ester, MS: 380 (MH$^+$).

37.5 mg (0.1 mmol) of a 1:1 mixture of (2S,4R)-4-Acetylsulfanyl-2-((S) or (R)-1-hydroxy-3-phenyl-prop-2-ynyl)-pyrrolidine-1-carboxylic acid tert-butyl ester and (2S,4R)-4-Acetylsulfanyl-2-[(R)- or -[(S)-1-hydroxy-3-phenyl-prop-2-ynyl)]-pyrrolidine-1-carboxylic acid tert-butyl ester was dissolved in 4 ml degassed (with Argon) ethanol and treated at 0° C. with 0.3 ml aqueous 1N LiOH. After 1 h at this temperature the reaction was stirred for 5 h at RT. The solution was cooled (0° C.), neutralized with aqueous 10% KHSO$_4$/Et$_2$O (3×). The organic phases were washed with aqueous 10% NaCl solution and dried (Na$_2$SO$_4$) to give 32 mg (96%) of (2S,4R)-2-((S) and (R)-1-Hydroxy-3-phenyl-prop-2-ynyl)-4-mercapto-pyrrolidine-1-carboxylic acid tert-butyl ester, MS: 334 (MH$^+$).

In analogy to above, (2S,4R)-4-Acetylsulfanyl-2-((S) or (R)-1-hydroxy-3-phenyl-propyl)-pyrrolidine-1-carboxylic acid tert-butyl ester gave quantitative (2S,4R)-2-((S) or (R)-1-Hydroxy-3-phenyl-propyl)-4-mercapto-pyrrolidine-1-carboxylic acid tert-butyl ester, MS: 338 (MH$^+$).

24.2. Ketones and Alcohols: b) Solid Phase Synthesis

Preparation of the Resin:
Building Block Synthesis
(2S,4R)-4-(4-Methoxy-benzylsulfanyl)-pyrrolidine-1,2-dicarboxylic acid 1-tert-butyl ester (19.48 g, 53 mmol)

was treated with TFA (80 ml) in CH$_2$Cl$_2$ (120 ml) for 15 min. The reaction mixture was concentrated under reduced pressure and the resultant dark red oil was triturated in diethyl ether/n-hexane (1:4 v/v, 860 ml). The precipitated salt was collected and dried under reduced pressure (18.9 g) and directly used in the next step.

The TFA salt (18.9 g, 53 mmol) of (2S,4R)-4-(4-methoxy-benzylsulfanyl)-pyrrolidine-2-carboxylic acid in 1,4-dioxane/H$_2$O (300 ml) containing NaHCO$_3$ (17.8 g, 212 mmol) was treated with Fmoc—OSu (19.7 g, 58.3 mmol) and magnetically stirred for 16 h. The reaction mixture was diluted with water (400 ml) and washed with diethyl ether (2×). Ethyl acetate (400 ml) and HCl (25%, 50 ml) were added. The organic phase was extracted and washed H$_2$O, NaCl sat. and dried MgSO$_4$. Filtration and concentration under reduced pressure yielded a foam (22.5 g).

The above foam (20.7 g, 42.3 mmol) was dissolved in TFA (350 ml) and triisopropylsilane (43.5 ml) was added. The mixture was refluxed for 0.5 h and concentrated under reduced pressure. Diethyl ether (100 ml) and n-hexanes (300 ml) were added yielding a precipitate. The supernatant was decanted and the precipitate was dried under reduced pressure and high vacuum to yield a white foam (2S,4R)-4-sulfanyl-1-(fluorenylmethoxycarbonyl)-pyrrolidine-2-carboxylic acid (9.6 g, MS: 370 MH$^+$).

Resin Derivatization

The linker 4-(alpha,alpha-diphenylhydroxymethyl) benzoic acid (18.3 g, 60 mmol) was activated using TPTU (17.8 g, 60 mmol), DIEA (30.8 ml, 180 mmol) in DMF(abs., 250 ml) for 3 min. The mixture was added to a flask containing benzhydrylamine resin (loading-NH2 0.9 mmol/g, 44.4 g) and the flask was shaken for 1 h. The resin was collected on a filter and washed (3× alternating DMF/isopropanol), CH$_2$Cl$_2$, ether and dried: 54.65 g, 0.65 mmol/g (loading based on mass increase).

To the CH$_2$Cl$_2$ washed resin above (46.9 g, 30 mmol), was added a mixture of (2S,4R)-4-sulfanyl-1-(naphthalene-2-sulfonyl)-pyrrolidine-2-carboxylic acid 12.2 g, 36 mmol) in CH$_2$Cl$_2$ (abs. 550 ml), TFA (80 ml). The red colored mixture was shaken for 1.5 h and the resin was then filtered, washed (3× alternating CH$_2$Cl$_2$/isopropanol), CH$_2$Cl$_2$, ether and dried: 42 g, 0.65 mmol/g (loading based on mass increase).

To the CH$_2$Cl$_2$ washed resin above (33.5 g, 22 mmol), was added a mixture of (2S,4R)-4-sulfanyl-1-(fluorenylmethoxycarbonyl)-pyrrolidine-2-carboxylic acid (9.7 g, 26 mmol) in CH$_2$Cl$_2$ (abs. 450 ml), TFA (67 ml). The red colored mixture was shaken for 1.5 h and the resin was then filtered, washed (3× alternating CH$_2$Cl$_2$/isopropanol), CH$_2$Cl$_2$, ether and dried: 42 g, 0.59 mmol/g (loading based on mass increase).

Preparation of the Products: Parallel Chemistry on Solid Phase—Ketones

Resin derivatized with (2S,4R)-4-sulfanyl-1-(fluorenylmethoxycarbonyl)-pyrrolidine-2-carboxylic acid (9.71 g, 5.73 mmol) above, was treated with DMF (abs. 80 ml), TPTU (3.4 g, 11.46 mmol), DIEA (2.94 ml, 17.2 mmol) for 15 min. The DMF solution was removed under vacuum and the reaction flask was charged with N,O-dimethylhydroxylamine.hydrochloride (1.68 g, 17.2 mmol) in DMF (abs. 80 ml). The reaction mixture was shaken for 2 h and the resin was collected at the filter, washed (3× alternating DMF/isopropanol), DMF. The resin (1.0 g, 0.6 mmol) was washed with THF(abs.2×) under an argon overpressure resuspended in THF (abs. 8 ml) and treated with 4-fluorophenyl magnesiumbromide (1M in THF, 5.9 ml). After 4 h the resin was filtered off and washed with THF. 0.5 N KHSO$_4$ was added and the reaction flask was shaken for 15 min. The resin was further washed DMF, 0.5 N KHSO$_4$, (alternating DMF, MeOH, H$_2$O ), DMF, CH$_2$Cl$_2$, diethyl ether and dried. The resin (0.38 mg) was treated with 40% TFA/CH$_2$Cl$_2$ (10 ml), triisopropylsilane (0.5 ml) for 1 h and the filtrate was collected and concentrated under reduced pressure and the residue was purified by prep.RP-HPLC and the desired fractions were pooled and freeze-dried from acetic acid (10 ml) yielding (2S,4R)-2-(4-fluoro-benzoyl)-4-mercapto-pyrrolidine-1-carboxylic acid 9H-fluoren-9-ylmethyl ester MS: 448.3 (MH$^+$).

Furthermore, Fmoc group removal was achieved with 20% piperidine/DMF (2×5 min) and typical pyrrolidine substitution reactions followed e.g, To this resin (0.33 g, 0.20 mmol) was added DMF (abs. 5 ml), pyridine (0.16 ml, 1.95 mmol), and a solution of naphthalene-2-sulfonyl chloride (0.09 g, 0.39 mmol) in DMF (abs. 1 ml). The mixture was shaken for 16 h and the resin was collected at the filter, washed (3× alternating DMF/isopropanol), CH$_2$Cl$_2$, ether and dried. This resin (0.25 mg) was treated with 40% TFA/CH$_2$Cl$_2$ (10 ml), triisopropylsilane (0.5 ml) for 1 h and the filtrate was collected and concentrated under reduced pressure and the residue was purified by prep. RP-HPLC and the desired fractions were pooled and freeze-dried from acetic acid (10 ml) yielding (2S,4R)-(4-fluoro-phenyl)-[4-mercapto-1-(naphthalene-2-sulfonyl)-pyrrolidin-2-yl]-methanone MS: 416.3(MH$^+$).

Other compounds prepared in parallel, via the above procedure, were indicated in Table 7:

TABLE 7

By reaction of resin bound (2S, 4R)-4-sulfanyl-1-(fluorenylmethoxycarbonyl)-pyrrolidine-2-carboxylic acid with educts listed below:

| Name | Ion-Spray MS | Educts |
|---|---|---|
| (2S,4R)-2-(4-Fluoro-benzoyl)-4-mercapto-pyrrolidine-1-carboxylic acid butyl ester | M + H 326.4 | 1. N,O-Dimethyl-hydroxylamine hydrochloride<br>2. 4-Fluorophenyl magnesium bromide<br>3. 20% piperidine/DMF<br>4. Butyl chloroformate |
| (2S,4R)-4-Mercapto-2-(3-phenyl-propionyl)-pyrrolidine-1-carboxylic acid 9H-fluoren-9-ylmethyl ester | M + HN4 475.3 | 1. N,O-Dimethyl-hydroxylamine hydrochloride.<br>2. Phenyl ethyl magnesiumchloride |
| (2S,4R)-1-[4-Mercapto-1-(naphthalene-2-sulfonyl)-pyrrolidin-2-yl]-3-phenyl-propan-1- | M + H 426.3 | 1. N,O-Dimethyl-hydroxylamine hydrochloride.<br>2. Phenyl ethyl magnesiumchloride |

TABLE 7-continued

By reaction of resin bound (2S, 4R)-4-sulfanyl-1-(fluorenylmethoxycarbonyl)-
pyrrolidine-2-carboxylic acid with educts listed below:

| Name | Ion-Spray MS | Educts |
| --- | --- | --- |
| one | | 20% piperidine/DMF |
|  |  | 4. Toluene-4-sulfonyl chloride |
| (2S,4R)-4-Mercapto-2-(3-phenyl-propionyl)-pyrrolidine-1-carboxylic acid butyl ester | M + H 336.3 | 1. N,O-Dimethyl-hydroxylamine hydrochloride. |
|  |  | 2. Phenyl ethyl magnesiumchloride |
|  |  | 3. 20% piperidine/DMF |
|  |  | 4. Butyl chloroformate |

Example 25

Synthesis of Pyrrolidine-derivatives 25.1. Direct Synthesis: See Example 22

25.2. Synthesis of Prodrugs from the Corresponding Mercaptanes: S-Acetyl-Prodrugs The preparation of the starting materials (mercaptane) is described above.

150 mg (0.32 mmol) (2S,4S)-1-[4-Mercapto-1-(naphthalene-2-sulfonyl)-pyrrolidine-2-carbonyl]-piperidine-4-carboxylic acid ethyl ester in 2 ml pyridine were treated with 60 μl (0.63 mmol, 2 eq) acetic anhydride for 5 h at RT. Ethanol was added, the solution stirred at RT for 10 min and concentrated. The residue was dissolved in $CH_2Cl_2$, extracted with 1M HCl, 5% $NaHCO_3$ solution and brine, dried over $Na_2SO_4$ and purified by column chromatography to give 60 mg (37%) 1-[(2S,4S)-4-acetylsufanyl-1-(naphthalene-2-sulfonyl)-pyrrolidine-2-carbonyl]-piperidine-4-carboxylic acid ethyl ester as white foam, MS: 519 ($MH^+$).

A solution of 124 mg (0.2 mmol) (2S,4R)-{[4-Mercapto-1-(naphthalene-2-sulfonyl)-pyrrolidine-2-carbonyl]-phenethyl-amino}-acetic acid in 3.2 ml pyridine were treated at 0° C. with 0.04 ml (0.4 mmol) acetyl chloride and stirred for 10 min at RT. The reaction was poured on ice water and extracted wit 1N HCl/EtOAc (3×). The organic phases were washed with aqueous 1 N HCl and 10% NaCl, dried over $Na_2SO_4$ and evaporated. Precipitation from $CH_2Cl_2$/Pentane (4° C.) gave 30 mg (28%) (2S,4R)-{[4-Acetylsulfanyl-1-(naphthalene-2-sulfonyl)-pyrrolidine-2-carbonyl]-phenethyl-amino}-acetic acid, mp: 190–193° C.; MS: 539 (M-H)$^-$.

A suspension of 700 mg (1.29 mmol) (2S,4R)-{[4-Acetylsulfanyl-1-(naphthalene-2-sulfonyl)-pyrrolidine-2-carbonyl]-phenethyl-amino}-acetic acid and 0.1 ml (1.68 mmol) EtOH in 12 ml $CH_2Cl_2$ was treated at 0° C. with 273 mg (1.42 mmol) EDCI and 16 mg (0.13 mmol) DMAP. After warming up to RT (1 h), the reaction was partitioned between aqueous 10% $KHSO_4$/$Et_2O$ (3×). The organic phases were washed with aqueous saturated $KHCO_3$, 10% NaCl and dried over $Na_2SO_4$. Purification by flash-chromatography on silicagel (Hexane/EtOAc 9:1 to 4:1) gave 0.254 mg (34%) (2S,4R)-{[4-Acetylsulfanyl-1-(naphthalene-2-sulfonyl)-pyrrolidine-2-carbonyl]-phenethyl-amino}-acetic acid ethyl ester, mp: 119–120° C., MS: 569 ($MH^+$).

25.3 Synthesis of Disulfides e.g. S—Cys-derivatives:

(2S,4R)-{[4-Mercapto-1-(naphthalene-2-sulfonyl)-pyrrolidine-2-carbonyl]-phenethyl-amino}-acetic acid (35.2 mg, 0.07 mmol) and Boc-Cys(Npys)—OH (Bachem A-2825, 26.3 mg, 0.07 mmol) were dissolved in argon-degassed DMF (abs. 2 ml) and degassed 0.1 M phosphate buffer (pH 6.2, 2 ml) was added. The reaction mixture was magnetically stirred for 2 h under argon. Ethyl acetate (30 ml), water (20 ml) were added and the organic phase was washed with water (3×20 ml) and concentrated under reduced pressure to give a yellow oil: 53 mg. The oil was dissolved in 4 M HCl/1,4-dioxane (5 ml) for 0.5 h. Diethyl ether (30 ml) was added and the precipitated product was filtered, washed with diethyl ether and dried: 37 mg. Prep. RP-HPLC purification followed by pooling and freeze-drying of desired fractions yielded 2-amino-3-[5-(carboxymethyl-phenethyl-carbamoyl)-1-(naphthalene-2-sulfonyl)-pyrrolidin-3-yldisulfanyl]-propionic acid; compound with trifluoro-acetic acid as a white lyophilisate (26 mg) MS: 616.3 (M-H)$^-$(MH$^-$)

(2S,4R)-{[4-Mercapto-1-(naphthalene-2-sulfonyl)-pyrrolidine-2-carbonyl]-phenethyl-amino}-acetic acid (32.6 mg, 0.07 mmol) and Ac-Cys(Npys)—OH (20.6 mg, 0.07 mmol) were dissolved in argon-degassed DMF (abs. 2 ml) and degassed 0.1 M phosphate buffer (pH 6.2, 2 ml) was added. The reaction mixture was magnetically stirred for 2 h under argon. Ethyl acetate (30 ml), water (20 ml) were added and the organic phase was washed with water (3×20 ml) and concentrated under reduced pressure to give a yellow oil: 37 mg. Prep. RP-HPLC purification followed by pooling and freeze-drying of desired fractions yielded 2-acetylamino-3-[5-(carboxymethyl-phenethyl-carbamoyl)-1-(naphthalene-2-sulfonyl)-pyrrolidin-3-yldisulfanyl]-propionic acid as a white lyophilisate (20 mg) MS: 657.9 (M-H)$^-$.

EXAMPLE A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

EXAMPLE B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

EXAMPLE C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

EXAMPLE D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single dosages which can be applied individually.

What is claimed is:

1. A compound of formula I

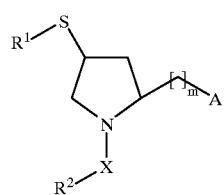

(I)

wherein $R^1$ is hydrogen, alkylcarbonyl, or arylcarbonyl;

$R^2$ is alkyl, alkylcycloalkyl, alkylcycloalkylalkyl, cycloalkyl, halogenalkyl, carboxyalkyl, aminoalkyl, dialkylaminoalkyl, alkoxyalkyl, alkoxycarbonylalkyl, alkinyl, aryl, arylalkyl, arylalkyl(alkoxycarbonyl)alkyl, arylcarbonylalkyl, aryloxyalkyl, arylalkenyl, aryl (alkoxycarbonyl)alkyl, heteroaryl, heteroarylalkyl, heterocyclyl or hetercycylalkyl;

A is —C(O)—$NR^5R^6$, wherein —$NR^5R^6$ together form a pyrrolindinyl or piperidinyl ring substituted with carboxy, alkyloxycarbonyl, hydroxy, alkoxycarbonylalkoxy, phenylalkyl or phenylalkoxycarbonyl;

m is 0, 1, or 2;

X is —$SO_2$, —CO—, —C(O)O—, —$SO_2NH$—, or —C(O)$NR^{13}$— wherein $R^{13}$ is hydrogen, alkyl, aryl, or carboxyalkyl;

or a dimeric form, or a pharmaceutically acceptable ester, or a pharmaceutically acceptable salt thereof.

2. A compound according to claim 1 wherein $R^1$ is hydrogen or alkylcarbonyl.

3. A compound according to claim 2, wherein $R^1$ is hydrogen or acetyl.

4. A compound according to claim 3, wherein $R^1$ is hydrogen.

5. A compound according to claim 1, wherein $R^2$ is alkyl, alkylcycloalkyl, alkylcycloalkylalkyl, cycloalkyl, halogenalkyl, carboxyalkyl, aryl, arylalkyl, arylalkyl (alkoxycarbonyl)alkyl, arylcarbonylalkyl, aryloxyalkyl, arylalkenyl, or aryl(alkoxycarbonyl)alkyl.

6. A compound according to claim 5, wherein $R^2$ is alkyl, aryl or arylalkyl.

7. A compound according to claim 6, wherein $R^2$ is alkyl, naphthyl or phenyl.

8. A compound according to claim 7, wherein $R^2$ is naphthyl.

9. A compound according to claim 1, wherein X is —$SO_2$—.

10. A compound according to claim 1, wherein X is —C(O)O—.

11. A compound according to claim 1, wherein m is 0.

12. A compound according to claim 1, wherein —$NR^5R^6$ is piperidinyl or pyrrolidinyl, unsubstituted or substituted with alkoxycarbonyl or carboxy.

13. A compound according to claim 1, (2S,4S)-1-[4-Mercapto-1-(naphthalene-2-sulfonyl)-pyrrolidine-2-carbonyl]-piperidine-4-carboxylic acid ethyl ester.

14. A compound according to claim 1, (2S,4S)-1-[4-Mercapto-1-(naphthalene-2-sulfonyl)-pyrrolidine-2-carbonyl]-piperidine-4-carboxylic acid.

15. A compound according to claim 1, (2S,4S)-1-[4-acetylsufanyl-1-(naphthalene-2-sulfonyl)-pyrrolidine-2-carbonyl]-piperidine-4-carboxylic acid ethyl ester.

* * * * *

UNITED STATES PATENT AND TRADEMARK OFFICE
CERTIFICATE OF CORRECTION

PATENT NO.    : 6,541,638 B2
DATED         : April 1, 2003
INVENTOR(S)   : Johannes Aebi et al.

It is certified that error appears in the above-identified patent and that said Letters Patent is hereby corrected as shown below:

Column 102,
Line 39, delete "unsubstituted or".

Signed and Sealed this

Twenty-sixth Day of August, 2003

JAMES E. ROGAN
*Director of the United States Patent and Trademark Office*